US010842882B2

(12) United States Patent
Anderl et al.

(10) Patent No.: US 10,842,882 B2
(45) Date of Patent: Nov. 24, 2020

(54) AMATOXIN-ANTIBODY CONJUGATES

(71) Applicant: HEIDELBERG PHARMA GMBH, Ladenburg (DE)

(72) Inventors: Jan Anderl, Modautal (DE); Torsten Hechler, Lauteral (DE); Christoph Müller, Birkenau (DE); Andreas Pahl, Heidelberg (DE)

(73) Assignee: Heidelberg Pharma GmbH, Ladenburg (DE)

( * ) Notice: Subject to any disclaimer, the term of this patent is extended or adjusted under 35 U.S.C. 154(b) by 119 days.

(21) Appl. No.: 15/556,830

(22) PCT Filed: Mar. 7, 2016

(86) PCT No.: PCT/EP2016/000397
§ 371 (c)(1),
(2) Date: Sep. 8, 2017

(87) PCT Pub. No.: WO2016/142049
PCT Pub. Date: Sep. 15, 2016

(65) Prior Publication Data
US 2018/0043033 A1 Feb. 15, 2018

(30) Foreign Application Priority Data
Mar. 9, 2015 (EP) ..................... 15000681

(51) Int. Cl.
| A61K 47/68 | (2017.01) |
| C07K 16/32 | (2006.01) |
| C07K 7/64 | (2006.01) |
| A61K 38/12 | (2006.01) |
| C07K 16/30 | (2006.01) |

(52) U.S. Cl.
CPC .......... *A61K 47/6855* (2017.08); *A61K 38/12* (2013.01); *A61K 47/6831* (2017.08); *A61K 47/6851* (2017.08); *C07K 7/64* (2013.01); *C07K 16/30* (2013.01); *C07K 16/32* (2013.01); C07K 2317/24 (2013.01); C07K 2317/52 (2013.01); C07K 2319/55 (2013.01)

(58) Field of Classification Search
CPC ................ A61K 47/68; A61K 47/6801; A61K 47/6811; A61K 47/6831; A61K 47/6835; A61K 47/6843; A61K 47/6849; A61K 47/6851; A61K 47/6855
See application file for complete search history.

(56) References Cited

U.S. PATENT DOCUMENTS

2010/0158909 A1* 6/2010 McDonagh ........ A61K 51/1027
424/134.1

FOREIGN PATENT DOCUMENTS

| JP | 2013-523895 A | 6/2013 | | |
| WO | 2008/070593 A2 | 6/2008 | | |
| WO | 2011/130598 A1 | 10/2011 | | |
| WO | 2014/043403 A1 | 3/2014 | | |
| WO | 2014/159981 A2 | 10/2014 | | |
| WO | 2015/023355 A1 | 2/2015 | | |
| WO | WO-2015123265 A1 * | 8/2015 | ............. | C07K 16/00 |
| WO | WO-2016071856 A1 * | 5/2016 | ............... | C07K 7/64 |

OTHER PUBLICATIONS

Irani et al, Molecular Immunology, 2015, vol. 67, pp. 171-182 (Year: 2015).*
Turner et al, International Journal for Parasitology, 2005, vol. 35, pp. 981-990 (Year: 2005).*
Junutula et al (Journal of Immunological Methods, 2008, vol. 332, pp. 41-52) (Year: 2008).*
Panowski et al (mAbs, Jan.-Feb. 2014, vol. 6, pp. 34-45) (Year: 2014).*
Sanchez et al (Chemical Communications, 2013, vol. 49, pp. 309-311) (Year: 2013).*
IMGT Scientific Chart, 4 pages (downloaded from the Web on Aug. 9, 2017) (Year: 2017).*
International Search Report dated Jun. 1, 2016 in PCT/EP2016/000397 (5 pages).
Written Opinion dated Jun. 1, 2016 in PCT/EP2016/000397 (6 pages).
Ben-Quan Shen et al., "Conjugation site modulates the in vivo stability and therapeutic activity of antibody-drug conjugates", Nature Biotechnology, vol. 30, No. 2, Jan. 22, 2012 (Jan. 22, 2012) , pp. 184-189.
May S Kung et al., "SGN-CD33A: a novel CD33-targeting antibody-drug conjugate using a pyrrolobenzodiazepine dimer is active in models of drug-resistant AML", Blood, vol. 122, No. 8, Aug. 22, 2013 (Aug. 22, 2013) , pp. 1455-1463.
Xavier Elduque et al. "Protected Maleimide Building Blocks for the Decoration of Peptides, Peptoids, and Peptide Nucleic Acids", Bioconjugate Chemistry, vol. 24, No. 5, May 15, 2013 (May 15, 2013) , pp. 832-839.
Albert Sanchez et al., "Maleimide-Dimethylfuran exo Adducts: Effective Maleimide Protection in the Synthesis of Oligonucleotide Conjugates", Organic Letters, vol. 13, No. 16, Aug. 19, 2011 (Aug. 19, 2011) , pp. 4364-4367.
Gerald M Edelman et al., "The covalent structure of an entire gammaG immunoglobulin molecule", Proceedings of the National Academy of Sciences, vol. 63, No. I, May 15, 1969 (May 15, 1969), pp. 78-85.
Elduque et al., Protected Maleimide Building Blocks for the Decoration of Peptides, Peptoids, and Peptide Nucleic Acids, Bioconjugate Chemistry, 24(5):832-839 (May 15, 2013).

(Continued)

Primary Examiner — Karen A. Canella
(74) Attorney, Agent, or Firm — Prismatic Law Group, PLLC

(57) ABSTRACT

The invention relates to conjugates comprising amatoxins and antibodies, in particular amatoxins linked to antibodies comprising specific cysteine residues.

9 Claims, 30 Drawing Sheets

(56) References Cited

OTHER PUBLICATIONS

Junutula et al., "Site-specific conjugation of a cytotoxic drug to an antibody improves the therapeutic index," Nature Biotechnology, 26(8):925-932 (Aug. 2008).
Klinguer-Hamour et al., "World Antibody-Drug Conjugate Summit, Oct. 15-16, 2013, San Francisco, CA," mAbs, 6(1):18-29 (Jan./Feb. 2014, published online Dec. 6, 2013).

* cited by examiner

|  | R₁ | R₂ | R₃ | R₄ |
|---|---|---|---|---|
| α-amanitin | OH | OH | NH₂ | OH |
| β-amanitin | OH | OH | OH | OH |
| γ-amanitin | H | OH | NH₂ | OH |
| ε-amanitin | H | OH | OH | OH |
| amanin | OH | OH | OH | H |
| amaninamide | OH | OH | NH₂ | H |
| amanullin | H | H | NH₂ | OH |
| amanullinic acid | H | H | OH | OH |

3_Her_30.0643_reduziert_HC

| Mass (Da) | Intensity | Score | Delta Mass | %Relative | %Total |
|---|---|---|---|---|---|
| 49508.7 | 1.20E+006 | 40.12 | 0.0 | 100.00 | 55.17 |
| 50551.5 | 5.57E+005 | 24.10 | 1042.8 | 46.42 | 25.61 |
| 48685.9 | 2.41E+005 | 6.35 | -822.8 | 20.08 | 11.08 |
| 51603.1 | 1.77E+005 | 4.03 | 2094.4 | 14.75 | 8.14 |

FIG. 9

| TDC | 15 mg/kg | 25 mg/kg | 37.5 mg/kg |
|---|---|---|---|
| Ab B HC-A118C | ✓ | ✓ | ✓ |
| Ab B HC-S131C | nd* | nd* | nd* |
| Ab B HC-S239C | ✓ | ✓ | nd*** |
| Ab B HC-D265C | ✓ | ✓ | nd*** |
| Ab B HC-E269C | ✓ | ✓ | X(2/3) |
| Ab B HC-N297C | ✓ BWL | X(3/3) | nd** |
| Ab B HC-A327C | ✓ | ✓ | X(3/3) |
| Ab B HC-I332C | ✓ BWL | X(3/3) | nd** |

AMATOXIN-ANTIBODY CONJUGATES

CROSS-REFERENCE TO RELATED APPLICATIONS

The present invention is filed under 35 U.S.C. § 371 as the U.S. national phase of International Patent Application No. PCT/EP2016/000397, filed Mar. 7, 2016, which designated the United States and which claims priority to European Patent Application No. 15000681.5 filed Mar. 9, 2015, each of which is hereby incorporated in its entirety including all tables, figures and claims.

FIELD OF THE INVENTION

The invention relates to conjugates comprising amatoxins and antibodies, in particular amatoxins linked to antibodies comprising specific cysteine residues.

BACKGROUND OF THE INVENTION

Amatoxins are cyclic peptides composed of 8 amino acids that are found in *Amanita phalloides* mushrooms (see FIG. 1). Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA-polymerase II is very tight ($K_D$=3 nM). Dissociation of amanitin from the enzyme is a very slow process, thus making recovery of an affected cell unlikely. When the inhibition of transcription lasts too long, the cell will undergo programmed cell death (apoptosis).

The use of amatoxins as cytotoxic moieties for tumour therapy had already been explored in 1981 by coupling an anti-Thy 1.2 antibody to α-amanitin using a linker attached to the indole ring of Trp (amino acid 4; see FIG. 1) via diazotation (Davis & Preston, Science 1981, 213, 1385-1388). Davis & Preston identified the site of attachment as position 7'. Morris & Venton demonstrated as well that substitution at position 7' results in a derivative, which maintains cytotoxic activity (Morris & Venton, Int. J. Peptide Protein Res. 1983, 21 419-430).

Patent application EP 1 859 811 A1 (published Nov. 28, 2007) described conjugates, in which the γ C-atom of amatoxin amino acid 1 of β-amanitin was directly coupled, i.e. without a linker structure, to albumin or to monoclonal antibody HEA125, OKT3, or PA-1. Furthermore, the inhibitory effect of these conjugates on the proliferation of breast cancer cells (MCF-7), Burkitt's lymphoma cells (Raji) and T-lymphoma cells (Jurkat) was shown. The use of linkers was suggested, including linkers comprising elements such as amide, ester, ether, thioether, disulfide, urea, thiourea, hydrocarbon moieties and the like, but no such constructs were actually shown, and no more details, such as attachment sites on the amatoxins, were provided.

Patent applications WO 2010/115629 and WO 2010/115630 (both published Oct. 14, 2010) describe conjugates, where antibodies, such as anti-EpCAM antibodies such as humanized antibody huHEA125, are coupled to amatoxins via (i) the γ C-atom of amatoxin amino acid 1, (ii) the 6' C-atom of amatoxin amino acid 4, or (iii) via the δ C-atom of amatoxin amino acid 3, in each case either directly or via a linker between the antibody and the amatoxins. The suggested linkers comprise elements such as amide, ester, ether, thioether, disulfide, urea, thiourea, hydrocarbon moieties and the like. Furthermore, the inhibitory effects of these conjugates on the proliferation of breast cancer cells (cell line MCF-7), pancreatic carcinoma (cell line Capan-1), colon cancer (cell line Colo205), and cholangiocarcinoma (cell line OZ) were shown.

The approaches mentioned above suffer from the disadvantage that coupling to lysine residues in proteinaceous target-binding domains such as antibodies is non-specific and results in conjugates of mixed composition with varying drug-antibody ratios (DAR), which cannot satisfactorily be controlled. For example, there are between about 70 and 100 lysine amino acid residues in a typical human IgG1 antibody. Typically a DAR of about 4 is obtained by reaction of appropriately activated amatoxin constructs with lysine residues. Additionally, a very heterogeneous mixture of coupling positions is observed, with some resulting in conjugates of higher efficacy and some with much lower efficacy. No particular degree of control is available here.

Similarly, the use of cysteines obtained by reducing disulfide bonds in antibody molecules followed by coupling to toxins carrying a thiol-reactive group results in the formation of heterogeneous mixtures, since there are 32 cysteines in a human IgG1, and eight thereof are available for coupling after reduction of four interchain disulfide bonds.

It can be observed that the cytotoxic activity and thus the therapeutic efficacy of toxin-antibody conjugates, increases with the DAR being obtained. However, simultaneously, the tolerability decreases with increased DAR. Thus, in order to optimize the profile of a toxin-antibody conjugate, it is highly desirable to control both the number of toxins being coupled to the antibody (i.e. the DAR), as well as the specific location(s) of the toxin conjugation(s). Only in such circumstances, the fine-tuning of the available therapeutic window, and the reproducibility of the results, can be achieved.

In reaction to this situation, a number of methods have been developed for the specific and controlled generation of drug-antibody conjugates, including for example, site-specific conjugation to non-naturally occurring amino acids that have been introduced in wild-type antibody sequences (see Axup et al., Proc. Natl. Acad. Sci. U.S.A. 109 (2012) 16101).

An alternative approach uses antibody constructs comprising single cysteine residues that are obtained by mutagenesis of wild-type antibody sequences. Ideally, a DAR of 2 can be reached by mutagenesis of a single amino acid residue in a light or heavy chain of an IgG having two copies of such mutated chain, and a DAR of 1 can be reached by mutagenesis of a single amino acid residue in a light or heavy chain of a monovalent antibody fragment, such as an Fab fragment, having one copy of any such mutated chain.

WO 2006/034488 describes antibodies that are engineered by replacing one or more amino acids of a parent antibody with non-cross-linked, highly reactive cysteine amino acids. The application describes various positions in both the light and the heavy chain, where such a replacement may take place.

WO 2011/005481 is another application, which presents a large number of positions, which could be used for the replacement of wild-type amino acid residues in antibody sequences by reactive amino acid residues, in particular by cysteine residues.

WO 2008/070593 describes a similar approach, wherein amino acid residues in the Fc part on an antibody, which are involved in Fc gamma receptor binding, are exchanged, including exchanges by cysteine residues.

Despite the fact that much work has already been done in this area, no amatoxins have yet been coupled in a defined manner by controlling the DAR ratio. e.g. by using specific cysteines for such defined coupling. Furthermore, there doesn't seem to be a complete understanding about which amino acid positions to use for such cysteine-based conjugations. In particular, no information has yet been available about conjugates of amatoxins and antibodies via engineered cysteine residues. However, in light of the high toxicity of amatoxins, it is enormously important to identify constructs that display a high toxicity against the target cell of interest, while simultaneously showing excellent stability and tolerability. So far, this goal has not yet been achieved.

OBJECT OF THE INVENTION

Thus, there was still a great need for a cost-efficient and robust way of synthesizing conjugates comprising amatoxins and antibodies, in particular amatoxins linked to antibodies comprising specific cysteine residues, which conjugates are highly toxic towards target cells and simultaneously stable and highly tolerable. It was furthermore an object of the present invention to identify positions in antibody chains that can be mutated from a parental amino acid residue to a cysteine residue, which result in the formation of such highly toxic, stable and highly tolerable conjugates.

SUMMARY OF THE INVENTION

The present invention is based on the unexpected observation that a limited number of specific wild-type amino acid residues can be identified, which can be mutated to single, unpaired cysteine residues, which result in the formation of highly toxic, stable and highly tolerable conjugates with amatoxins.

Thus, in one aspect the present invention relates to a conjugate of generic formula:

Ama-L-X—S-Ab, wherein Ama is an amatoxin, L is a linker, X is a moiety resulting from coupling of a thiol group to a thiol-reactive group, S is the sulphur atom of a cysteine amino acid residue, and Ab is an antibody sequence, or a functional antibody fragment, comprising said cysteine residue, wherein said cysteine residue (i) is located in an antibody domain selected from CL, CH1, CH2, and CH3; (ii) is located at a position, where the germline sequence exhibiting the closest homology to the sequence of said antibody domain contains an amino acid residue different from cysteine; and (iii) is located a position that is solvent-exposed.

In another aspect, the present invention relates to a conjugate of generic formula:

Ama-L-X—S-Ab, wherein Ama is an amatoxin, L is a linker, X is a moiety resulting from coupling of a thiol group to a thiol-reactive group, S is the sulphur atom of a cysteine amino acid residue, and Ab is an antibody sequence, or a functional antibody fragment, comprising said cysteine residue, wherein said cysteine residue is selected from the list of heavy chain 118Cys, heavy chain 239Cys, and heavy chain 265Cys, in particular: heavy chain 118Cys, and heavy chain 265Cys.

In a third aspect, the present invention relates to a method for synthesizing a conjugate of generic formula:

Ama-L-X—S-Ab by reacting a compound Ama-L-X', wherein X' is a thiol-reactive group, with an antibody Ab-SH, wherein the group —SH is a thiol of a cysteine amino acid residue, and Ab is an antibody sequence comprising said cysteine residue, wherein said cysteine residue is selected from the list of: heavy chain 118Cys, heavy chain 239Cys, and heavy chain 265Cys, in particular: heavy chain 118Cys, and heavy chain 265Cys In a fourth aspect, the present invention relates to a kit comprising (i) a compound Ama-L-X', wherein X' is a thiol-reactive group, and (ii) an antibody Ab —SH, wherein the group —SH is a thiol of a cysteine amino acid residue, and Ab is an antibody sequence comprising said cysteine residue, wherein said cysteine residue is selected from the list of: heavy chain 118Cys, heavy chain 239Cys, and heavy chain 265Cys, in particular: heavy chain 118Cys, and heavy chain 265Cys In a fifth aspect, the present invention relates to a method for synthesizing the compound Ama-L-X', wherein X' is a maleimide group comprising the step of (a) reacting an amatoxin comprising a nucleophilic group with a compound Y-L-X" wherein Y is a leaving group, and X" is a protected maleimide group.

In a sixth aspect, the present invention relates to a pharmaceutical composition comprising the conjugate according to the present invention.

In a seventh aspect, the present invention relates to a method of treating a disease associated with cells presenting a target, comprising the step of: contacting said cells with a conjugate according to the present invention, wherein said antibody is specific for said target.

BRIEF DESCRIPTION OF THE DRAWING

FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters α to γ, Greek letters α to δ, and numbers from 1' to 7', respectively).

FIG. 2 shows a schematic view of an IgG1 molecule and the positions of the amino acid residues that have been mutated to cysteine residues and for toxin coupling.HC-A118C; HC-S131C; HC-S239C; HC-D265C; HC-E269C; HC-N297C; HC-A327C; HC-I332C; residues HC-D265 and HC-N297 are involved in Fc γ receptor binding; substitution will interfere with receptor binding and subsequent uptake in receptor-positive cells.

FIG. 3 shows a schematic view of the expression vectors for production of Trastuzumab heavy and light chains according to Example 1.

FIG. 4A shows deconvoluted mass spectra of antibody trastuzumab HC-A118C and its conjugate: (first spectrum graph) Deconvoluted mass spectrum of antibody trastuzumab HC-A118C; (second spectrum graph) Deconvoluted mass spectrum of ADC trastuzumab HC-A118C-30.0880; FIG. 4B shows deconvoluted mass spectra of antibody trastuzumab HC-A118C light chain (first spectrum graph) and heavy chain (second spectrum graph); FIG. 4C shows deconvoluted mass spectra of ADC trastuzumab HC-A118C-30.0880 light chain (first spectrum graph) and heavy chain (second spectrum graph).

FIG. 5A shows a mass spectrum of intact Her-30.0643 determined by LC/MS: drug-antibody ratio=3.7 amatoxins per IgG; FIG. 5B shows the mass spectra of light chain of Her-30.0643 determined by LC/MS; FIG. 5C shows mass spectra of heavy chain of Her-30.0643 determined by LC/MS.

FIG. 6 shows binding of four exemplary cysteine mutants to the antibody-target on SKOV-3 cells in comparison to the parent antibody (two different expression products).

FIG. 7A shows the analysis of different constructs on a blotting membrane stained with an anti-amanitin antibody: lanes 1 and 3: naked antibody Trastuzumab; lanes 2 and 4; antibody Trastuzumab conjugated to amanitin construct Her-30.0643 via lysine coupling; lane 5: naked antibody Trastuzumab with HC-A118C mutation; lane 6; antibody Trastuzumab with HC-A118C mutation conjugated to amanitin construct Her-30.1619 via cysteine coupling to 118C (bromoacetamide coupling, stable linker); lane 7: antibody Trastuzumab with HC-A118C mutation conjugated to amanitin construct Her-30.1704 via cysteine coupling to 118C (bromoacetamide coupling, cleavable linker); lane 8: antibody Trastuzumab with HC-A118C mutation conjugated to amanitin construct Her-30.0880 via cysteine coupling to 118C (maleimide coupling, stable linker); lane 9; antibody B conjugated to amanitin construct Her-30.1699 via cysteine coupling to 118C (maleimide coupling, cleavable linker); upper gel: denaturing and reducing conditions; exposure time: 60 s; lower gel: denaturing and non-reducing conditions; exposure time: approx. 5 s; FIG. 7B shows the analysis of different constructs using (i) a Coomassie protein stain (upper half); and (ii) an anti-amanitin antibody Western blot (lower half) under denaturing and reducing conditions (left side): and denaturing and non-reducing conditions (right side).

FIGS. 8A and 8B show the results of WST-I cytotoxicity assays using Fc γ receptor-positive THP-1 cells and different conjugates with different cysteine mutants of antibody Trastuzumab: FIG. 8A: 120 h incubation time; FIG. 8B: 72 h incubation time Trastuzumab; in both Figures, the two curves in the upper-right part of the graph are from ADCs based on mutants HC-D265C and HC-N297C, i.e. from mutants of residues known to be involved in Fc γ receptor binding; the remaining graphs are from ADCs based on mutants HC-A118C; HC-S239C; HC-E269C; HC-A327C; and HC-I332C.

FIG. 9 shows the results of a tolerability study of conjugate Ab Trastuzumab HC-A118C (stable linker; maleimide coupling) in mice. BWL: body weight loss; nd*: not determined because of insufficient coupling; nd: not determined because of morbidity at lower dose; nd*: not determined because of lack of material; T HC-A118C-30.0880 shows no weight loss at 37.5 mg/kg.

FIGS. 10A-10J shows the results of a tolerability study of different amatoxin-Trastuzumab conjugates in cynomolgus monkeys: random lysine conjugation, stable linker: 0.3 mg/kg (FIG. 10A); random lysine conjugation, cleavable linker: 0.3 mg/kg (FIG. 10B); conjugate Ab Trastuzumab HC-A118C with stable linker/maleimide coupling: 0.3 mg/kg (FIG. 10C); 1.0 mg/kg (fIG. 10D); 3.0 mg/kg (FIG. 10E); 10.0 mg/kg (FIG. 10F); conjugate Ab Trastuzumab HC-D265C with stable linker/maleimide coupling: 0.3 mg/kg (FIG. 10G); 1.0 mg/kg (FIG. 10H); 3.0 mg/kg (FIG. 10I); 10.0 mg/kg (FIG. 10J).

DETAILED DESCRIPTION OF THE INVENTION

Figure 1:
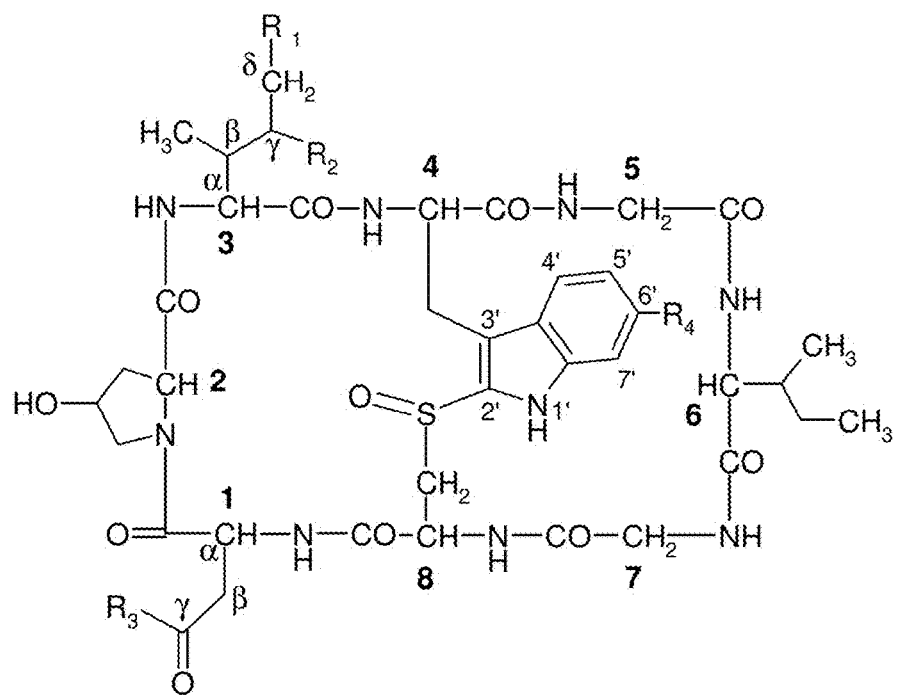

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and KaIbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer, composition or step or group of integers or steps, while any additional integer, composition or step or group of integers, compositions or steps may optionally be present as well, including embodiments, where no additional integer, composition or step or group of integers, compositions or steps are present. In such latter embodiments, the term "comprising" is used coterminous with "consisting of".

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law. Nothing herein is to be construed as an admission that the invention is not entitled to antedate such disclosure by virtue of prior invention.

The present invention is based on the unexpected observation that a limited number of specific amino acid residues can be identified in a parental antibody, which can be mutated to single, unpaired cysteine residues, which result in the formation of highly toxic, stable and highly tolerable conjugates with amatoxins.

Thus, in one aspect the present invention relates to a conjugate of generic formula:

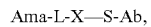

Ama-L-X—S-Ab, wherein Ama is an amatoxin, L is a linker, X is a moiety resulting from coupling of a thiol group to a thiol-reactive group, S is the sulphur atom of a cysteine amino acid residue, and Ab is an antibody sequence, or a functional antibody fragment, comprising said cysteine residue, wherein said cysteine residue (i) is located in an antibody domain selected from CL, CH1, CH2, and CH3; (ii) is located at a position, where the germline sequence exhibiting the closest homology to the sequence of said antibody domain contains an amino acid residue different from cysteine; and (iii) is located a position that is solvent-exposed.

In another aspect the present invention relates to a conjugate of generic formula:

Ama-L-X—S-Ab, wherein Ama is an amatoxin, L is a linker, X is a moiety resulting from coupling of a thiol group to a thiol-reactive group, S is the sulphur atom of a cysteine amino acid residue, and Ab is an antibody sequence, or a functional antibody fragment, comprising said cysteine residue, wherein said cysteine residue is selected from the list of heavy chain 118Cys, heavy chain 239Cys, and heavy chain 265Cys, in particular: heavy chain 118Cys, and heavy chain 265Cys.

In the context of the present invention, the term "amatoxin" includes all cyclic peptides composed of 8 amino acids as isolated from the genus Amanita and described in Wieland, T. and Faulstich H. (Wieland T, Faulstich H., CRC Crit Rev Biochem. 1978 December; 5(3):185-260), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in which the thioether sulfoxide moiety is replaced by a sulfide, sulfone, or by atoms different from sulfur, e.g. a carbon atom as in a carbaanalogue of amanitin, in each case wherein any such derivative or analogue is functionally active by inhibiting mammalian RNA polymerase II.

Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or target-binding moieties as defined above. Amatoxins which are particularly suitable for the conjugates of the present invention are α-amanitin, β-amanitin, γ-amanitin, ε-amanitin, amanin, amaninamide, amanullin and amanullinic acid as shown in FIG. 1 as well as salts, chemical derivatives, semisynthetic analogues, and synthetic analogues thereof. Particularly preferred amatoxins for use in the present invention are α-amanitin, γ-amanitin, and ε-amanitin, particularly α-amanitin.

A "linker" in the context of the present invention refers to a structure that is connecting two components, each being attached to one end of the linker. In the case of the linker being a bond, a direct linkage of amatoxin to the antibody may decrease the ability of the amatoxin to interact with RNA polymerase II. In particular embodiments, the linker, increases the distance between two components and alleviates steric interference between these components, such as in the present case between the antibody and the amatoxin. In particular embodiments, the linker has a continuous chain of between 1 and 30 atoms (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 atoms) in its backbone, i.e. the length of the linker is defined as the shortest connection as measured by the number of atoms or bonds between the amatoxin moiety and the antibody, wherein one side of the linker backbone has been reacted with the amatoxin and, the other side is available for reaction, or has been reacted, with an antibody. In the context of the present invention, a linker preferably is a $C_{1-20}$-alkylene, $C_{1-20}$-heteroalkylene, $C_{2-20}$-alkenylene, $C_{2-20}$-heteroalkenylene, $C_{2-20}$-alkynylene, $C_{2-20}$-heteroalkynylene, cycloalkylene, heterocycloalkylene, arylene, heteroarylene, aralkylene, or a heteroaralkylene group, optionally substituted. The linker may contain one or more structural elements such as carboxamide, ester, ether, thioether, disulfide, urea, thiourea, hydrocarbon moieties and the like. The linker may also contain combinations of two or more of these structural elements. Each one of these structural elements may be present in the linker more than once, e.g. twice, three times, four times, five times, or six times. In some embodiments the linker may comprise a disulfide bond. It is understood that the linker has to be attached either in a single step or in two or more subsequent steps to the amatoxin and the antibody. To that end the linker to be will carry two groups, preferably at a proximal and distal end, which can (i) form a covalent bond to a group present in one of the components to be linked, preferably an activated group on an amatoxin or the target binding-peptide or (ii) which is or can be activated to form a covalent bond with a group on an amatoxin. Accordingly, it is preferred that chemical groups are at the distal and proximal end of the linker, which are the result of such a coupling reaction, e.g. an ester, an ether, a urethane, a peptide bond etc.

In particular embodiments, the linker L is a linear chain of between 1 and 20 atoms independently selected from C, O, N and S, particularly between 2 and 18 atoms, more particularly between 5 and 16 atoms, and even more particularly between 6 and 15 atoms. In particular embodiments, at least 60% of the atoms in the linear chain are C atoms. In particular embodiments, the atoms in the linear chain are linked by single bonds.

In particular embodiments. the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, comprising from 1 to 4 heteroatoms selected from N, O, and S, wherein said linker is optionally substituted.

The term "alkylene" refers to a bivalent straight chain saturated hydrocarbon groups having from 1 to 20 carbon atoms, including groups having from 1 to 10 carbon atoms. In certain embodiments, alkylene groups may be lower alkylene groups. The term "lower alkylene" refers to alkylene groups having from 1 to 6 carbon atoms, and in certain embodiments from 1 to 5 or 1 to 4 carbon atoms. Examples of alkylene groups include, but are not limited to, methylene ($—CH_2—$), ethylene ($—CH_2—CH_2—$), n-propylene, n-butylene, n-pentylene, and n-hexylene.

The term "alkenylene" refers to bivalent straight chain groups having 2 to 20 carbon atoms, wherein at least one of the carbon-carbon bonds is a double bond, while other bonds may be single bonds or further double bonds. The term "alkynylene" herein refers to groups having 2 to 20 carbon atoms, wherein at least one of the carbon-carbon bonds is a triple bond, while other bonds may be single, double or further triple bonds. Examples of alkenylene groups include ethenylene ($—CH{=}CH—$), 1-propenylene, 2-propenylene, 1-butenylene, 2-butenylene, 3-butenylene, and the like. Examples of alkynylene groups include ethynylene, 1-propynylene, 2-propynylene, and so forth.

As used herein, "cycloalkylene" is intended to refer to a bivalent ring being part of any stable monocyclic or polycyclic system, where such ring has between 3 and 12 carbon atoms, but no heteroatom, and where such ring is fully saturated, and the term "cycloalkenylene" is intended to refer to a bivalent ring being part of any stable monocyclic or polycyclic system, where such ring has between 3 and 12 carbon atoms, but no heteroatom, and where such ring is at least partially unsaturated (but excluding any arylene ring). Examples of cycloalkylenes include, but are not limited to, cyclopropylene, cyclobutylene, cyclopentylene, cyclohexylene, and cycloheptylene. Examples of cycloalkenylenes include, but are not limited to, cyclopentenylene and cyclohexenylene.

As used herein, the terms "heterocycloalkylene" and "heterocycloalkenylene" are intended to refer to a bivalent ring being part of any stable monocyclic or polycyclic ring system, where such ring has between 3 and about 12 atoms, and where such ring consists of carbon atoms and at least one heteroatom, particularly at least one heteroatom independently selected from the group consisting of N, O and S, with heterocycloalkylene referring to such a ring that is fully saturated, and heterocycloalkenylene referring to a ring that is at least partially unsaturated (but excluding any arylene or heteroarylene ring).

The term "arylene" is intended to mean a bivalent ring or ring system being part of any stable monocyclic or polycyclic system, where such ring or ring system has between 3 and 20 carbon atoms, but has no heteroatom, which ring or ring system consists of an aromatic moiety as defined by the "4n+2" π electron rule, including phenylene.

As used herein, the term "heteroarylene" refers to a bivalent ring or ring system being part of any stable mono- or polycyclic system, where such ring or ring system has between 3 and 20 atoms, which ring or ring system consists of an aromatic moiety as defined by the "4n+2" π electron rule and contains carbon atoms and one or more nitrogen, sulfur, and/or oxygen heteroatoms.

In the context of the present invention, the term "substituted" is intended to indicate that one or more hydrogens present in the backbone of a linker is replaced with a selection from the indicated group(s), provided that the indicated atom's normal valency, or that of the appropriate atom of the group that is substituted, is not exceeded, and that the substitution results in a stable compound. The term "optionally substituted" is intended to mean that the linker is either unsubstituted or substituted, as defined herein, with one or more substituents, as defined herein. When a substituent is a keto (or oxo, i.e. =O) group, a thio or imino group or the like, then two hydrogens on the linker backbone atom are replaced. Exemplary substituents include, for example, alkyl, alkenyl, alkynyl, cycloalkyl, heterocycloalkyl, aryl, heteroaryl, aralkyl, heteroaralkyl, acyl, aroyl, heteroaroyl, carboxyl, alkoxy, aryloxy, acyloxy, aroyloxy, heteroaroyloxy, alkoxycarbonyl, halogen, (thio)ester, cyano, phosphoryl, amino, imino, (thio)amido, sulfhydryl, alkylthio, acylthio, sulfonyl, a sulfate, a sulfonate, a sulfamoyl, a sulfonamido, nitro, azido, haloalkyl, including perfluoroalkyl (such as trifluoromethyl), haloalkoxy, alkylsulfanyl, alkylsulfinyl, alkylsulfonyl, alkylsulfonylamino, arylsulfonoamino, phosphoryl, phosphate, phosphonate, phosphinate, alkylcarboxy, alkylcarboxyamide, oxo, hydroxy, mercapto, amino (optionally mono- or di-substituted, e.g. by alkyl, aryl, or heteroaryl), imino, carboxamide, carbamoyl (optionally mono- or di-substituted, e.g. by alkyl, aryl, or heteroaryl), amidino, aminosulfonyl, acylamino, aroylamino, (thio)ureido, (arylthio)ureido, alkyl(thio)ureido, cycloalkyl(thio)ureido, aryloxy, aralkoxy, or $—O(CH_2)_n—OH$, $—O(CH_2)_n—NH_2$, $—O(CH_2)_nCOOH$, $—(CH_2)_nCOOH$, $—C(O)O(CH_2)_nR$, $—(CH_2)_nN(H)C(O)OR$, or $—N(R)S(O)_2R$ wherein n is 1-4 and R is independently selected from hydrogen, -alkyl, -alkenyl, -alkynyl, -cycloalkyl, -cycloalkenyl, —(C-linked-heterocycloalkyl), —(C-linked-heterocycloalkenyl), -aryl, and -heteroaryl, with multiple degrees of substitution being allowed. It will be understood by those skilled in the art that substituents, such as heterocycloalkyl, aryl, heteroaryl, alkyl, etc., or functional groups such as —OH, —NHR etc., can themselves be substituted, if appropriate. It will also be understood by those skilled in the art that the substituted moieties themselves can be substituted as well when appropriate.

In particular embodiments, the linker L comprises a moiety selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—).

In particular embodiments of the present invention, the linker L comprises a number of m groups selected from the list of: alkylene, alkenylene, alkynylene, cycloalkylene, heteroalkylene, heteroalkenylene, heteroalkynylene, heterocycloalkylene, arylene, heteroarylene, aralkylene, and a heteroaralkylene group, wherein each group may optionally be independently substituted, the linker further comprises a number of n moieties independently selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—), wherein m=n+1. In particular embodiments, m is 2 and n is 1, or m is 3 and n is 2. In particular embodiments, the linker comprises 2 or 3 unsubstituted alkylene groups, and 1 or 2, respectively, disulfide, ether, thioether, amine, ester, carboxamide, urethane or urea moieties linking the unsubstituted alkylene groups.

In particular embodiments, the C atoms in the linear chain are independently part of optionally substituted methylene groups ($—CH_2—$). In particular such embodiments, the optional substituents are independently selected from halogen and $C_{1-6}$-alkyl, particularly methyl.

In particular embodiments, the linker L is a stable linker.

In the context of the present invention, the term "stable linker" refers to a linker that is stable (i) in the presence of enzymes, particularly of lysosomal peptidases, such as Cathepsin B, and (ii) in an intracellular reducing environment.

In particular embodiments, the stable linker does not contain (i) an enzyme-cleavable substructure, particularly no dipeptide sequence cleavable by Cathepsin B), and/or (ii) a disulfide group. In particular such embodiments, the linker has a length of up to 12 atoms, particularly from 2 to 10, more particularly from 4 to 9, and most particularly from 6 to 8 atoms.

In particular embodiments, the moiety L-X—S present in the generic formula of section [0043], is selected from the following group of moieties:

(amatoxin side) $—(CH_2)_2—X—S—$ (antibody side);
(amatoxin side) $—(CH_2)_3—X—S—$ (antibody side);
(amatoxin side) $—(CH_2)_4—X—S—$ (antibody side);
(amatoxin side) $—(CH_2)_5X—S—$ (antibody side);
(amatoxin side) $—(CH_2)_6—X—S—$ (antibody side);
(amatoxin side) $—(CH_2)_7—X—S—$ (antibody side);
(amatoxin side) $—(CH_2)_8—X—S—$ (antibody side);
(amatoxin side) $—(CH_2)_9—X—S—$ (antibody side);
(amatoxin side) $—(CH_2)_{10}—X—S—$ (antibody side);
(amatoxin side) $—(CH_2)_{11}—X—S—$ (antibody side);
(amatoxin side) $—(CH_2)_{12}—X—S—$ (antibody side);
(amatoxin side) $—(CH_2)_{16}—X—S—$ (antibody side);

(amatoxin side) —$(CH_2)_2$—O—$(CH_2)_2$—O—$(CH_2)_2$—X—S— (antibody side);

(amatoxin side) —$(CH_2)_2$—O—$(CH_2)_2$—O—$(CH_2)_2$—O—$(CH_2)_2$-X—S— (antibody side); and (amatoxin side) —$(CH_2)_2$—O—$(CH_2)_2$—O—$(CH_2)_2$—O—$(CH_2)_2$—O—$(CH_2)_2$—X—S— (antibody side).

In particular other embodiments, the linker is a cleavable linker.

In the context of the present invention, the term "cleavable linker" refers to a linker that is cleavable (i) by an enzyme, or (ii) in a reducing environment.

In the context of the present invention, the term "linker that is cleavable . . . by an enzyme" refers to a linker that can be cleaved by an enzyme, particularly by a lysosomal peptidase, such as Cathepsin B, resulting in the intracellular release of the toxin cargo conjugated to the targeting antibody after internalization (see Dubowchik et al., Bioconjug Chem. 13 (2002) 855-69). In particular embodiments, the cleavable linker comprises a dipeptide selected from: Phe-Lys, Val-Lys, Phe-Ala, Val-Ala, Phe-Cit and Val-Cit, particularly wherein the cleavable linker further comprises a p-aminobenzyl (PAB) spacer between the dipeptides and the amatoxin.

In particular other embodiments, the linker is a reducible linker

In the context of the present invention, the term "reducible linker" refers to a linker that can be cleaved in the intracellular reducing environment, particularly a linker that contains a disulfide groups, resulting in the intracellular release of the toxin cargo conjugated to the targeting antibody after internalization by the intracellular reducing environment (see Shen et al. (1985) J. Biol. Chem. 260, 10905-10908).

In particular other embodiments, the linker is a cleavable linker, particularly (i) a linker cleavable by an enzyme, particularly a linker comprising a dipeptide, particularly a dipeptide cleavable by Cathepsin B, or (ii) a reducible linker, particularly a linker comprising a disulfide group. In particular such embodiments, such cleavable linker has a length of up to 20 atoms, particularly from 6 to 18, more particularly from 8 to 16, and most particularly from 10 to 15 atoms.

In particular embodiments, the linker L in the moiety L-X—S present in the generic formula of section [0043], is selected from the following group of moieties:

(amatoxin side) —$(CH_2)_2$—S—S—$(CH_2)_2$—X—S— (antibody side);

(amatoxin side) —$(CH_2)_3$—S—S—$(CH_2)_2$—X—S— (antibody side);

(amatoxin side) —$(CH_2)_2$—S—S—$(CH_2)_3$—X—S— (antibody side);

(amatoxin side) —$(CH_2)_3$—S—S—$(CH_2)_3$—X—S— (antibody side);

(amatoxin side) —$(CH_2)_4$—S—S—$(CH_2)_4$—X—S— (antibody side);

(amatoxin side) —$(CH_2)_2$—$CMe_2$—S—S—$(CH_2)_2$—X—S— (antibody side);

(amatoxin side) —$(CH_2)_2$—S—S-$GMe_2$—$(CH_2)_2$—X—S— (antibody side);

(amatoxin side) —$(CH_2)_3$—S—S— (antibody side);

(amatoxin side) —$CH_2$—$C_6H_4$—NH-Cit-Val-CO $(CH_2)_5$—X—S— (antibody side)

(amatoxin side) —$CH_2$—$C_6H_4$—NH-Ala-Val-CO $(CH_2)_5$—X—S— (antibody side);

(amatoxin side) —$CH_2$—$C_6H_4$—NH-Ala-Val-CO $(CH_2)_2$—X—S— (antibody side);

(amatoxin side) —$CH_2$—$C_6H_4$—NH-Ala-Phe-CO $(CH_2)_2$—X—S— (antibody side);

(amatoxin side) —$CH_2$—$C_6H_4$—NH-Lys-Phe-CO $(CH_2)_2$—X—S— (antibody side);

(amatoxin side) —$CH_2$—$C_6H_4$—NH-Cit-Phe-CO $(CH_2)_2$—X—S— (antibody side);

(amatoxin side) —$CH_2$—$C_6H_4$—NH-Val-Val-CO $(CH_2)_2$—X—S— (antibody side);

(amatoxin side) —$CH_2$—$C_6H_4$—NH-Ile-Val-CO $(CH_2)_2$—X—S— (antibody side);

(amatoxin side) —$CH_2$—$C_6H_4$—NH-His-Val-CO $(CH_2)_2$—X—S— (antibody side);

(amatoxin side) —$CH_2$—$C_6H_4$—NH-Met-Val-CO $(CH_2)_2$—X—S— (antibody side);

(amatoxin side) —$CH_2$—$C_6H_4$—NH-Asn-Lys-CO $(CH_2)_2$—X—S— (antibody side); and wherein —NH— and —CO— flanking the dipeptide sequences represent amino and carbonyl moieties of the linker forming amide bonds to the carboxy- and the amino-terminus of the dipeptide, respectively.

In the context of the present invention, the term "a moiety resulting from coupling of a thiol group to a thiol-reactive group" refers to a structure that results from (i) the nucleophilic substitution of a leaving group Y present in a thiol-reactive group by the sulphur atom of a cysteine residue, for example a bromo acetamide group, a iodo acetamide, a 4,6-dichloro-1,3,5-triazin-2-ylamino group, an alkylsulfone or a heteroarylsulfone; (ii) the addition of the HS-group of a cysteine residue to an activated double bond of a thiol-reactive group, for example maleimide, or (iii) an disulfide exchange of an activated disulfide or methanethiosulfonate with the sulphur atom of a cysteine residue, for example with pyridine-2-thiol, 5-nitropyridine-2-thiol or methanesulfinate as leaving group; or (iv) any other chemical reaction that results in a stable bond between the sulphur atom of a cysteine residue and a reactive moiety being part of the thiol-reactive group.

The primary moiety resulting from coupling of thiol group may be optionally further derivatized, e.g. the succinimidyl thioether resulting from a maleimide can be hydrolysed to succinamic acid thioethers of the following generic structures 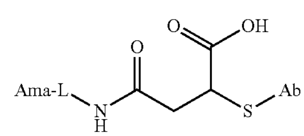 or 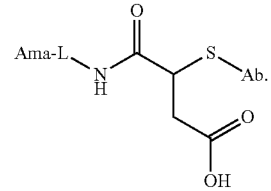 In the context of the present invention, the term "thiol-reactive group" refers to a group that selectively reacts with the thiol group of a free cysteine of an antibody, particularly in a pH value in the range between 6.0 and 8.0, more particularly in a pH value in the range between 6.5 and 7.5. In particular, the term "selectively" means that less than 10% of the coupling reactions of a molecule comprising a thiol-reactive group with an antibody comprising at least one free cysteine residue are coupling reactions with non-cysteine residues of the antibody, such as lysine residues, particularly less than 5%, more particularly less than 2%.

In particular embodiments, the moiety resulting from coupling of a thiol group to a thiol-reactive group is selected from: thiol-substituted acetamide; thiol-substituted succinimide; thiol-substituted succinamic acid; thiol-substituted heteroaryl, particularly thiol-substituted benzothiazole, thiol-substituted phenyltetrazole and thiol-substituted phenyloxadiazole; and a disulphide, wherein one sulphur atom is derived from a cysteine residue of the antibody. In particular embodiments, the moiety resulting from coupling of a thiol group to a thiol-reactive group is a thiol-substituted succinimide.

The term "antibody, or functional antibody fragment", as used herein, refers to immunoglobulin molecules and immunologically active portions of immunoglobulin molecules, i.e. molecules that contain an antigen binding site that immunospecifically binds an antigen, i.e. antibody portions comprising at least an antigen-binding fragment of an antibody. Also comprised are immunoglobulin-like proteins that are selected through techniques including, for example, phage display to specifically bind to a target molecule, e.g. to the target protein Her-2/neu or EpCAM. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In particular embodiments, the antibody is an IgG1. "Antibodies and antigen-binding fragments thereof" suitable for use in the present invention include, but are not limited to, polyclonal, monoclonal, monovalent, bispecific, heteroconjugate, multispecific, human, humanized (in particular CDR-grafted), deimmunized, or chimeric antibodies, Fab fragments, F(ab')$_2$ fragments, fragments produced by a Fab expression library, nanobodies, anti-idiotypic (anti-Id) antibodies (including, e.g., anti-Id antibodies to antibodies of the invention), FynomAbs (Brack et al., Mol. Cancer Ther. 13 (2014) 2030), and epitope-binding fragments of any of the above, which comprise at least one of the heavy chain framework positions according to the present invention.

In some embodiments the antigen-binding fragments are human antigen-binding antibody fragments of the present invention and include, but are not limited to, Fab, Fab' and F(ab')$_2$, Fd, and other fragments comprising at least a part of an antibody heavy chain, which comprise at least one of the heavy chain framework positions according to the present invention. Such antigen-binding antibody fragments may comprise the variable domain(s) alone in combination with the entirety or a portion of the following: hinge region, CL, CH1, CH2, and CH3 domains. Also included in the invention are such antigen-binding fragments also comprising any combination of variable domain(s) with a hinge region, CL, CH1, CH2, and CH3 domains.

Antibodies usable in the invention may be from any animal origin including birds and mammals. Preferably, the antibodies are from human, rodent (e.g. mouse, rat, guinea pig, or rabbit), chicken, pig, sheep, goat, camel, cow, horse, donkey, cat, or dog origin. It is particularly preferred that the antibodies are of human or murine origin. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

As used herein, an antibody, or a functional antibody fragment, is considered to "specifically bind" to an antigen, if it has a dissociation constant $K_D$ to said antigen as target of 100 μM or less, preferably 50 μM or less, preferably 30 μM or less, preferably 20 μM or less, preferably 10 μM or less, preferably 5 μM or less, more preferably 1 μM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

In the context of the present application the terms "target molecule" and "target epitope", respectively, refers to an antigen and an epitope of an antigen, respectively, that is specifically bound by an antibody, or a functional antibody fragment. Preferably the target molecule is a tumour-associated antigen, in particular an antigen or an epitope which is present on the surface of one or more tumour cell types or tumour-associated cells in an increased concentration and/or in a different steric configuration as compared to the surface of non-tumour cells. Preferably, said antigen or epitope is present on the surface of one or more tumour or tumour stroma cell types, but not on the surface of non-tumour cells. In particular embodiments, the antibody specifically binds to an epitope of HER-2/neu or epithelial cell adhesion molecule (EpCAM). In other embodiments, said antigen or epitope is preferentially expressed on cells involved in autoimmune diseases. In particular such embodiments, the antibody specifically binds to an epitope of the IL-6 receptor (IL-6R). In other embodiments, said antigen or epitope is preferentially expressed on cells involved in an inflammatory disease.

In particular embodiments, the antibody, or functional antibody fragment, specifically binds to an epitope that is present on a tumour cell, particularly wherein the antibody specifically binds to an epitope of human epidermal growth factor receptor 2 (HER2).

In particular embodiments, the antibody is Trastuzumab or HEA125, or an antibody fragment comprising the antigen binding fragment of Trastuzumab or HEA125.

In particular embodiments, more than one amatoxin molecule is coupled to one antibody, or one functional antibody fragment. An increase of the number of amatoxins per conjugate will also increase the toxicity. However, an increase will simultaneously decrease the tolerability. Accordingly, in a particular embodiment the ratio of antibody, or functional antibody fragment, to amatoxin is between one antibody, or one functional antibody fragment, to between 1 and 4 amatoxin molecules, particularly between 1.5 and 3.5 amatoxin molecules, more particularly between 1.8 and 2.5 amatoxin molecules, more particularly about 2 amatoxin molecules. For the purpose of the calculation of the ratio in case of antibody dimers such as IgGs, the dimer is considered as one moiety.

In particular embodiments. the the antibody or the antigen-binding fragment thereof is selected from a diabody, a tetrabody, a nanobody, a chimeric antibody, a deimmunized antibody, a humanized antibody or a human antibody.

In particular embodiments. the antigen binding fragment is selected from the group consisting of Fab, F(ab')$_2$, Fd, Fv, single-chain Fv, and disulfide-linked Fvs (dsFv).

In the context of the present invention, the terms "heavy chain 118Cys", "heavy chain 239Cys", and "heavy chain 265Cys" refer to positions in the heavy chain of human IgG1 antibody sequences, wherein in numbering is the EU numbering system according to Edelman et al., Proc. Natl. Acad. Sci. USA; 63 (1969) 78-85. For example, when starting from Herceptin® (trastuzumab) as parental human IgG1 sequence, one of the following mutations will have to be made: HC-Ala118Cys; HC-Ser239Cys or HC-Asp265Cys.

In a third aspect, the present invention relates to a method for synthesizing a conjugate of generic formula:

Ama-L-X—S-Ab by reacting a compound Ama-L-X', wherein X' is a thiol-reactive group, with an antibody Ab-SH, wherein the group —SH is a thiol of a cysteine amino acid residue, and Ab is an antibody sequence comprising said cysteine residue, wherein said cysteine residue is selected from the list of: heavy chain 118Cys, heavy chain 239Cys, and heavy chain 265Cys, in particular: heavy chain 118Cys, and heavy chain 265Cys.

In a fourth aspect, the present invention relates to a kit comprising (i) a compound Ama-L-X', wherein X' is a thiol-reactive group, and (ii) an antibody Ab-SH, wherein the group —SH is a thiol of a cysteine amino acid residue, and Ab is an antibody sequence comprising said cysteine residue, wherein said cysteine residue is selected from the list of: heavy chain 118Cys, heavy chain 239Cys, and heavy chain 265Cys, in particular: heavy chain 118Cys, and heavy chain 265Cys In particular embodiments, the thiol-reactive group X' is selected from bromo acetamide, iodo acetamide, methylsulfonylbenzothiazole, 4,6-dichloro-1,3,5-triazin-2-ylamino group methylsulfonyl phenyltetrazole or methylsulfonyl phenyloxadiazole, pyridine-2-thiol, 5-nitropyridine-2-thiol, methanethiosulfonate, and a maleimide.

Thus, in particular embodiments of the present invention, X' is a maleimido substructure, wherein a nucleophilic group of the engineered cysteine residue can couple to the double bond of the maleimide.

In a fifth aspect, the present invention relates to a method for synthesizing the compound Ama-L-X', wherein X' is a maleimide group comprising the step of (a) reacting an amatoxin comprising a nucleophilic group with a compound Y-L-X" wherein Y is a leaving group, and X" is a protected maleimide group.

In a particular embodiment, the method comprises the additional step of (b) removing the protection group from X".

In a preferred embodiment, step (a) is carried out under basic condition, wherein the leaving group Y is selected from Br, I, tosylate or mesylate, and wherein X" is a stable toward basic conditions.

In a particular embodiment X" is a Diels-Alder-adduct resulting from reaction of a maleimide with a 1,3-diene. In a particular embodiment, step (b) comprises the removal of the protection group by a retro-Diels-Alder reaction.

In a more particular embodiment, X" is a Diels-Alder-adduct resulting in step (a) from reaction of a maleimide with cyclopentadiene, furan or a 2,5-dialkylfuran and wherein the deprotection step (b) is carried out in a polar aprotic solvent at elevated temperature.

Most particularly X" is the Diels-Alder exo adduct resulting in step (a) from a reaction of a maleimide with 2,5-dimethylfuran and wherein the deprotection step (b) is carried out in dimethylsulfoxide or N-methylpyrrolidone at a temperature between 80° C. and 120° C.

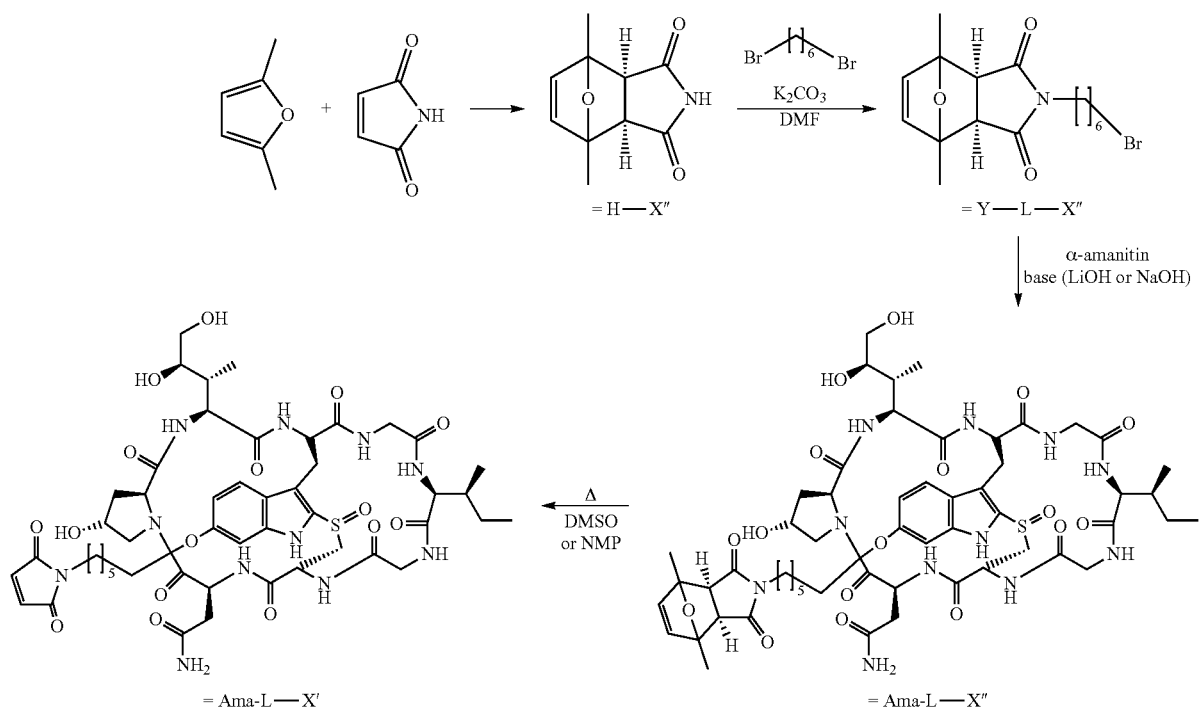

In a sixth aspect, the present invention relates to a pharmaceutical composition comprising the conjugate according to the present invention.

In another aspect the present invention relates to a conjugate of the present invention for use as a medicament.

In a seventh aspect, the present invention relates to a method of treating a disease associated with cells presenting a target, comprising the step of: contacting said cells with a conjugate according to the present invention, wherein said antibody, or said functional antibody fragment, is specific for said target.

In another aspect the present invention relates to a conjugate of the present invention for use in the treatment of a disease in a patient, particularly wherein the disease is cancer, particularly a cancer selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, leukemia, and malignant lymphoma.

As used herein, a "patient" means any mammal or bird who may benefit from a treatment with the antibody toxin conjugates described herein. Preferably, a "patient" is selected from the group consisting of laboratory animals (e.g. mouse or rat), domestic animals (including e.g. guinea pig, rabbit, chicken, pig, sheep, goat, camel, cow, horse, donkey, cat, or dog), or primates including human beings. It is particularly preferred that the "patient" is a human being.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the treatment may comprise administering a conjugate or a pharmaceutical composition according to the present invention to a patient, wherein "administering" includes in vivo administration, as well as administration directly to tissue ex vivo, such as vein grafts.

In particular embodiments, a therapeutically effective amount of the conjugate of the present invention is used.

A "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

In another aspect the present invention relates to pharmaceutical composition comprising the amatoxin according to the present invention and further comprising one or more pharmaceutically acceptable diluents, carriers, excipients, fillers, binders, lubricants, glidants, disintegrants, adsorbents; and/or preservatives.

"Pharmaceutically acceptable" means approved by a regulatory agency of the Federal or a state government or listed in the U.S. Pharmacopeia or other generally recognized pharmacopeia for use in animals, and more particularly in humans.

In particular embodiments, the pharmaceutical composition is used in the form of a systemically administered medicament. This includes parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c.), intramuscular (i.m.), intravenous (i.v.) or intracutaneous (i.c.) application. In particular, it is possible to produce the respectively suitable injection formulations as a suspension of crystals, solutions, nanoparticular or a colloid dispersed systems like, e.g. hydrosols.

Injectable formulations can further be produced as concentrates, which can be dissolved or dispersed with aqueous isotonic diluents. The infusion can also be prepared in form of isotonic solutions, fatty emulsions, liposomal formulations and micro-emulsions. Similar to injectables, infusion formulations can also be prepared in the form of concentrates for dilution. Injectable formulations can also be applied in the form of permanent infusions both in in-patient and ambulant therapy, e.g. by way of mini-pumps.

It is possible to add to parenteral drug formulations, for example, albumin, plasma, expander, surface-active substances, organic diluents, pH-influencing substances, complexing substances or polymeric substances, in particular as substances to influence the adsorption of the antibody toxin conjugates of the invention to proteins or polymers or they can also be added with the aim to reduce the adsorption of the antibody toxin conjugates of the invention to materials like injection instruments or packaging-materials, for example, plastic or glass.

The amatoxins of the present invention comprising an antibody can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if the antibody toxin conjugates of the invention are introduced in finely dispersed, dispersed and suspended form, respectively, or as a suspension of crystals in the medicament or based on the "single unit principle" if the antibody toxin conjugate of the invention is enclosed in a formulation, e.g. in a tablet or a rod which is subsequently implanted. These implants or depot medicaments in single unit and multiple unit formulations often consist of so called biodegradable polymers like e.g. polyesters of lactic acid and glycolic acid, polyether urethanes, polyamino acids, poly(meth)acrylates or polysaccharides.

Adjuvants and carriers added during the production of the pharmaceutical compositions of the present invention formulated as parenterals are preferably aqua sterilisata (sterilized water), pH value influencing substances like, e.g. organic or inorganic acids or bases as well as salts thereof, buffering substances for adjusting pH values, substances for isotonization like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatine, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilizers like e.g. EDTA.

When formulating the pharmaceutical compositions of the present invention as suspensions in a preferred embodiment thickening agents to prevent the setting of the antibody toxin conjugates of the invention or, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrene, carboxymethyl cellulose, Pluronics® or polyethylene glycol sorbit fatty acid ester. The antibody toxin conjugates of the invention can also be incorporated in liquid formulations in the form of inclusion compounds e.g. with cyclodextrins. In particular embodiments dispersing agents can be added as further adjuvants. For the production of lyophilisates scaffolding agents like mannite, dextran, saccharose, human albumin, lactose, PVP or varieties of gelatine can be used.

EXAMPLES

In the following, the invention is explained in more detail by non-limiting examples:

Example 1

Engineering of Cysteine Mutants and Coupling Conditions 1.1 Antibody Production

Figure 2:
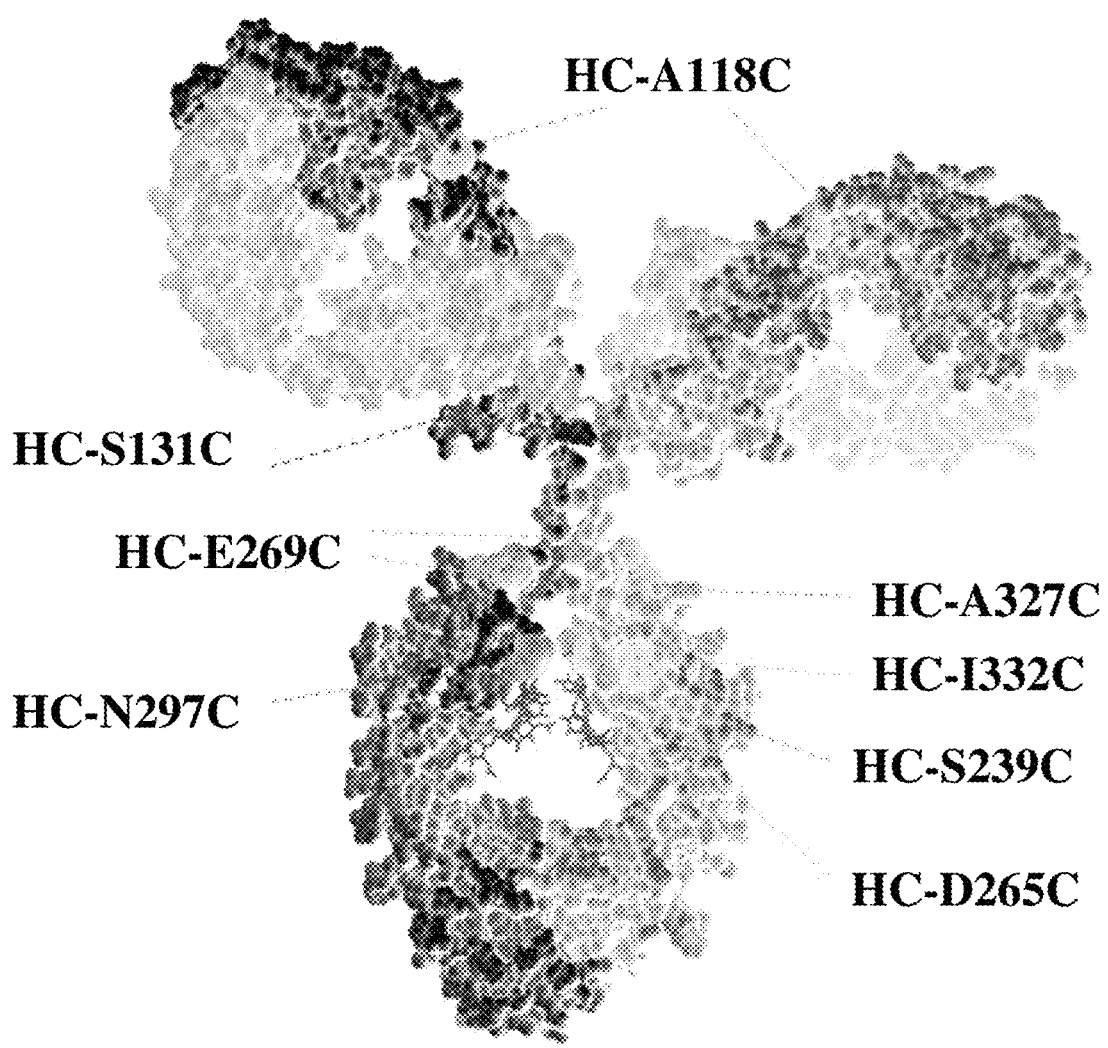
Figure 3:
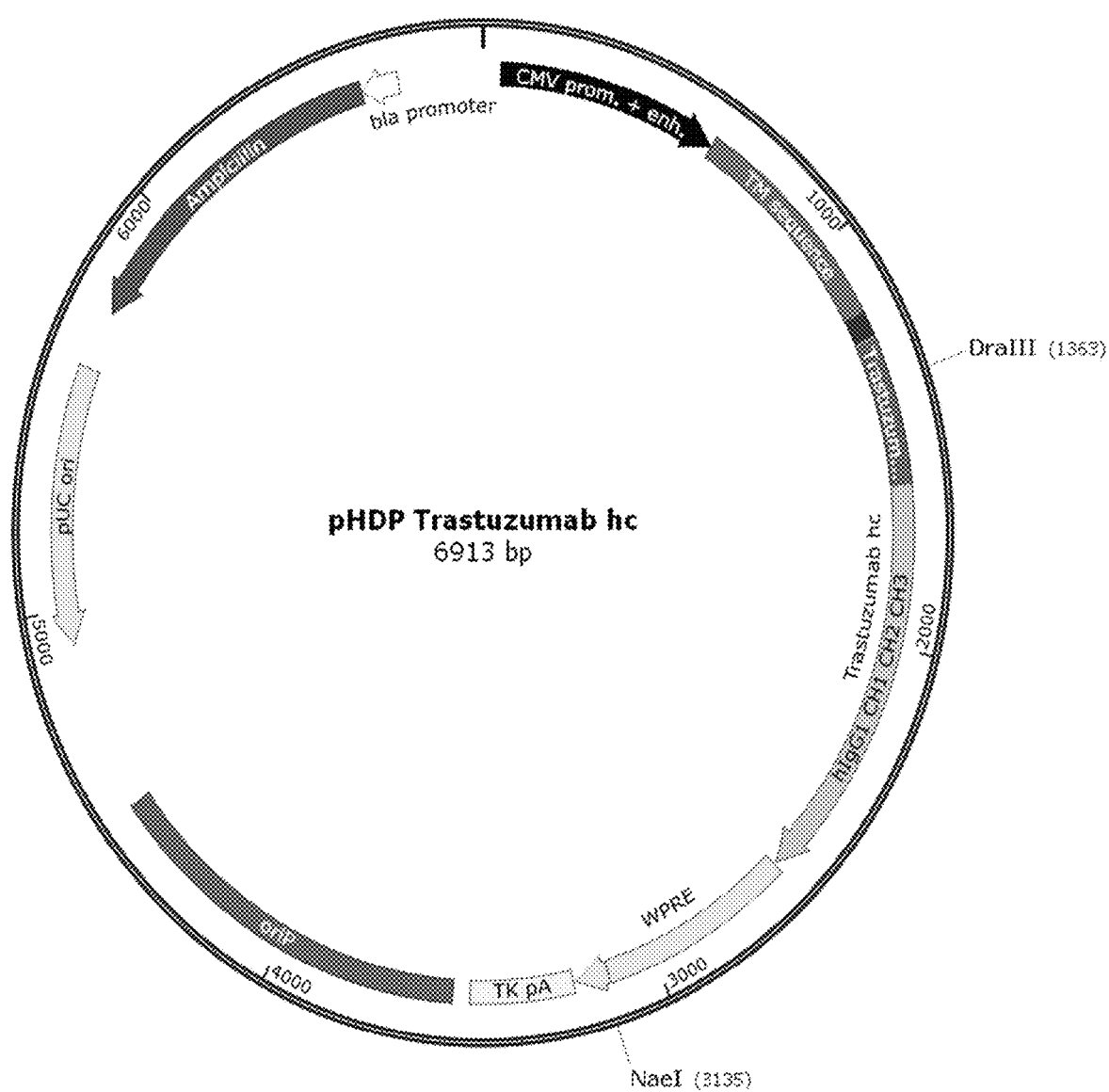
Figure 3:
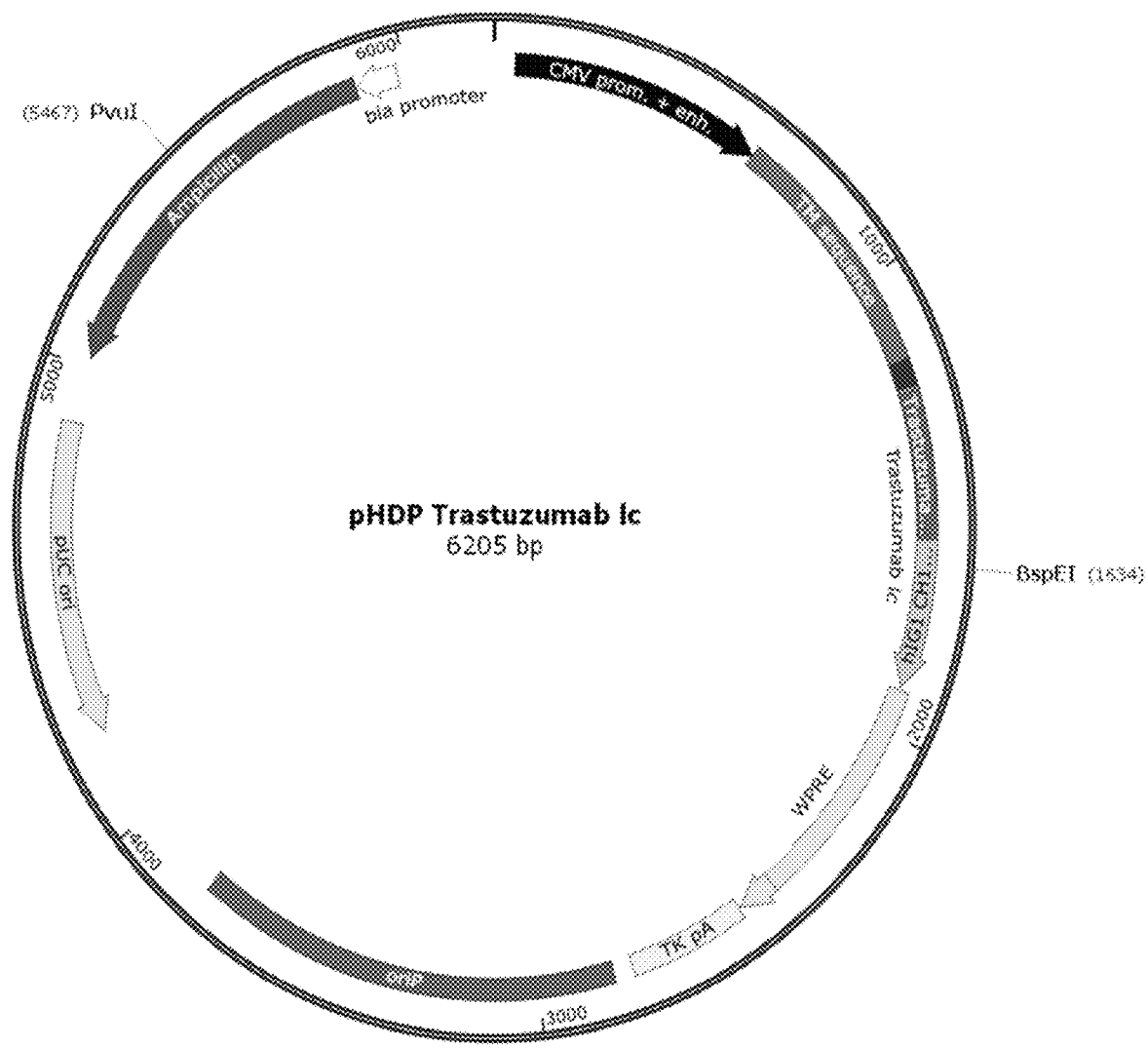

FIG. 2 shows a schematic view of an IgG1 molecule and the positions of the amino acid residues that have been mutated to cysteine residues and for toxin coupling. All antibodies were produced in eukaryotic Expi293 cells (Life Technologies) by transient transfection with expression vectors coding for heavy and light chains (FIG. 3). Gene sequences with mutations for Cys substitutions were synthesized by GeneArt and introduced into expression plasmids by standard molecular cloning methods based on endonuclease and ligase enzymes. Results from cloning experiments were verified by enzymatic restriction analysis and sequencing (GATC Biotech, Germany). For transfection, Expi293 cells were cultured in Erlenmeyer shake flasks at 125 rpm and 8% $CO_2$ to a density of ca. $3.0 \times 10^6$ cells per ml. DNA and PEI reagent complexes were produced in Opti-MEM medium with a 2:3 heavy:light chain ratio. After addition of DNA:PEI complexes to culture medium, Expi293 cells were incubated for 24 h. Cells were centrifuged at 460 g and room temperature for 15 min and culture medium was changed to ensure long-term production. Cell viability was monitored and after 4 to 6 days cells were sedimented and monoclonal antibodies were purified from supernatant by a Bio-Rad FPLC system using protein A columns (Tosoh Biosience). Aggregates and endotoxin were removed by a polishing chromatography using Superdex S-200 gelfiltration columns (GE Healthcare) using PBS, pH 7.4. Antibodies were qualified using SDS-PAGE, UV spectroscopy, analytical SEC-HPLC and endotoxin ELISA. Typical yields of purified antibodies were ca. 80-120 mg per liter culture medium with aggregates <1%.

1.2 Maleimide-Amatoxin Coupling

Figure 4A:
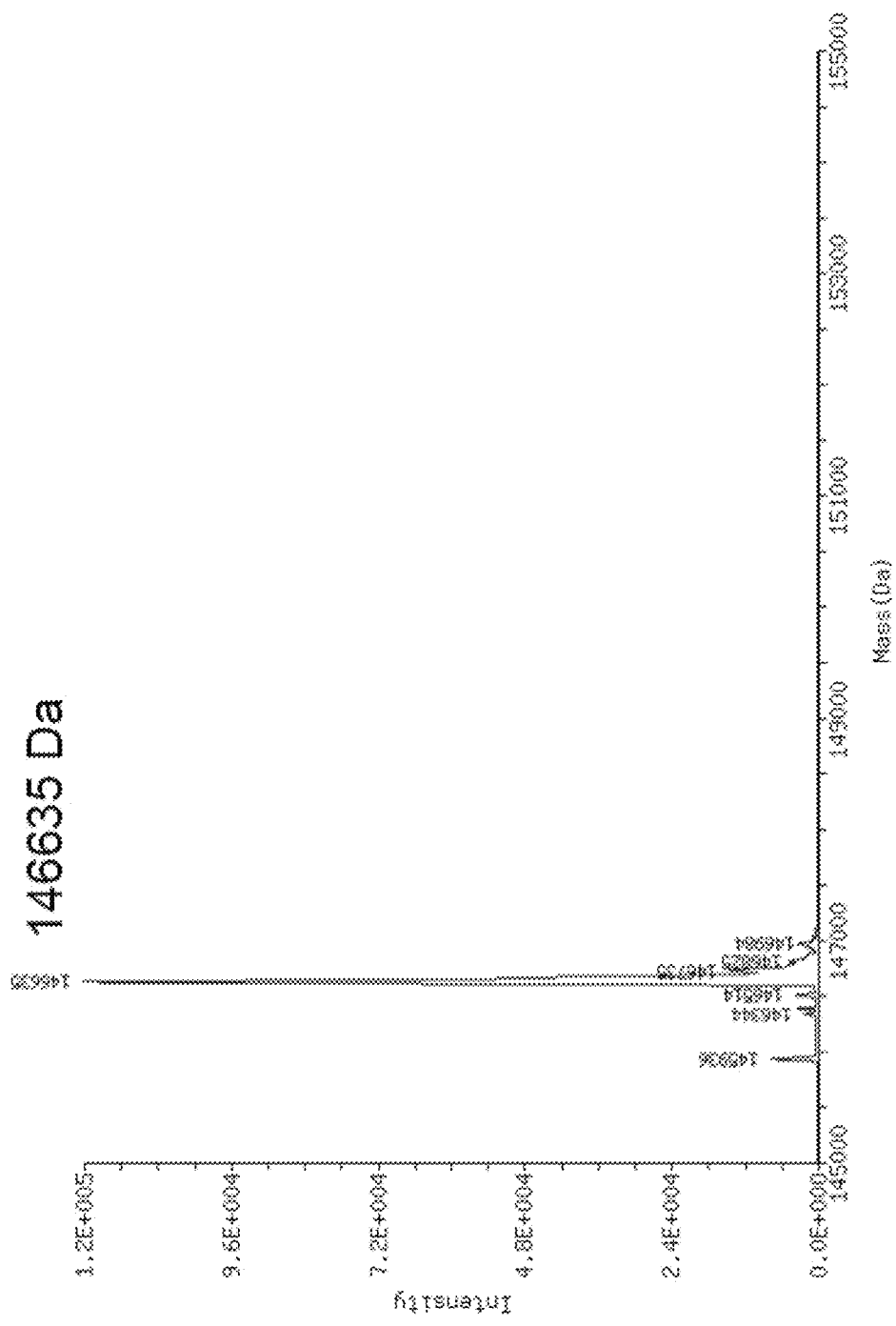
Figure 4A:
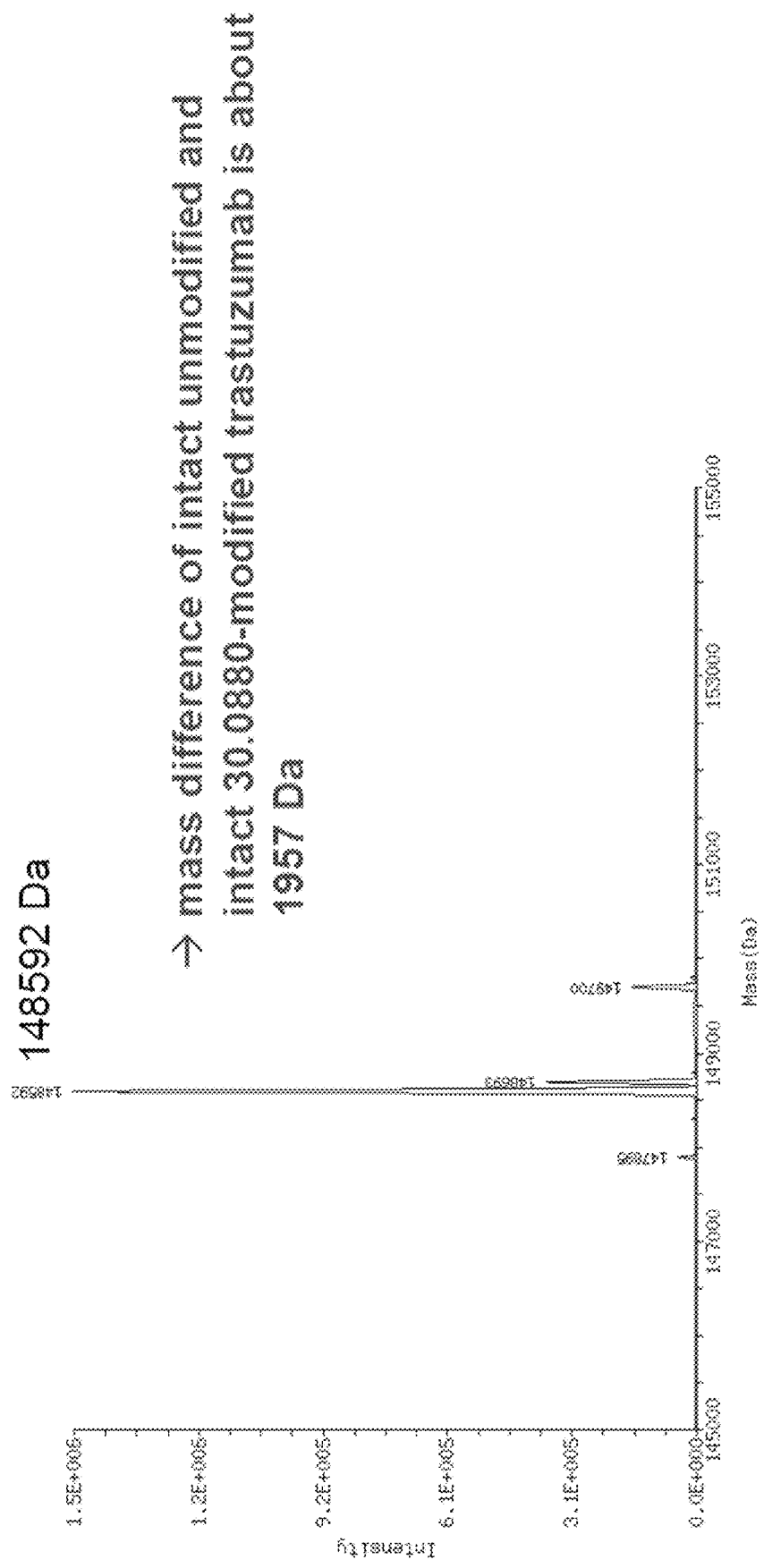
Figure 4B:
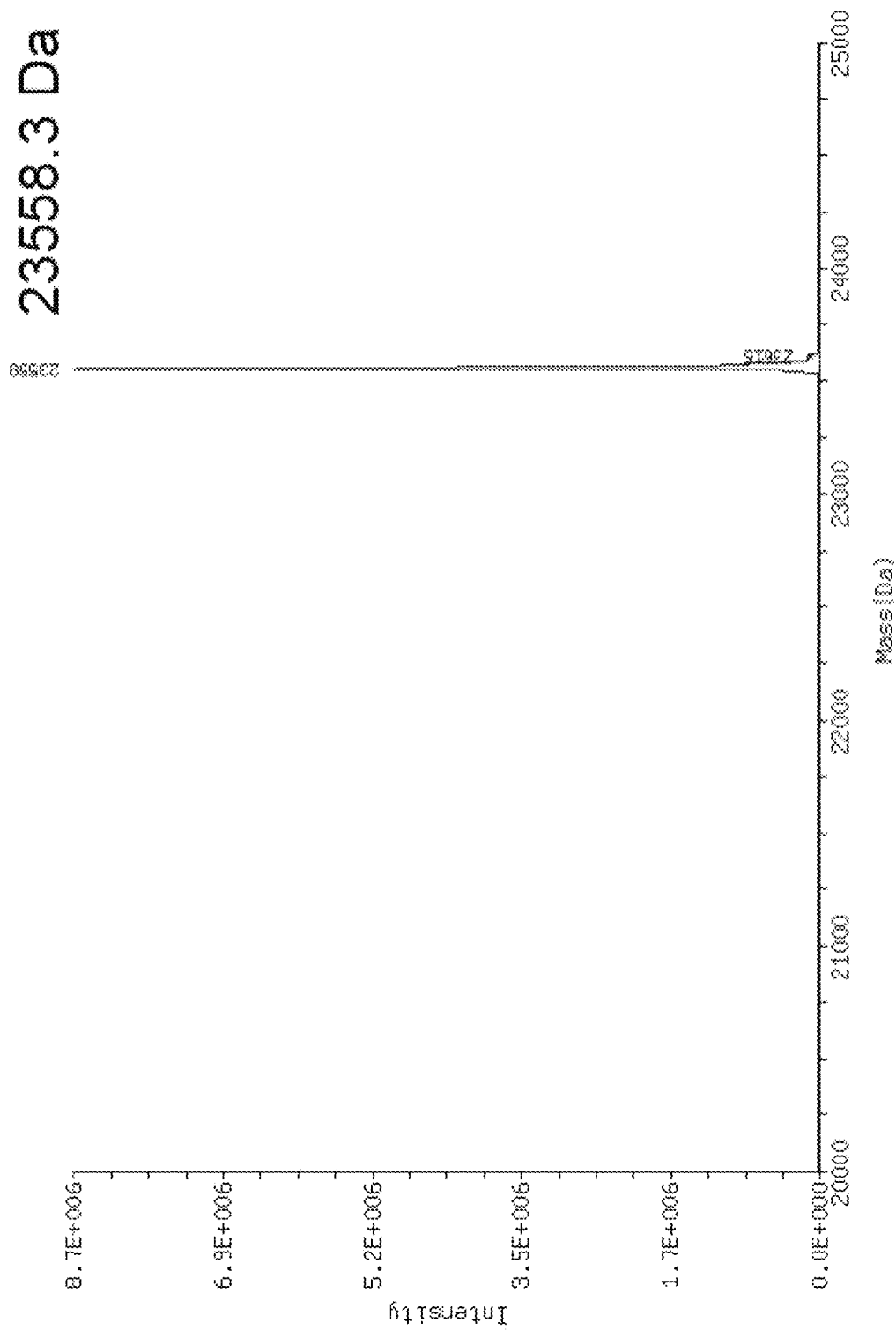
Figure 4B:
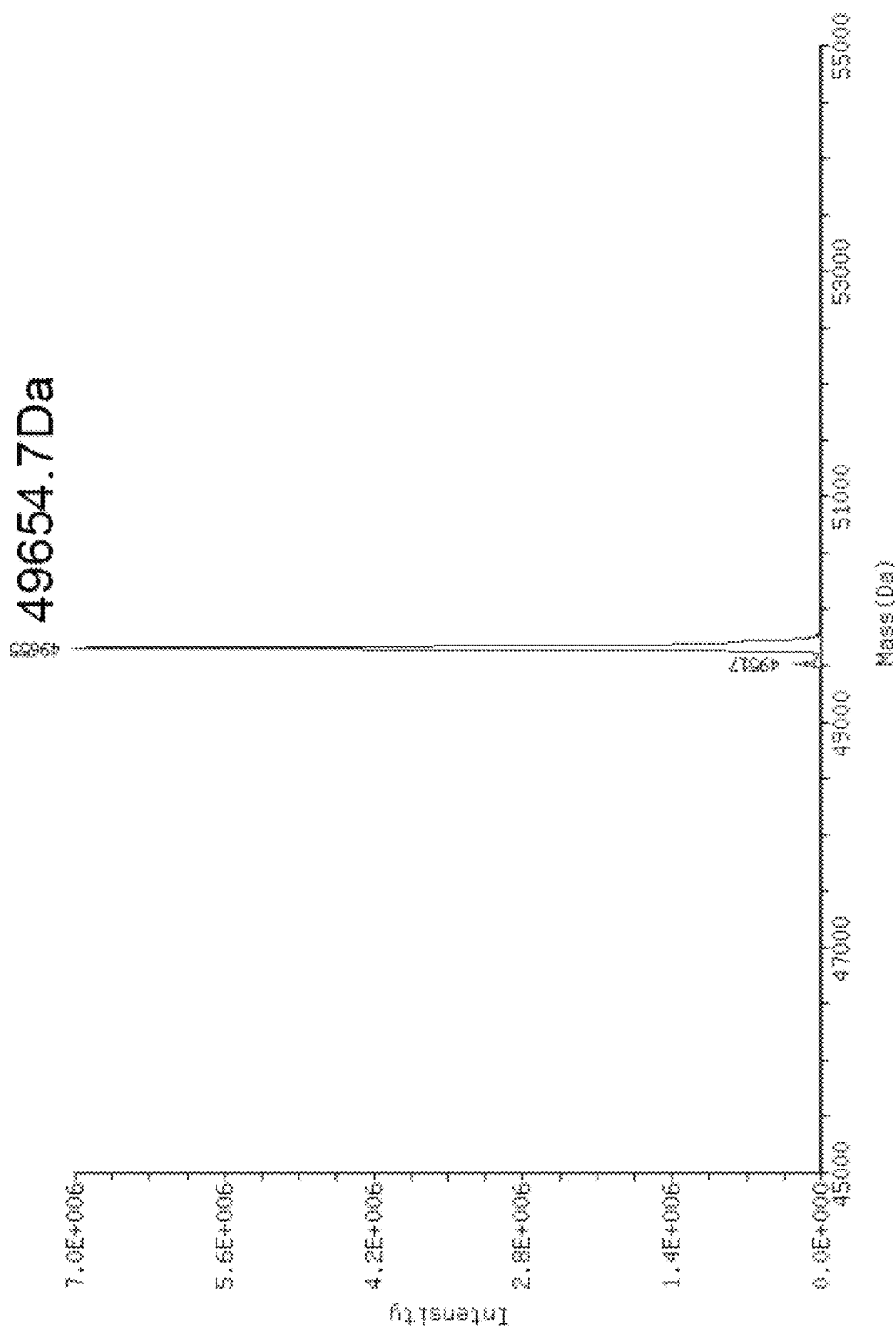
Figure 4C:
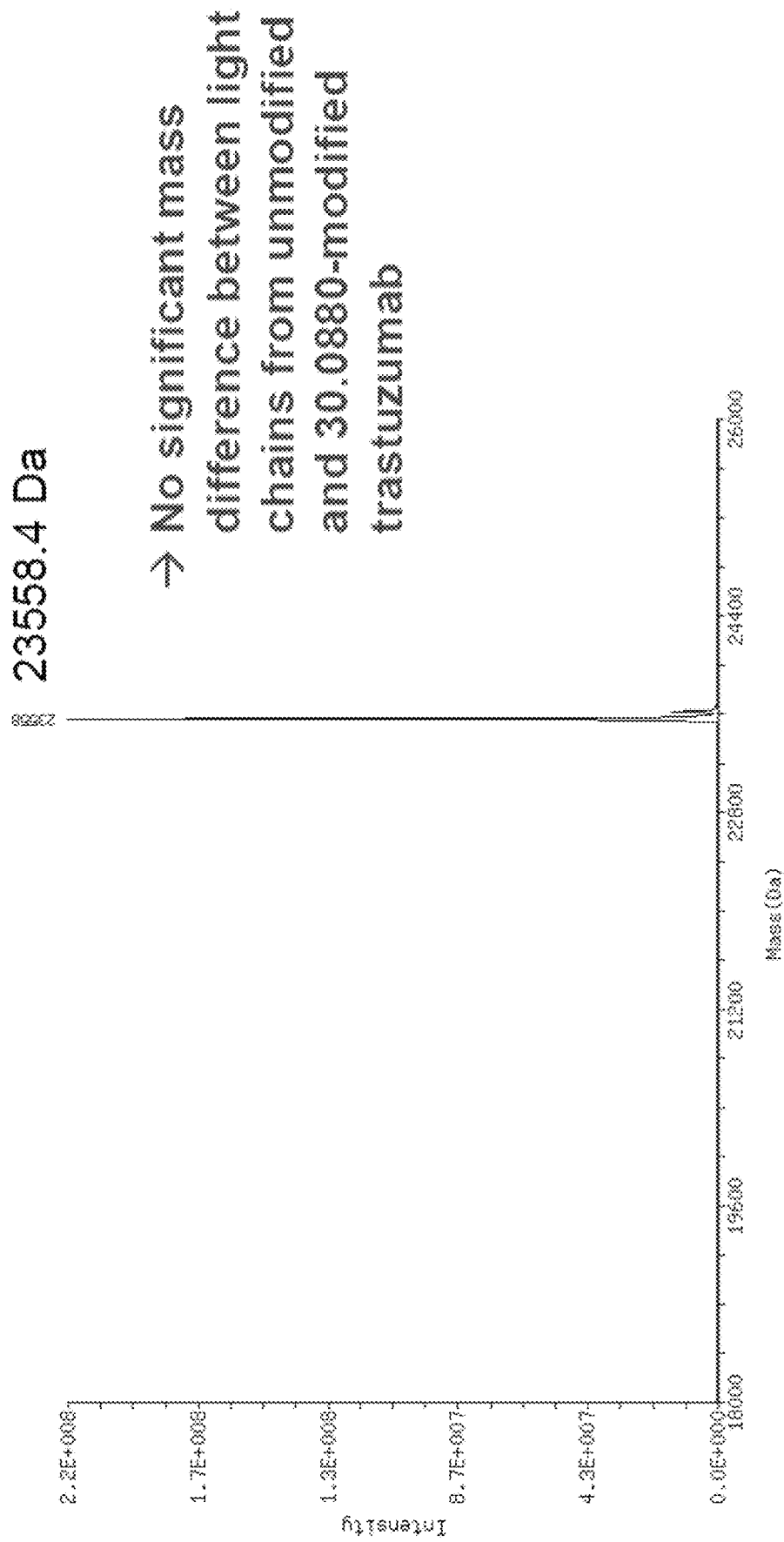
Figure 4C:
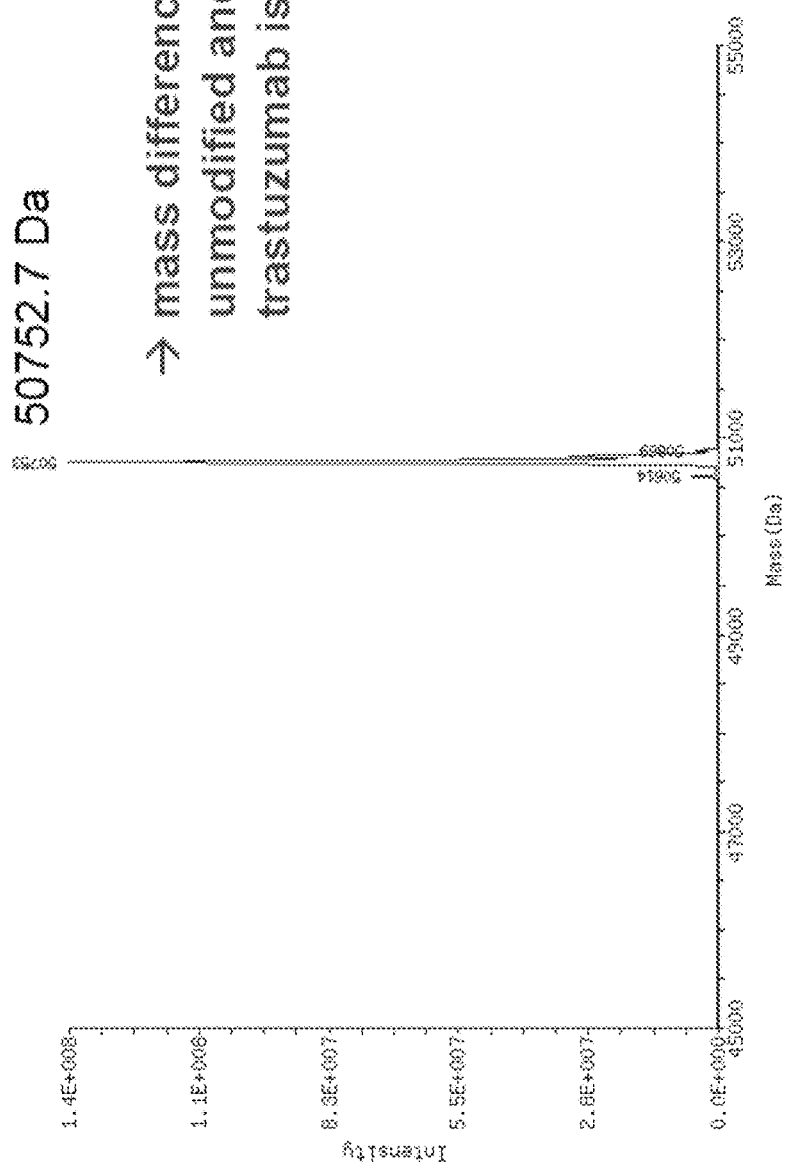
Figure 5A:
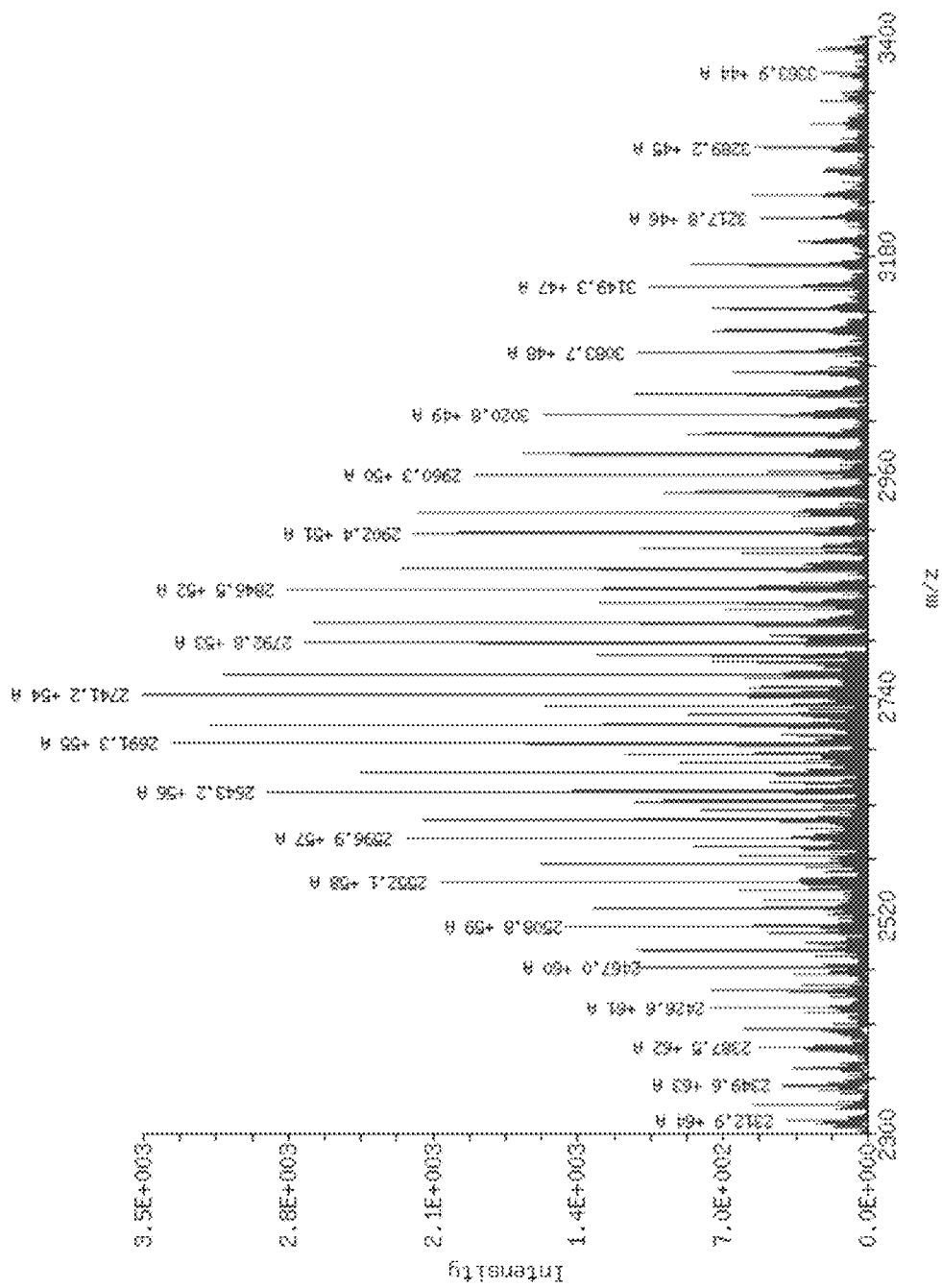
Figure 5A:
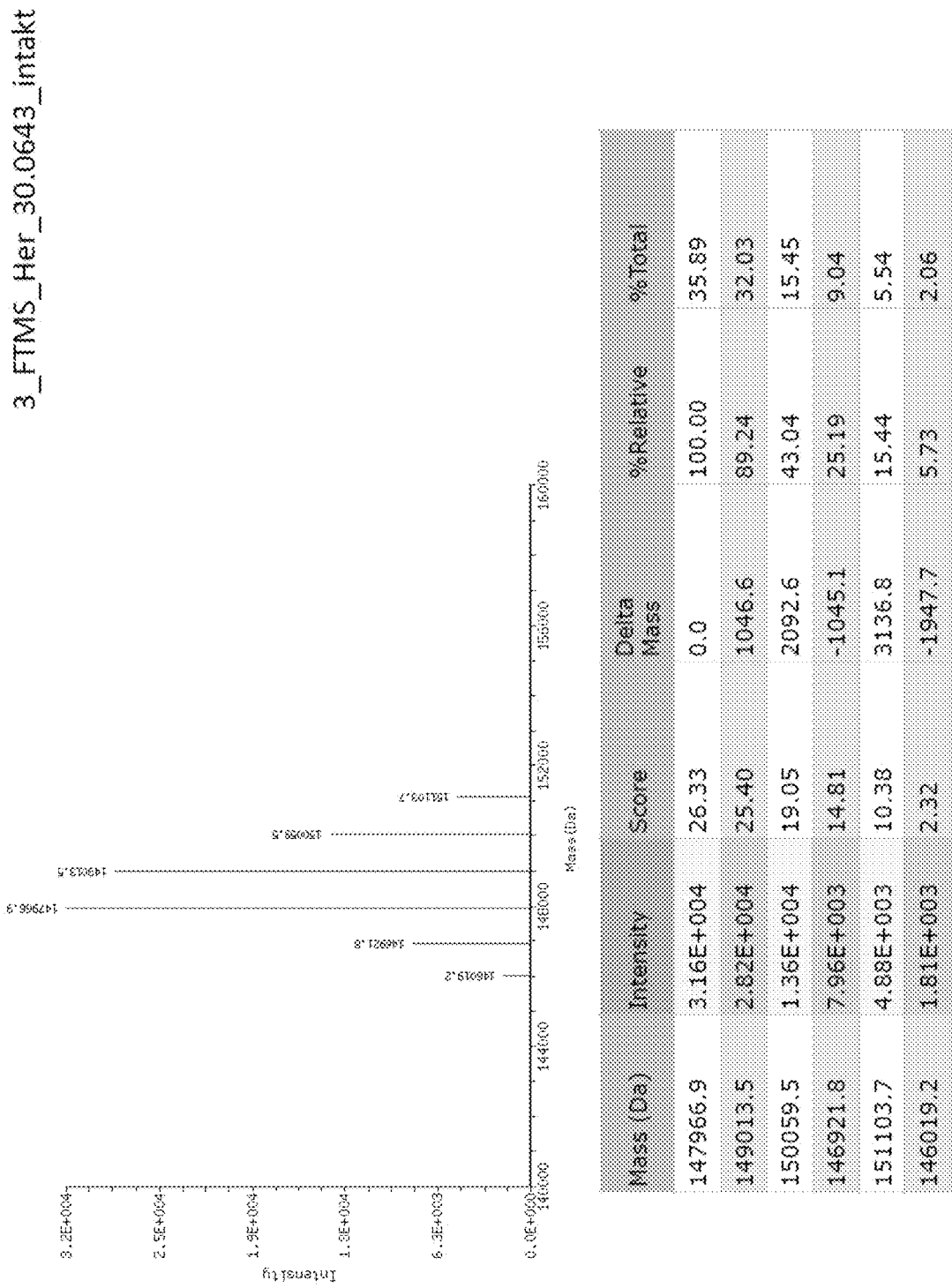
Figure 5B:
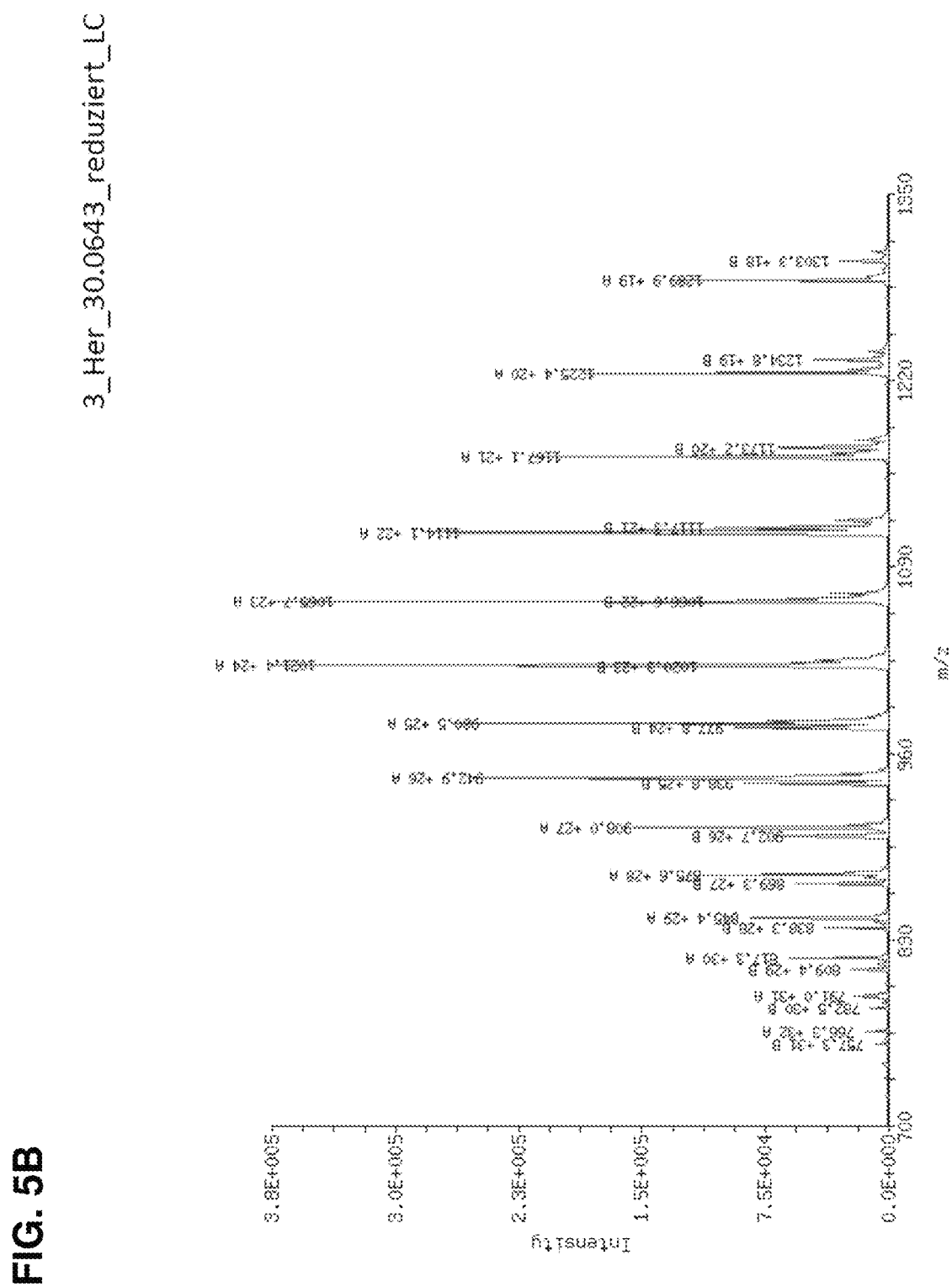
Figure 5B:
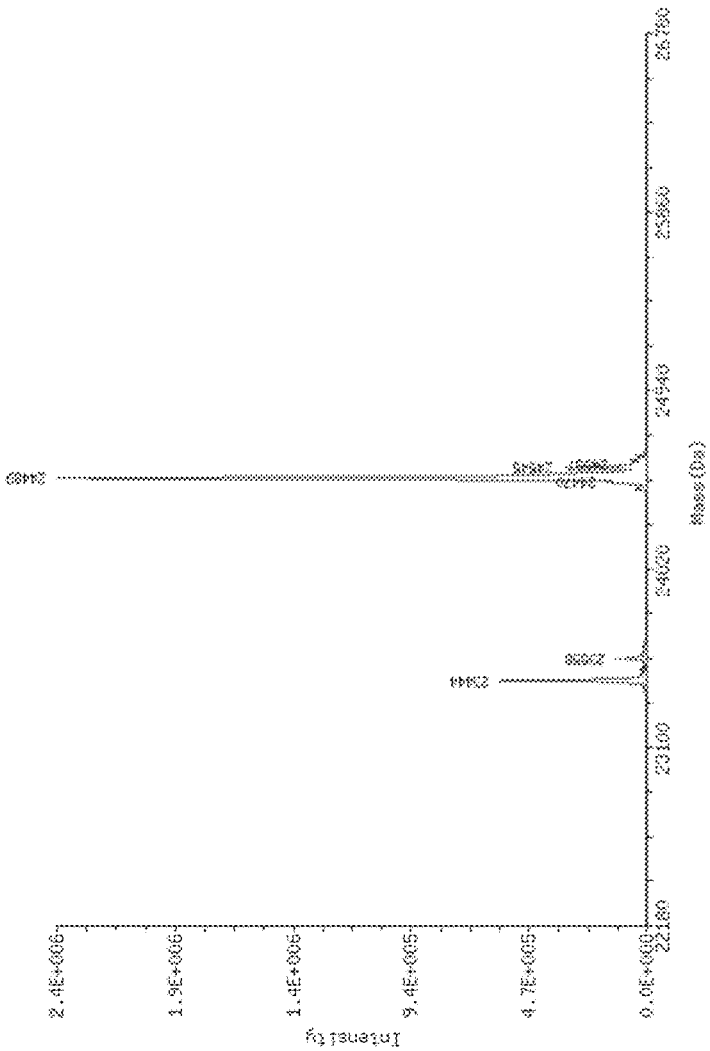
Figure 5C:
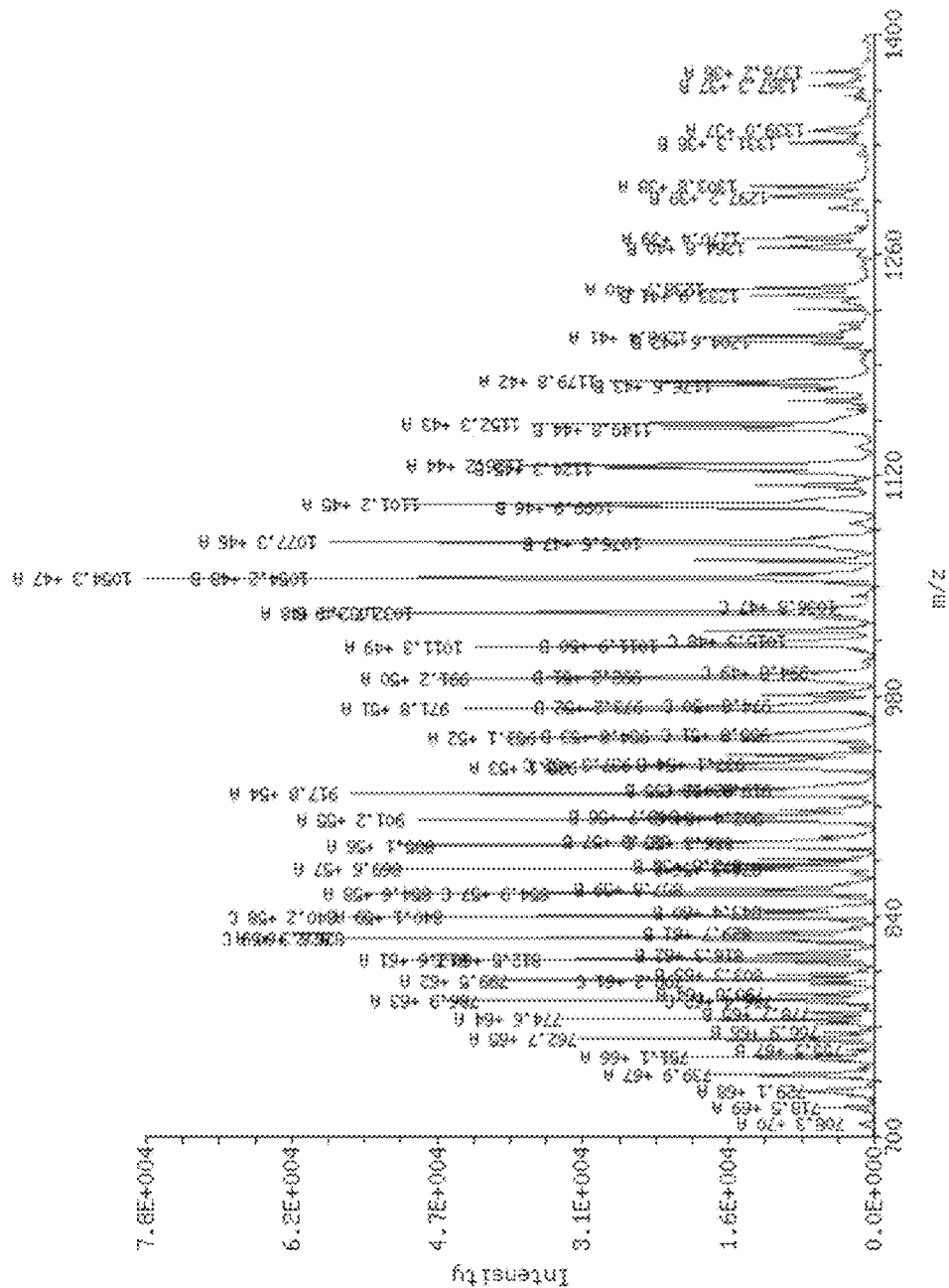
Figure 5C:
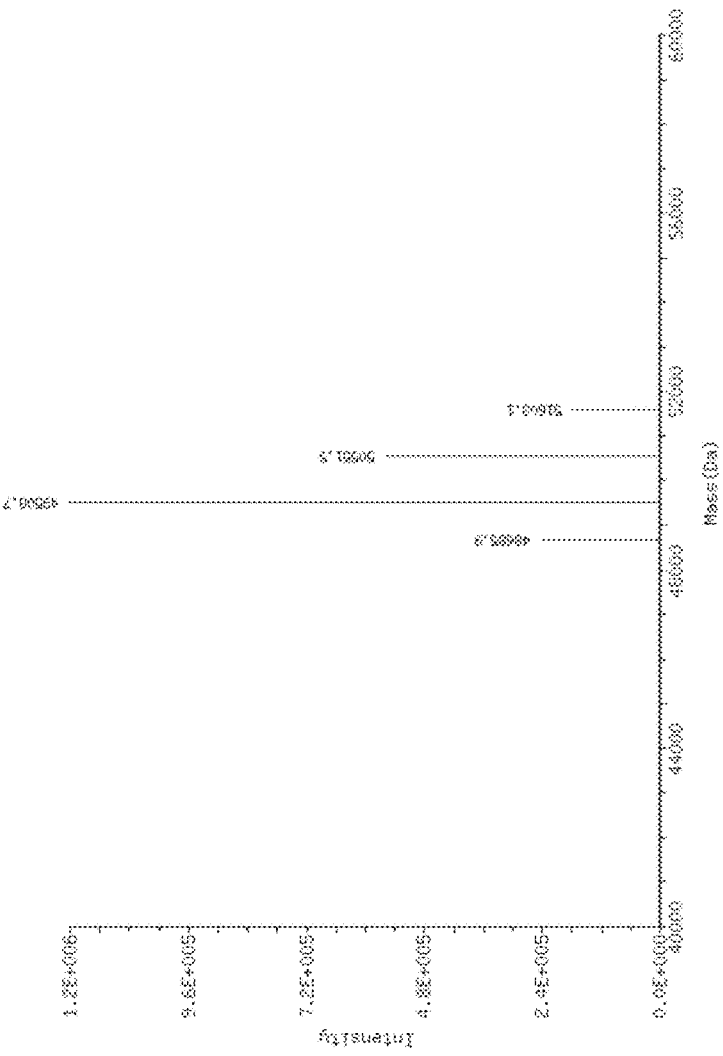

For conjugation of maleimide-amatoxin derivatives, e.g. HDP 30.0880 and HDP 30.1699, antibodies with cysteine substitutions were adjusted to 5.0 mg/ml in 1 mM EDTA in PBS, pH 7.4 and reduced by 40 eqs. of TCEP for 3 h at 37° C. Reduced antibodies were purified by two consecutive dialysis steps in 1 mM EDTA in PBS, pH 7.4 and interchain disulfides were subsequently oxidized by 20 eqs. of dehydroascorbic acid (dhAA) for 4 h at room temperature. Toxin coupling to substituted cysteines was performed by adding 8 to 15 eqs. of maleimide-amatoxin derivatives for 1 h at room temperature followed by a quenching reaction with 25 eqs. N-acetyl-L-cysteine. Amatoxin-ADCs were purified by gelfiltration chromatography using PD-10 columns or G-25 Sephadex® chromatography (GE Healthcare). Drug antibody ratios (DAR) of ADCs were determined by UV spectroscopy at 280 nm and 310 nm, using the extinction coefficients of antibodies and α-amanitin. Furthermore, DAR was determined by native LC-MS (FIG. 4A) and heavy/light chain LC-MS analysis (FIG. 4B, 4C). According to LC-MS DAR is in the range of 1.8 to 2.2 amanitins per IgG and drug is solely located to the heavy chain. Quality of ADCs was checked by SDS-PAGE, Western Blotting using anti-amanitin antiserum, analytical SEC-HPLC, HIC-HPLC and RP-HPLC. ADCs were adjusted to 3.0 to 5.0 mg/ml and stored in PBS, pH 7.4 at 4° C. until further usage with cell cultures and in vivo models.

Example 2

6'(6-N-Maleimido-hexyl)-α-amanitin (HDP 30.0880)

Step 1: 1,7-dimethyl-10-oxa-4-azatricyclo[5.2.1.0$^{2,6}$]dec-8-en-3,5-dione, exo isomer (HDP 30.0891)

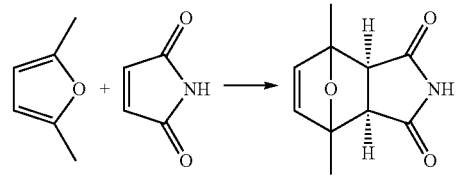

4.00 g (41.2 mmol) 2,5-dimethyl furan and 5.93 g (61.7 mmol, 1.5 eq.) maleimide were dissolved in 30 ml diethyl ether and heated to 90° C. in a Parr reactor for 12 h. the resulted precipitate was filtered off and re-crystallized from methanol: 6.62 g (83%) crystals m.p. 137° C.

$^1$H NMR (CDCl$_3$, 500 MHz) δ(ppm): 8.68 (broad singlet, 1H), 6.31 (singlet, J, 2H), 2.88 (singlet, 2H), 1.73 (singlet, 6H). $^{13}$C NMR (CDCl$_3$, 100 MHz) δ(ppm): 175.04, 140.82, 87.68, 53.77, 15.76.

Step 2: 4-(6-Bromohexyl)-1,7-dimethyl-10-oxa-4-azatricyclo[5.2.1.0$^{2,6}$]dec-8-en-3,5-dione, exo isomer (HDP 30.0916)

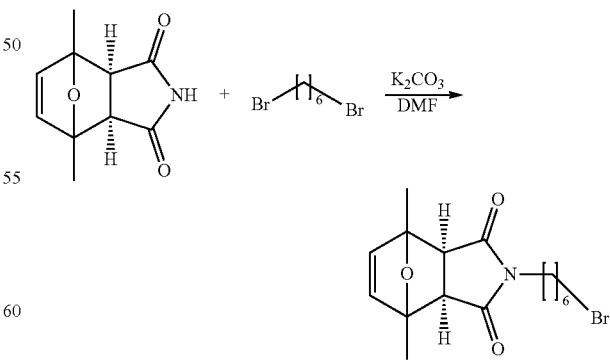

386 mg (2 mmol) HDP 30.0891 and 1.952 g (8 mmol) 1,6-dibromohexane were dissolved in 20 ml DMF, 276 mg (2 mmol) potassium carbonate were added and the suspension was heated to 50° C. for 3 h. Subsequently the DMF was evaporated, the residue was taken up with 100 ml dichloromethane. The inorganic salts were removed by filtration, kieselguhr (3 g) was added to the filtrate and the solvent removed under vacuum. The residue was purified by silica gel chromatography eluting with a gradient n-hexane—ethyl acetate to result HDP 30.0916 (483 mg) as waxy crystals in 68% yield.

$^1$H NMR (500 MHz, CDCl$_3$) δ(ppm) 6.31 (s, 2H), 3.48 (t, J=7.2 Hz, 2H), 3.39 (t, J=6.8 Hz, 2H), 2.81 (s, 1H), 1.90-1.77 (m, 2H), 1.70 (s, 5H), 1.64-1.52 (m, 2H), 1.44 (dddd, J=9.2, 7.4, 6.5, 5.4 Hz, 2H), 1.35-1.23 (m, 2H).

$^{13}$C NMR (126 MHz, CDCl$_3$) δ 174.81, 140.81, 87.52, 52.33, 38.42, 33.65, 32.50, 27.54, 27.33, 25.64, 15.87.

Step 3: 6'-(6-(1,7-dimethyl-10-oxa-4-azatricyclo[5.2.1.0$^{2,6}$]dec-8-en-3,5-dione-4-yl-hexyl)-α-amanitin (HDP 30.0903)

Under argon and at room temperature 34.5 mg (37.5 μmol) of vacuum dried α-amanitin were dissolved in 1000 μl dry dimethyl sulfoxide (DMSO). HDP 30.0916 (106.8 mg, 8 equivalents) and 1M sodium hydroxide (41.2 μl, 1.1 eq.) were added. After 3 h at room temperature the reaction mixture was acidified to pH=5 with 41.2 μl of a 1 M acetic acid solution in DMSO. The solvent is removed in vacuo and the residue was by preparative HPLC on a C18 column with a gradient from 5-100% methanol. The product containing fractions evaporated to 27.2 mg (59%) HDP 30.0903 as a colorless solid.

MS (ESI$^+$) 1194.17 [M+H]$^+$, 1216.10 [M+Na]$^+$

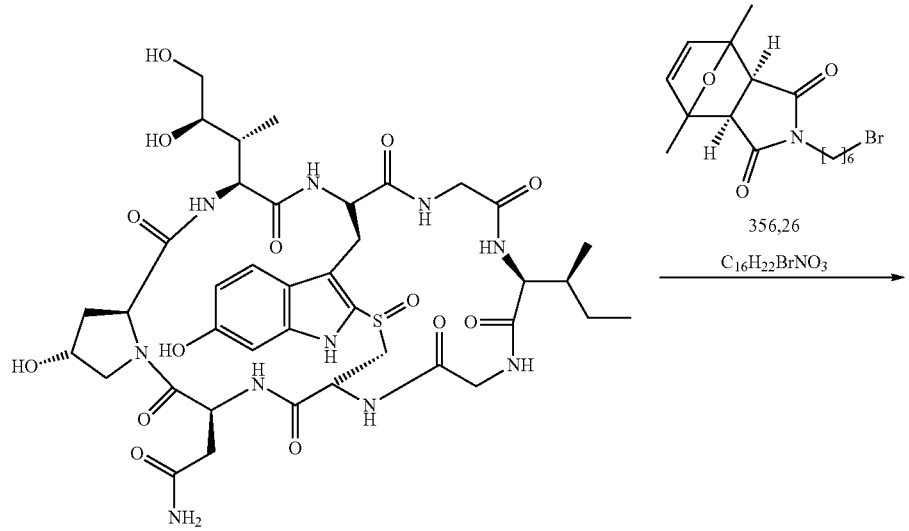

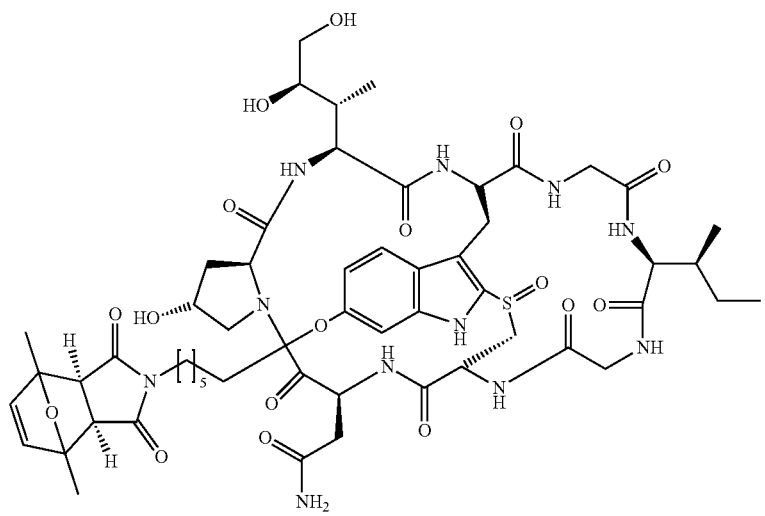

Step 4: 6'-(6-N-Maleimido-hexyl)-α-amanitin (HDP 30.0880)

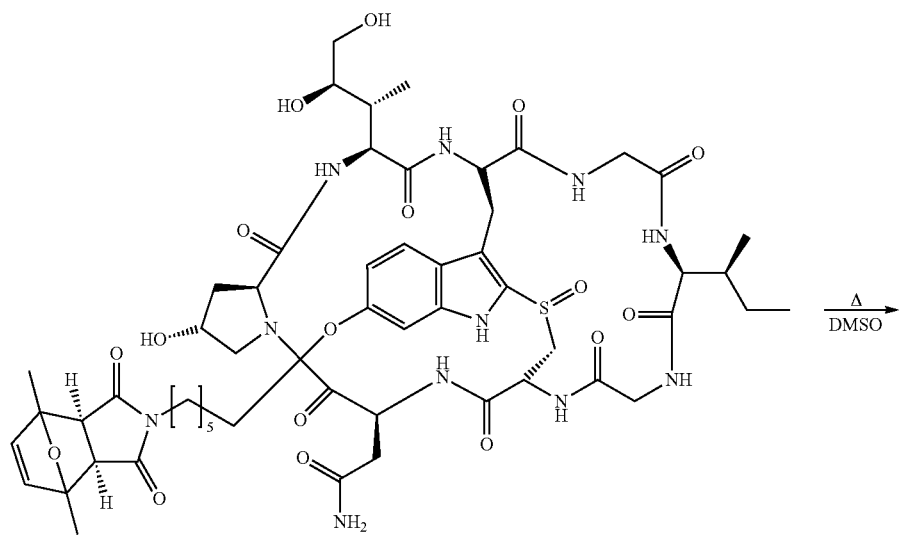

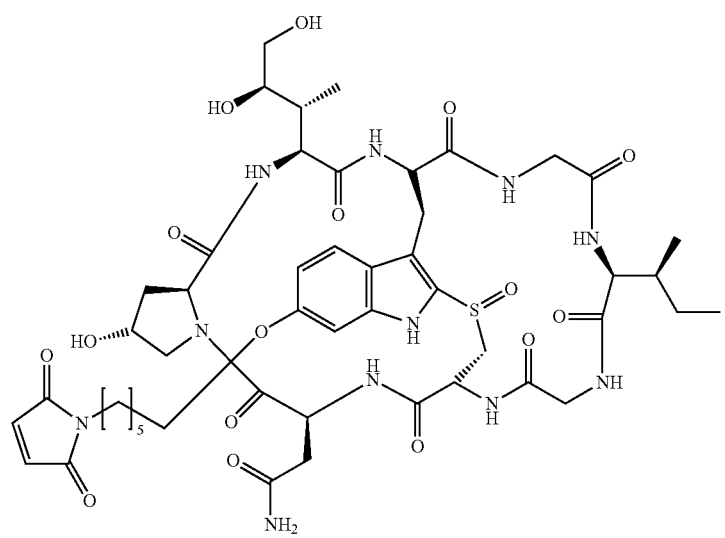

HDP 30.0903 (27.2 mg, 22.7 μmol) was dissolved in 3000 μl dry dimethylsulfoxide. The reaction mixture was heated to 100° C. with stirring for 1.5 h. After cooling to 40° C., DMSO was removed in vacuo and the residue purified by prep. HPLC with the above mentioned method.

The fraction with the retention time of 17.3-18.1 min was collected and the solvents evaporated. The residue was lyophilized from 3 ml tert-butanol to provide 23.6 mg (94%) HDP 30.0880 as off-white powder.

MS (ESI+) 1098.29 [M+H]+, 1120.36 [M+Na]+

By using the methods of example 2 with modifications obvious to the artisan the following examples were prepared:

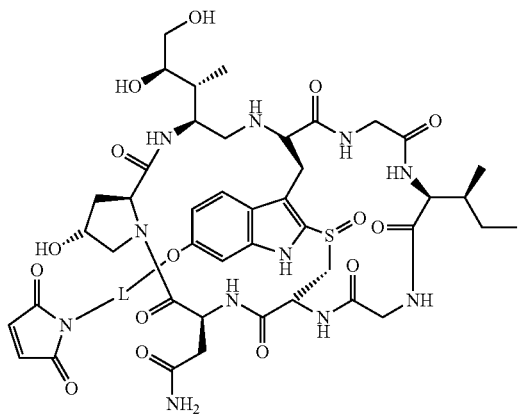

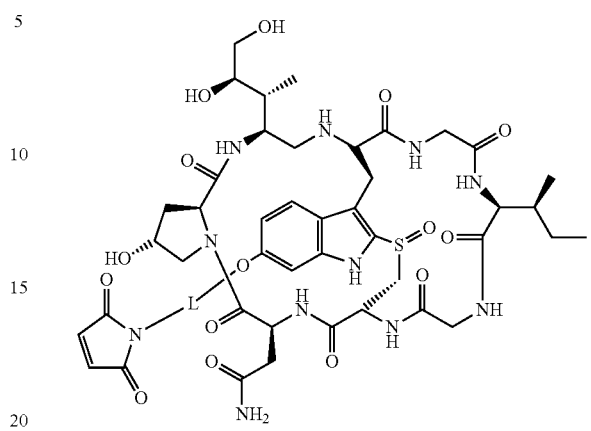

| Code | | L | m/z [MH+]calc | m/z [MH+]found |
|---|---|---|---|---|
| Example 3 | HDP 30.0933 | —(CH₂)₃— | 1056.41 (C₄₆H₆₂N₁₁O₁₆S) | 1056.21 |
| Example 4 | HDP 30.0934 | —(CH₂)₄— | 1070.43 (C₄₇H₆₄N₁₁O₁₆S) | 1070.13 |
| Example 5 | HDP 30.0935 | —(CH₂)₅— | 1084.44 (C₄₈H₆₆N₁₁O₁₆S) | 1084.18 |
| Example 6 | HDP 30.0880 | —(CH₂)₆— | 1098.46 (C₄₉H₆₈N₁₁O₁₆S) | 1098.30 |
| Example 7 | HDP 30.0936 | —(CH₂)₇— | 1112.47 (C₅₀H₇₀N₁₁O₁₆S) | 1112.09 |
| Example 8 | HDP 30.0909 | —(CH₂)₈— | 1126.49 (C₅₁H₇₂N₁₁O₁₆S) | 1126.35 |
| Example 9 | HDP 30.0937 | —(CH₂)₉— | 1140.50 (C₅₂H₇₄N₁₁O₁₆S) | 1140.33 |
| Example 10 | HDP 30.0938 | —(CH₂)₁₀— | 1154.52 (C₅₃H₇₆N₁₁O₁₆S) | 1154.19 |
| Example 11 | HDP 30.0939 | —(CH₂)₁₂— | 1182.55 (C₅₅H₈₀N₁₁O₁₆S) | 1182.19 |
| Example 12 | HDP 30.0945 | —(CH2)₂O(CH₂)₂— | 1086.42 (C₄₇H₆₄N₁₁O₁₇S) | 1086.11 |
| Example 13 | HDP 30.0946 | —[(CH2)₂O]₂(CH₂)₂— | 1130.45 (C₄₉H₆₈N₁₁O₁₈S) | 1130.13 |
| Example 14 | HDP 30.0947 | —[(CH₂)₂O]₃(CH₂)₂— | 1174.47 (C₅₁H₇₂N₁₁O₁₉S) | 1174.14 |

Example 15

6'-O-(6-(6-(N-Maleimido)-hexanamido)hexyl)-α-amanitin (HDP 30.1948)

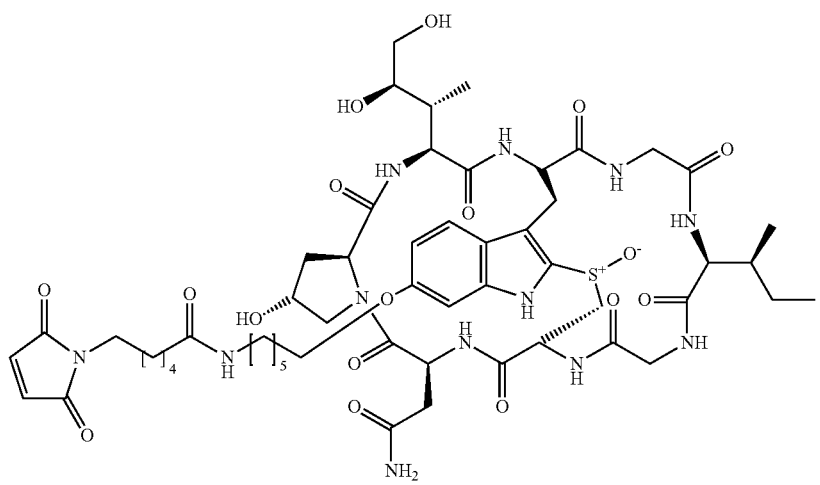

To 10.0 mg (8.83 μmol) 6'-O-(-6-aminohexyl)-α-amanitin (HDP 30.0134, synthesized as disclosed in EP 2621536), dissolved in 400 μl dry DMF were added subsequently 663 μl of 20 mM 6-(maleimido)hexanoic acid N-hydroxysuccinimide ester (EMCS) in DMF, and 17.7 μl of 1M DIPEA in DMF. After 5 h at room temperature 100 μl water was added to the reaction mixture and the volatiles were evaporated. The crude product purified by RP18 HPLC with a water-methanol gradient and the pure fractions were lyophilized from t-butanol/water: 9.02 mg (84%) HDP 30.1948 as colorless powder.

MS (ESI+) found: 1210.99; calc.: 1211.54 [MH]+ ($C_{55}H_{79}N_{12}O_{17}S$).

found: 1233.32; calc.: 1233.52 [M+Na]+ ($C_{55}H_{78}N_{12}NaO_{17}S$).

Example 16

6'-O-(6-(N-α-Maleimido)-L-2,3-diaminopropanamido)hexyl)-α-amanitin (HDP 30.1958)

Step 1: To 8.22 mg (17.66 μmol=2 eq.) Mal-L-Dap(Boc)-OH×DCHA in 700 μl DMF, and 17.7 μl of 1M DIPEA in DMF were added subsequently 9.19 mg (17.66 μmol=2 eq.) PyBop and 6.01 μl (35.33 μmol=4 eq) DIPEA. After 1 min the mixture was added to 10.0 mg (8.83 μmol) 6'-O-(-6-aminohexyl)-α-amanitin (HDP 30.0134), dissolved in 200 μl dry DMF. After 2 h at room temperature 100 μl water was added to the reaction mixture and the volatiles were evaporated. The crude product purified by RP18 HPLC and the pure fractions were evaporated: 5.45 mg (48%) HDP 30.1954 as amorphous solid.

MS (ESI+) found: 1306.58; calc.: 1306.54 [M+Na]+ ($C_{57}H_{81}N_{13}NaO_{19}S$)

Step 2: The Boc-protected Step 1 product was dissolved in 1 ml trifluoroacetic acid. After 2 min the mixture was evaporated to dryness at room temperature. The residue was purified by RP18 HPLC with a gradient of 0.05% TFA to methanol and the pure fractions were evaporated: 1.72 mg (31%) HDP 30.1958 as amorphous solid.

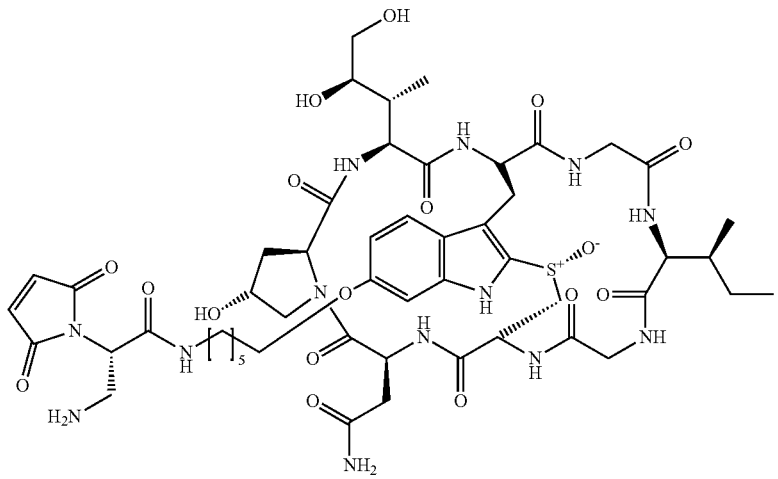

MS (ESI+) found: 1306.58; calc.: 1184.50 [M+Na]+ ($C_{52}H_{74}N_{13}O_{17}S$)

Example 17

6'-O-(2-Bromo acetamido)hexyl)-α-amanitin (HDP 30.1619)

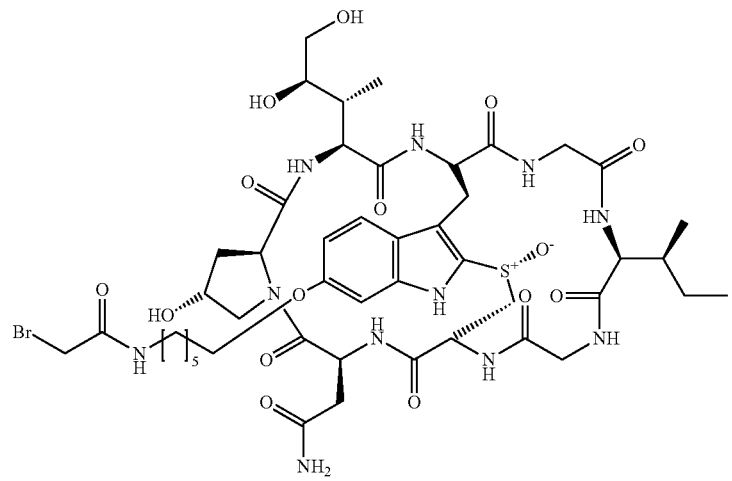

To 5.03 mg (4.44 µmol) 6'-O-(-6-aminohexyl)-α-amanitin (HDP 30.0134), dissolved in 400 µl dry DMF were added subsequently 66.6 µl of 100 mM bromoacetic acid N-hydroxysuccinimide ester in DMF, and 88.8 µl of 100 mM DIPEA in DMF. After 3 h at room temperature 50 µl water was added and the reaction mixture was dropped to 10 ml methyl tert-butylether (MTBE). The precipitate was isolated by centrifugation and washed with 10 ml MTBE. The crude product was purified by RP18 HPLC with a water-methanol gradient and the pure fractions were lyophilized from t-butanol/water: 3.70 (73%) HDP 30.1619 as colorless powder.

MS (ESI$^+$) found: 1139.58; calc.: 1138.39 [M+H]$^+$ ($C_{47}H_{69}BrN_{11}O_{15}S$).

found: 1160.42; calc.: 1160.37 [M+Na]$^+$ ($C_{47}H_{68}BrN_{11}NaO_{15}S$)).

Example 18

6'-O-(2-Bromo acetamido)propyl)-α-amanitin (HDP 30.1618)

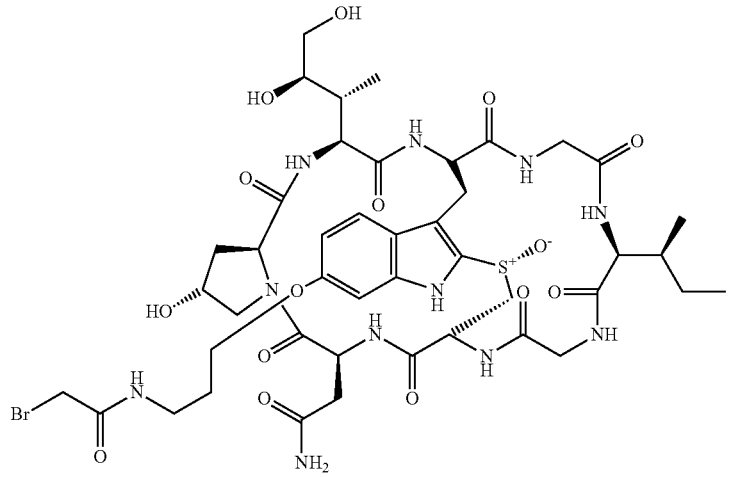

Application of the method from example 16 to 6'-O-(-3-aminopropyl)-α-amanitin, disclosed in EP 2621536 the bromo acetamide HDP 30.1618 was synthetized:

MS (ESI$^+$) found: 1096.22; calc.: 1096.34 [MH]$^+$ ($C_{44}H_{63}BrN_{11}O_{15}S$)

found: 1118.45; calc.: 1118.32 [M+Na]$^+$ ($C_{44}H_{62}BrN_{11}NaO_{15}S$)

Example 19

6'-[6-(6-(4-(5-(methylsulfonyl)-1,2,4-oxadiazol-2-yl)-phenyloxy)hexylaminocarbonyl)-aminohexyl)]-α-amanitin (HDP 30.1926)

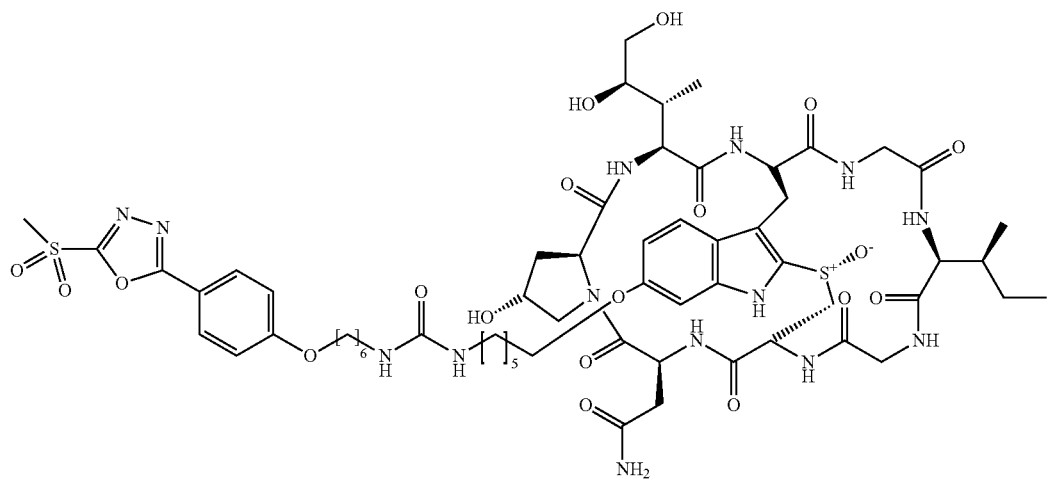

Methylsulfonyl-1,2,4-oxadiazol linkers were synthesized by variations of the methods, disclosed by Toda et al. in Angew. Chem. Int. Ed. 2013, 52, 12592-12596.

Step 1: 1-Azido-6-bromohexane

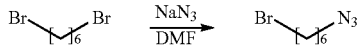

1,6-Dibromohexane (7.32 g, 30 mmol) was stirred overnight with sodium azide (1.95 mg, 30 mmol) in 60 ml DMF. The solvent was evaporated and the residue was stirred with 100 ml ethyl acetate for 5 min. Inorganic salts were filtered off and the monoazide is separated from dibromide and diazide by silica gel column chromatography with a gradient 0 to 20% dichloromethane in hexane to result 2.26 g (37%) product as an oil.

$^1$H NMR (500 MHz, CDCl$_3$) δ 3.42 (t, J=6.7 Hz, 2H), 3.28 (t, J=6.9 Hz, 2H), 1.88 (dt, J=14.6, 6.8 Hz, 2H), 1.62 (dt, J=14.3, 7.0 Hz, 2H), 1.53-1.36 (m, 4H).

$^{13}$C NMR (126 MHz, CDCl$_3$) δ 51.43, 33.80, 32.67, 28.82, 27.81, 26.03.

Step 2: Ethyl 4-[(6-azidohexyl)oxy]benzoate (HDP 30.1897)

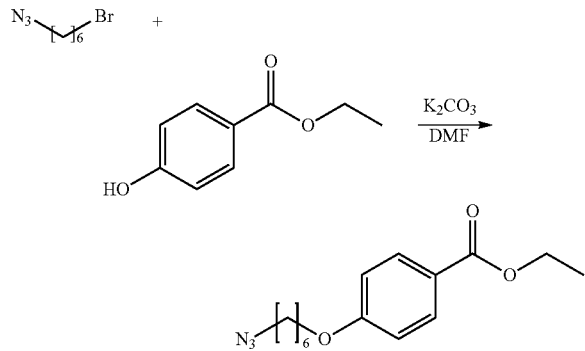

To a solution of step 1 product (4.122 g, 20 mmol) in DMF (40 mL) was added ethyl 4-hydroxybenzoate (3.324 g, 20 mmol) and K$_2$CO$_3$ (5.528 g, 40 mmol) at room temperature for 4 h. Then, the reaction mixture was diluted with 200 ml MTBE and 200 µl water. The organic layer was separated and washed with 3×100 ml water, dried (MgSO4) and evaporated to dryness. Purification by silica gel column chromatography (hexane/MTBE) gave the title compound (5.199 g, 89%) as a colorless oil.

MS (ESI$^+$) found: 314.33; calc.: 314.15 [M+Na]$^+$ (C$_{15}$H$_{21}$N$_3$NaO$_3$)

Step 3: 4-[(6-Azidohexyl)oxy]benzoyl hydrazide (HDP 30.1899)

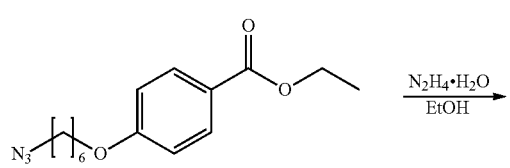

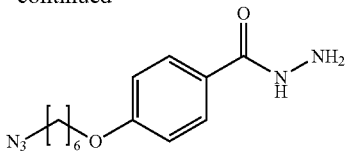

To a solution of step 2 product (5.19 g, 17.8 mmol) in ethanol (9.0 mL) was added hydrazine monohydrate (1459 µL, 30 mmol) at room temperature, and then the mixture was stirred at reflux for 22 h. The reaction mixture was concentrated in vacuo. The residue was purified by silica gel column chromatography (gradient dichloromethane to dichloromethane/ethyl acetate/methanol 6:3:1) to afford benzoylhydrazide derivative HDP 30.1899 (1.08 g, 22%) as colorless solid.

MS (ESI$^+$) found: 278.27; calc.: 278.16 [M+H]$^+$ (C$_{13}$H$_{20}$N$_5$O$_2$)

Step 4: 5-[4-((6-Azidohexyl)oxy)phenyl]-1,3,4-oxadiazole-2-thiol (HDP 30.1903)

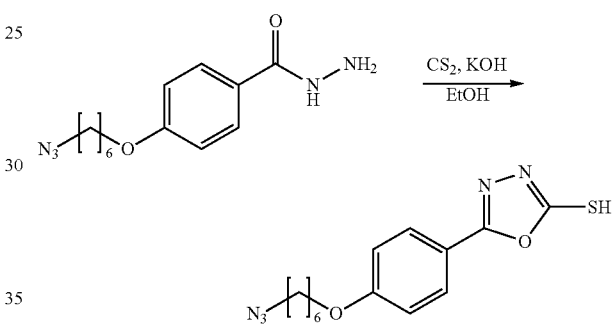

To a solution of benzoyl hydrazide derivative (1.08 g, 3.89 mmol) in ethanol (10.0 mL) was added carbon disulfide (1552 µL, 25.68 mmol) and powdered KOH (218 mg, 3.89 mmol) at room temperature, and then the solution was stirred at 85° C. for 3 h. Ethyl acetate and 1 M HCl were added to the solution. The organic layer was washed with saturated sodium bicarbonate and brine, dried over MgSO4, filtered and concentrated in vacuo. The residue was purified by silica gel column chromatography (hexane/ethyl acetate) to afford the title compound HDP 30.1903 (1.18 g, 95% yield) as a colorless solid.

Step 5: 5-[4-((6-Azidohexyl)oxy)phenyl]-5-(methylsulfanyl)-1,3,4-oxadiazole (HDP 30.1905)

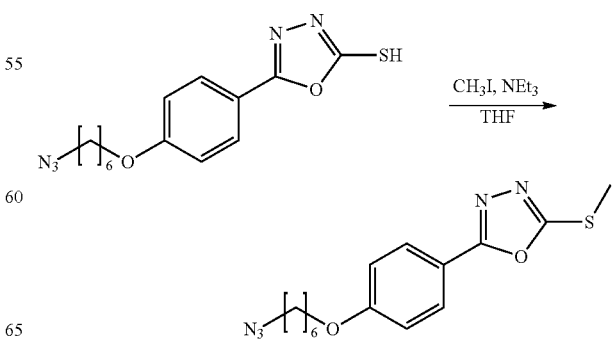

To a solution of step 4 thiol (1.18 g, 3.69 mmol) in THF (15 ml) was added methyl iodide (257 μL, 4.13 mmol) and triethylamine (625 μl, 4.51 mmol) at 0° C. Then, the mixture was stirred for 1 h at room temperature. Water (50 ml) and ethyl acetate (100 ml) was then added and the mixture was decolorized with 10% sodium thiosulfate solution (10 ml). The organic layer was separated, washed with brine (50 ml) and dried over MgSO$_4$. After filtration, the organic solvent was removed in vacuo, and the residue was purified on silica gel with hexane/MTBE to give the title compound HDP 30.1905 (1.03 mg, 84% yield) as a white solid.

MS (ESI$^+$) found: 334.27; calc.: 334.13 [M+H]$^+$ (C$_{15}$H$_{20}$N$_5$O$_2$S).

found: 356.29; calc.: 356.12 [M+Na]$^+$ (C$_{15}$H$_{19}$N$_5$NaO$_2$S).

Step 6: 5-[4-((6-Azidohexyl)oxy)phenyl]-5-(methylsulfonyl)-1,3,4-oxadiazole (HDP 30.1910)

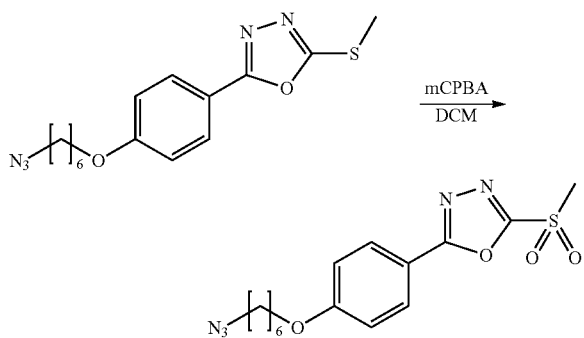

To a solution of step 5 product (1.00 g, 3.00 mmol) in dichloromethane (100 mL) was added mCPBA (68 wt %, 2.79 mg, 3.66 mmol) at 0° C., and then the mixture was stirred 24 h at room temperature. Magnesium sulfate was added, insoluble material was removed by filtration and the solvent was removed in vacuo. The residue was purified by silica gel column chromatography (hexane/MTBE) to afford the title compound HDP 30.1910 (858 mg, 78%).

MS (ESI$^+$) found: 366.00; calc.: 366.12 [M+H]$^+$ (C$_{15}$H$_{20}$N$_5$O$_4$S).

found: 388.19; calc.: 388.11 [M+Na]$^+$ (C$_{15}$H$_{19}$N$_5$NaO$_4$S).

Step 7: 5-[4-(((6-Succinimidyloxycarbonylamino)hexyl)oxy)phenyl]-5-(methylsulfonyl)-1,3,4-oxadiazole (HDP 30.1916)

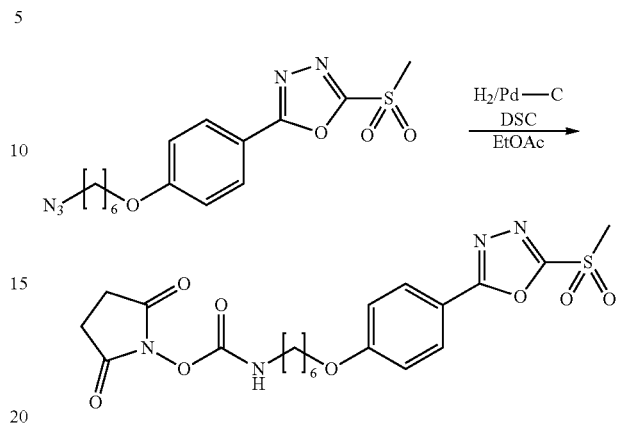

To a solution of step 6 product (370 mg, 1.01 mmol) in ethylacetate (100 ml) N,N'-disuccinimidyl carbonate (519 mg, 2.02 mmol) was added. The apparatus purged with argon, palladium (10% on activated charcoal) added and stirred subsequently overnight under hydrogen atmosphere. After filtration and evaporation, the crude product was purified on silica gel with a gradient of hexane to ethylacetate. Pure fractions were combined and lyophilized from 1,4-dioxane to yield the succinimidyl carbamate HDP 30.1916 (280 mg, 58%) as colorless powder.

MS (ESI$^+$) found: 481.10; calc.: 481.14 [M+H]$^+$ (C$_{20}$H$_{25}$N$_4$O$_8$S)

$^1$H NMR (500 MHz, CDCl$_3$) d 8.08-8.01 (m, 2H), 7.06-6.99 (m, 2H), 5.57 (t, J=5.9 Hz, 1H), 4.05 (t, J=6.4 Hz, 2H), 3.51 (s, 3H), 3.28 (q, J=6.8 Hz, 2H), 2.83 (s, 4H), 1.88-1.77 (m, 2H), 1.67-1.39 (m, 6H).

$^{13}$C NMR (126 MHz, CDCl$_3$) d 170.05, 166.73, 163.11, 161.53, 151.44, 129.68, 115.28, 114.03, 68.14, 42.98, 41.90, 29.39, 28.85, 26.23, 25.55, 25.47.

Step 8: 6'-[6-((6-((4-(5-(Methylsulfonyl)-1,2,4-oxadiazol-2yl)phenyl)oxy)hexyl)-aminocarbonylamino)hexyl]-α-amanitin (HDP 30.1926)

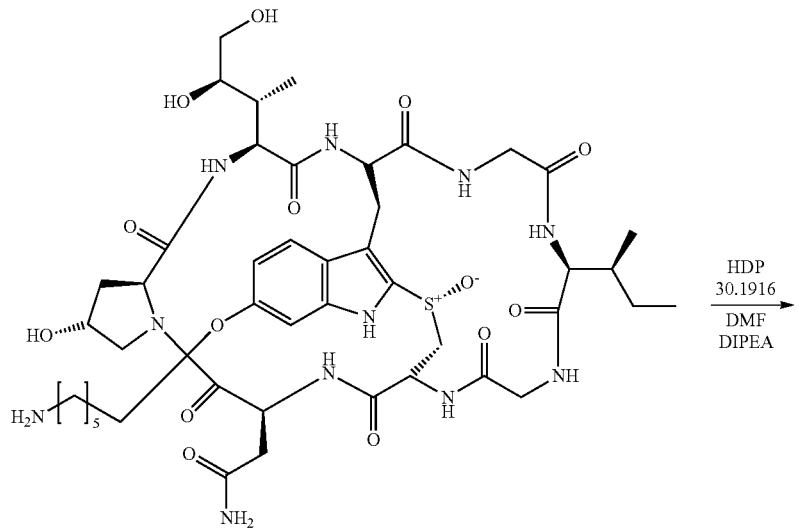

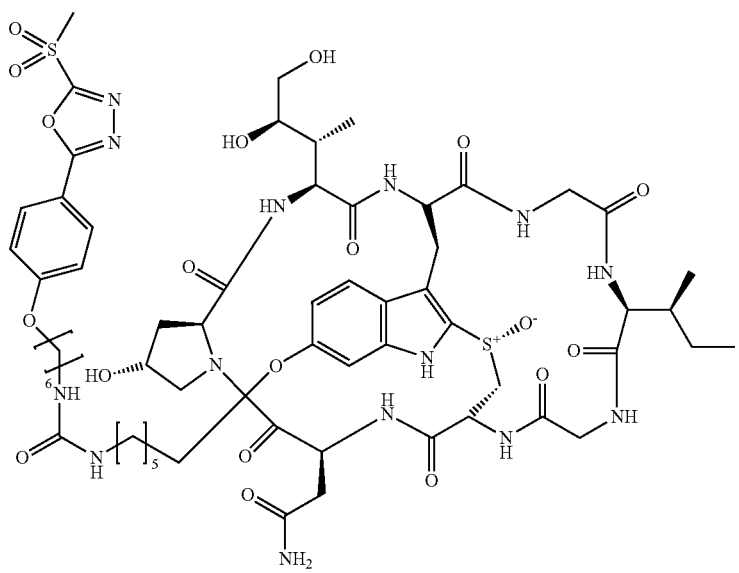

To 10.0 mg (8.83 μmol) 6'-O-(-6-aminohexyl)-α-amanitin (HDP 30.0134, synthesized as disclosed in EP 2621536), dissolved in 500 μl dry DMF were added subsequently 8.49 mg (17.66 μmol) dissolved in 500 μl DMF, and 6.01 μl (35.33 μmol) DIPEA. After 18 h at room temperature the volatiles were evaporated. The crude product purified by RP18 HPLC with a water-methanol gradient and the pure fractions were lyophilized from t-butanol/water: 7.04 mg (58%) HDP 30.1926 as colorless powder.

MS (ESI$^+$) found: 1383.62; calc.: 1383.57 [MH]$^+$ ($C_{61}H_{87}N_{14}O_{19}S_2$).

found: 1405.54; calc.: 1405.55 [M+Na]$^+$ ($C_{61}H_{86}N_{14}NaO_{19}S_2$).

Example 20

6'-[(3-Maleidopropanamido)-Ahx-Val-Cit-PAB]-α-amanitin (HDP 30.1426)

Dipeptide p-aminobenzylbromides were synthesized from the corresponding benzylacohols by adaption of the methods disclosed by Jeffrey et al. in *J. Med. Chem.* 2005, 48, 1344-1358. The general procedure is exemplified by the following scheme:

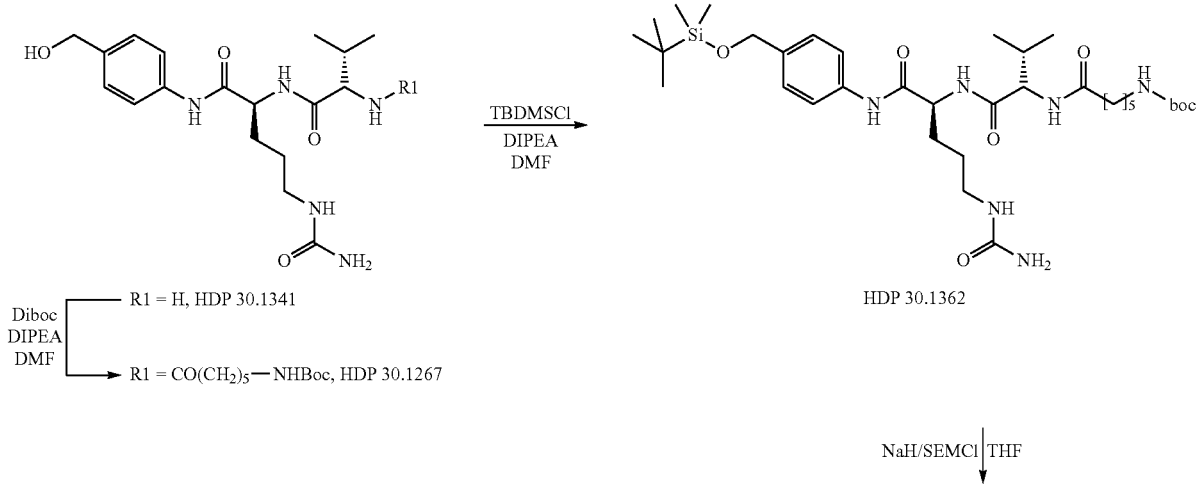

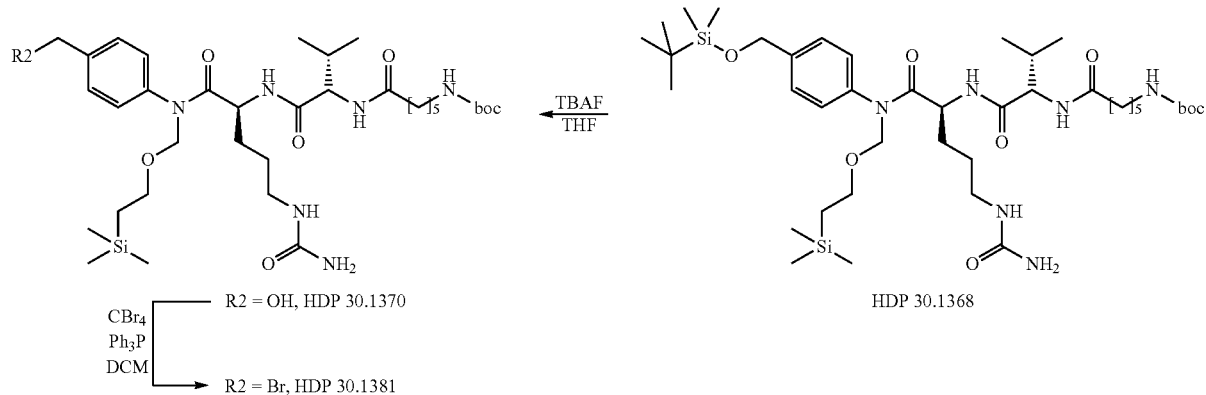

Step 1: Boc-Ahx-Val-Cit-PAB-OH (HDP 30.1267)

Preparation of valine-citrulline-p-aminobenzyl alcohol (H-Val-Cit-PAB-OH) and N-Boc-aminocaproic acid N-hydroxysuccinimide ester (Boc-Ahx-NHS) are disclosed by Firestone et al. in U.S. Pat. No. 6,214,345. By this methods, crude H-Val-Cit-PAB-OH, was prepared, from 4.79 g (7.96 mmol) Fmoc-Val-Cit-PAB-OH and dissolved in 50 ml DMF. Boc-Ahx-NHS, (2.88 g, 8.76 mmol) and 1489 µl (8.76 mmol) N-ethyldiisopropylamine was added and stirred at room temperature overnight. After evaporation of DMF the residue was stirred with 100 ml MTBE overnight and the solids are isolated via centrifugation. The pellet was resuspended in MTBE and centrifuged again. The product was vacuum-dried to 4.44 g (94% yield) slight brownish powder.

MS (ESI$^+$) found: 615.19; calc.: 615.35 [M+Na]$^+$ ($C_{29}H_{48}N_6NaO_7$)

Step 2: Boc-Ahx-Val-Cit-PAB-OTBDMS (HDP 30.1362)

Step 1 product (4.44 g, 7.49 mmol) was dissolved in 20 ml DMF and 6.37 µl (37.45 mmol) N-ethyldiisopropylamine and 3.39 g (22.47 mmol) tert-butyldimethyl-chlorosilane (TBDMSCl) were added. After 3 h the DMF was evaporated and the residue was partitioned between 120 ml ethyl acetate/methanol 5:1 and 100 ml 0.2M citric acid. The organic layer washed with water and saturated sodium bicarbonate, dried (MgSO4) and concentrated under reduced pressure. The crude product was eluted from 120 g silica gel with a gradient of 0 to 10% methanol in dichloromethane. Pure fractions were combined and evaporated to 2.50 g (47%) product as a solid.

MS (ESI$^+$) found: 729.29; calc.: 729.43 [M+Na]$^+$ ($C_{35}H_{62}N_6NaO_7Si$)

Step 3: Boc-Ahx-Val-Cit(SEM)-PAB-OTBDMS (HDP 30.1368)

To a solution of step 2 product (2.50 mg, 3.546 mmol) in THF (40 mL) was added NaH (142 mg of a 60% dispersion in mineral oil, 3.546 mmol). After 15 min, neat 2-(trimethylsilyl)-ethoxymethyl chloride (SEMCl) (703 µl, 3.546 mmol) was added, and the reaction mixture was stirred for 8 h. Diatomaceous earth (10 g) was added to the reaction mixture and the volatiles were removed under reduced pressure. The remaining solids were applied on top of a silica gel column and eluted with a gradient of 0 to 10% methanol in dichloromethane. Pure fractions were combined and evaporated to 637 mg (21%) of amorphous title compound.

MS (ESI$^+$) found: 859.34; calc.: 859.52 [M+Na]$^+$ ($C_{41}H_{76}N_6NaO_8Si_2$)

Step 4: Boc-Ahx-Val-Cit(SEM)-PAB-OH (HDP 30.1370)

To a solution of step 3 product (567 mg, 0.677 mmol) in THF (20 mL) was added TBAF (833 µL of a 1.0 M solution, 0.833 mmol; 1.2 eq.). After 1 h, Diatomaceous earth (1.5 g) was added to the reaction mixture and the volatiles were removed under reduced pressure. The remaining solids were applied on top of a silica gel column and eluted with a gradient of 0 to 10% methanol in chloroform. Pure fractions were combined and evaporated to 279 mg (57%) product as a white solid MS (ESI$^+$) found: 745.28; calc.: 745.43 [M+Na]$^+$ ($C_{35}H_{62}N_6NaO_8Si$)

Step 5: Boc-Ahx-Cit(SEM)-PAB-Br (HDP 30.1381)

To a solution of step 4 product (100 mg, 139 µmol) in dichloromethane (5 mL) was added triphenylphosphine (73 mg, 2 eq.) followed by carbon tetrabromide (92 mg, 2 eq.). After 1 h, Diatomaceous earth (1 g) was added to the reaction mixture and the volatiles were removed under reduced pressure. Elution from 12 g silica gel with a gradient of 0 to 10% methanol in dichloromethane yields 61 mg (56%) of title product as an oil.

MS (ESI$^+$) found: 807.15/809.17; calc.: 807.35/809.34 [M+Na]$^+$ ($C_{35}H_{61}BrN_6NaO_7Si$)

Step 6: 6'-[Boc-Ahx-Cit(SEM)-PAB]-α-amanitin (HDP 30.1383)

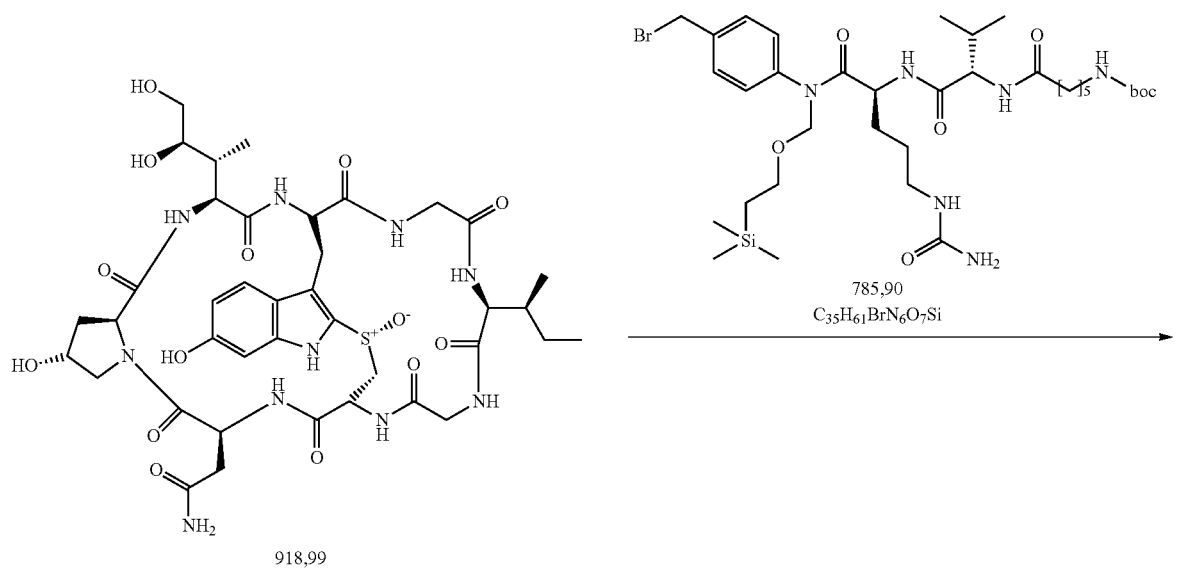

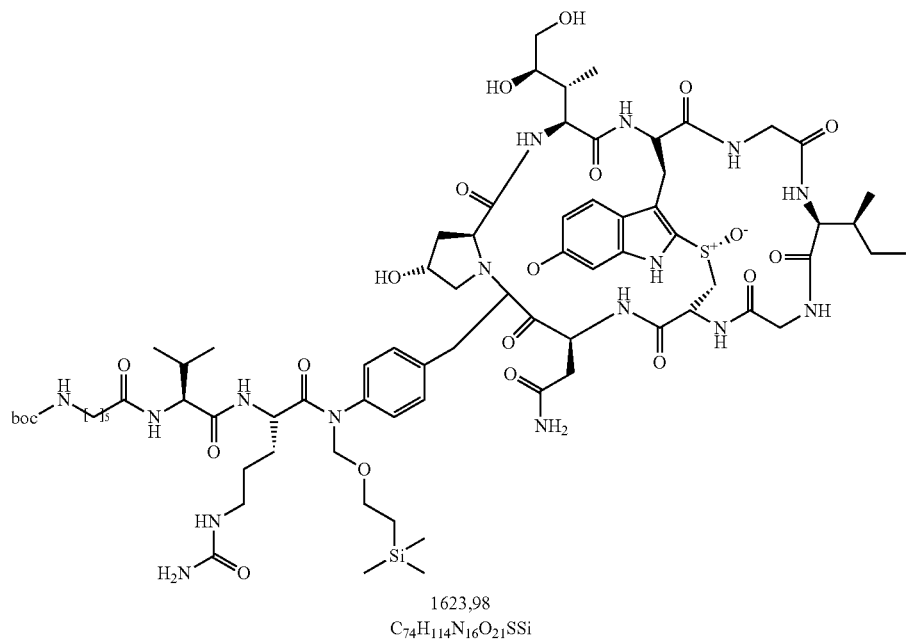

Under argon and at room temperature 44 mg (47.9 µmol) of vacuum dried α-amanitin were dissolved in 1000 µl dry dimethyl sulfoxide (DMSO). Step 5 product (61 mg, 78.1 µmol) and 1M sodium hydroxide (52.7 µl, 1.1 eq.) were added. After 4 h at room temperature the reaction mixture was acidified to pH=5 with 52.7 µl of a 1 M acetic acid solution in DMSO. The solvent is removed in vacuo and the residue was purified by preparative HPLC on a C18 column with a gradient from 5-100% methanol. The product containing fractions evaporated to 25.1 mg (32%) HDP 30.1383 as a colorless solid.

MS (ESI$^+$) found: 1646.40; calc.: 1645.77 [M+Na]$^+$ ($C_{74}H_{114}N_{16}NaO_{21}SSi$)

Step 7: 6'-[H-Ahx-Cit-PAB]-α-amanitin (HDP 30.1388)

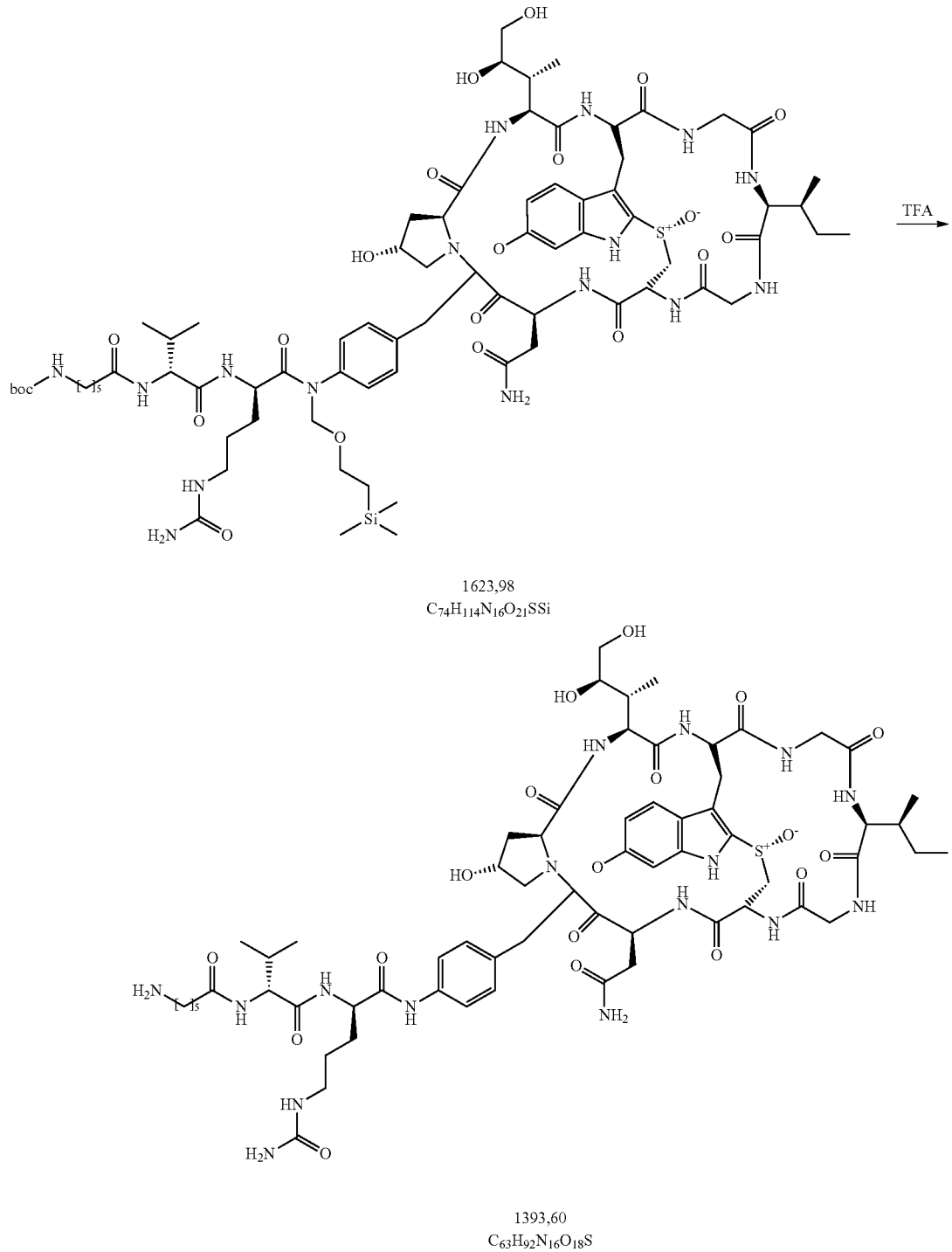

The Boc- and SEM-protected Step 6 product (18.4 mg, 11.3 μmol) was dissolved in 2 ml trifluoroacetic acid. After 2 min the mixture was evaporated to dryness at room temperature redissolved in 2 ml water and adjusted drop wise to pH 10 with 3.2% ammonia. The resulted suspension was freeze-dried, applied to RP18 HPLC with a gradient of 5-100% methanol in 0.05% TFA and the pure fractions were evaporated and lyophilized from 2 ml water: 12.1 mg (71%) HDP 30.1388 colorless powder.

MS (ESI$^+$) found: 1393.42; calc.: 1393.66 [M+H]$^+$ ($C_{63}H_{93}N_{16}O_{18}S$)

Step 8

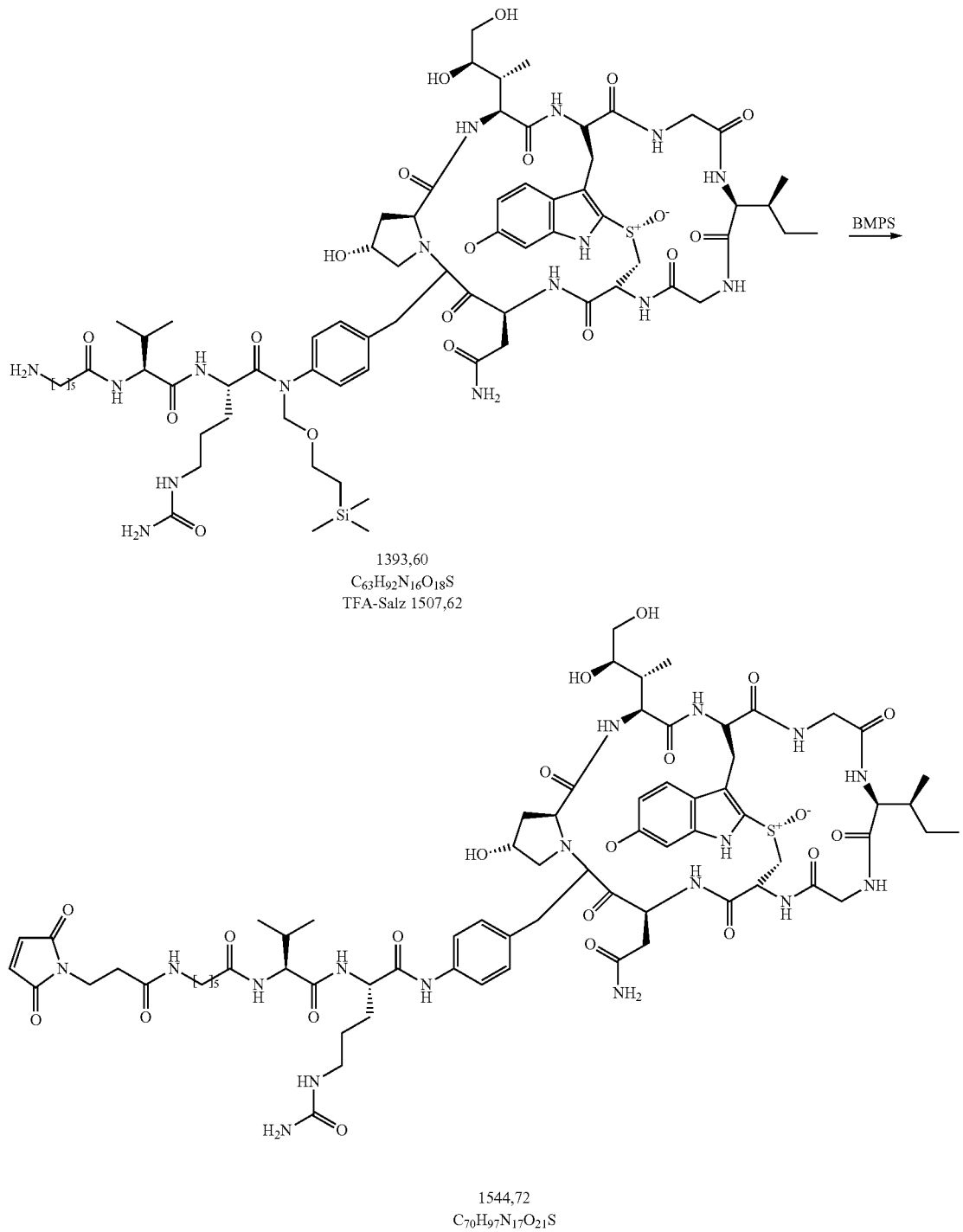

To 9.98 mg (6.62 μmol) step 7 product, dissolved in 500 μl dry DMF were added subsequently 5.29 mg (19.86 μmol) 3-(maleimido)propanoic acid N-hydroxysuccinimide ester (BMPS) in 500 μl DMF, and 3.38 μl (19.86 μl) DIPEA. After 2 h at room temperature 100 μl water was added to the reaction mixture and the volatiles were evaporated. The crude product purified by RP18 HPLC with a water-methanol gradient and the pure fractions were lyophilized from t-butanol/water: 5.43 mg (53%) title product 6'-[(3-Maleidopropanamido)-Ahx-Cit-PAB]-α-amanitin as colorless powder.

MS (ESI$^+$) found: 1544.25; calc.: 1544.68 [M+H]$^+$ ($C_{70}H_{98}N_{17}O_{21}S$).

found: 1566.44; calc.: 1566.67 [M+Na]+ ($C_{70}H_{97}N_{17}NaO_{21}S$).

Example 21

6'-[H-Val-Ala-PAB]-α-amanitin (HDP 30.1702)

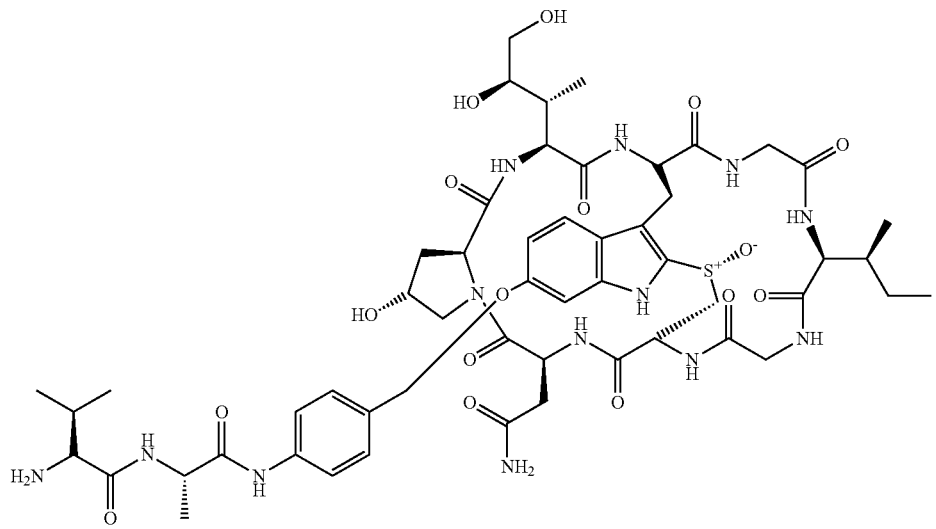

By repeating the methods of example 20 steps 1-7 with H-Val-Ala-PAB-OH as starting material the title substance was received as colorless powder:

MS (ESI$^+$) found: 1194.58; calc.: 1194.53 [M+H]$^+$ ($C_{54}H_{76}N_{13}O_{16}S$)

The starting material H-Val-Ala-PAB-OH can be prepared by general methods in peptide chemistry and is exemplified by Howard et al. in US 2011/0256157.

Example 22

6'-((3-Maleidopropanamido)-Val-Ala-PAB)-α-amanitin (HDP 30.1699)

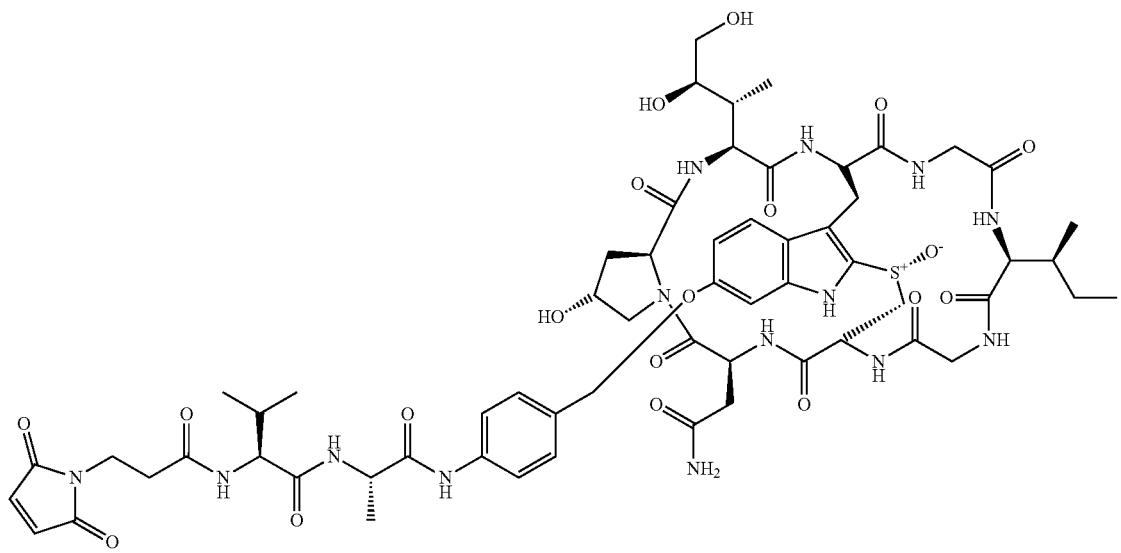

By using the method of example 20, step 8 with 6'-[H-Val-Ala-PAB]-α-amanitin from example 21 the title substance was received in 81% yield as colorless powder:

MS (ESI$^+$) found: 1345.48; calc.: 1345.55 [MH]$^+$ ($C_{61}H_{81}N_{14}O_{19}S$).

found: 1368.17; calc.: 1367.53 [M+Na]$^+$ ($C_{61}H_{80}N_{14}NaO_{19}S$).

Example 23

6'-O—[((N-α-Maleimido)-L-2,3-diaminopropanamido)-Val-Ala-PAB]-α-amanitin (HDP 30.1957)

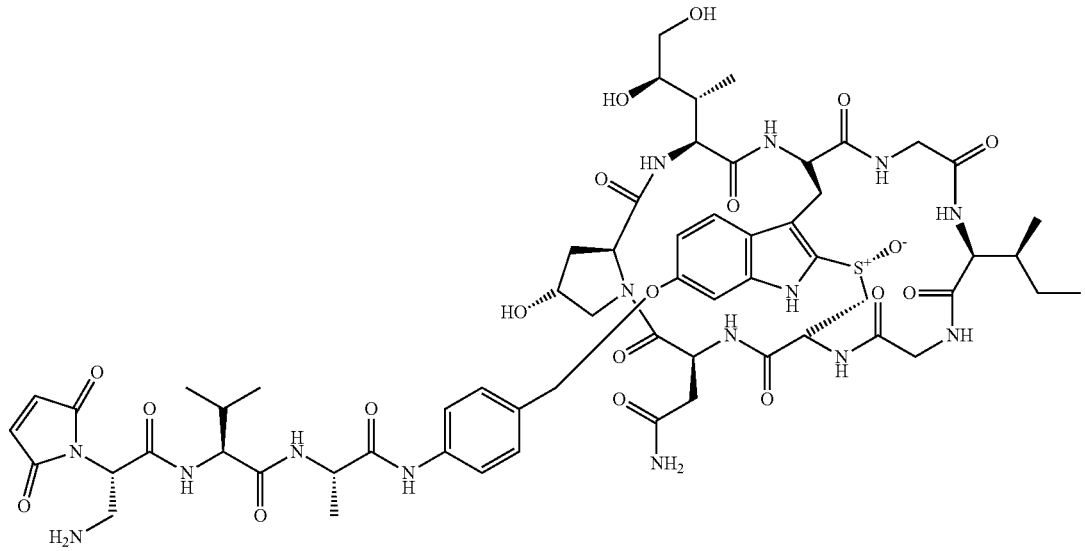

By using the method of example 16 with 6'-[H-Val-Ala-PAB]-α-amanitin from example 21 the title substance was received in 39% yield as colorless powder:

MS (ESI$^+$) found: 1345.48; calc.: 1360,56 ($C_{61}H_{82}N_{15}O_{19}S$)

Example 24

6'-((2-Bromo acetamido)-Val-Ala-PAB)-α-amanitin (HDP 30.1704)

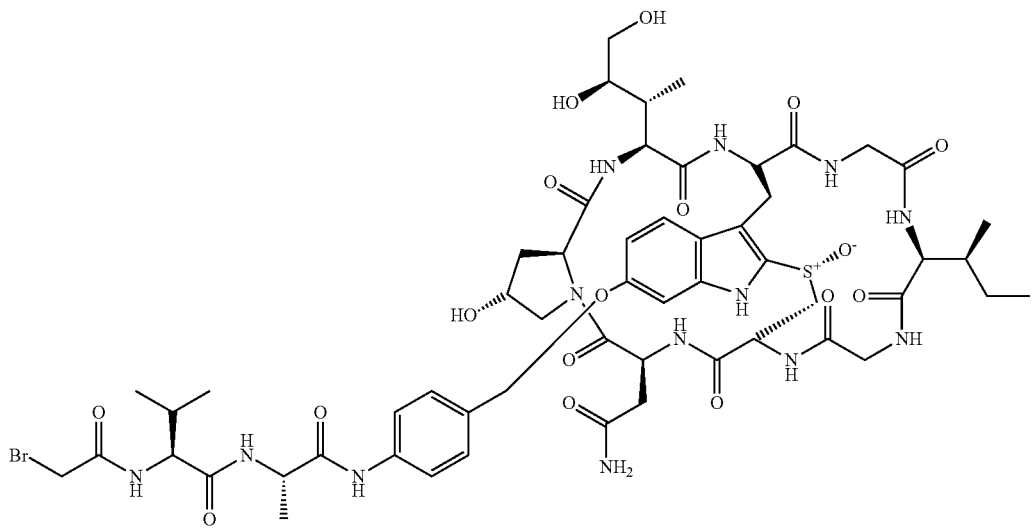

By using the method of example 17 with 6'-[H-Val-Ala-PAB]-α-amanitin from example 21 the title substance was received in 26% yield as colorless powder:

MS (ESI$^+$) found: 1314.28; calc.: 1314.45 [M+H]$^+$ ($C_{56}H_{77}N_{13}O_{17}S$).

found: 1336.39; calc.: 1336.43 [M+Na]$^+$ ($C_{56}H_{76}N_{13}NaO_{17}S$).

Example 25

6'-((6-(4-(5-(methylsulfonyl)-1,2,4-oxadiazol-2-yl)-phenyloxy)hexylaminocarbonyl)-Val-Ala-PAB)-α-amanitin (HDP 30.1917)

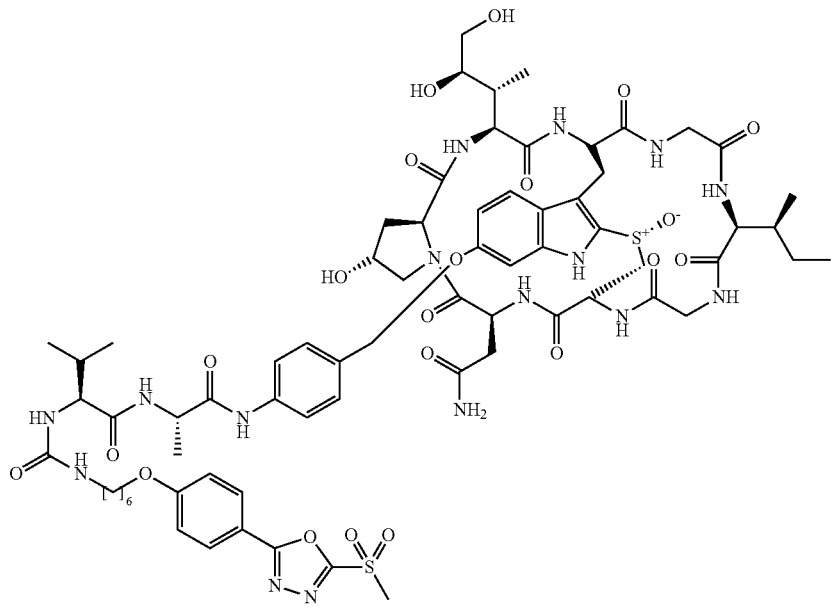

By using the method of example 19 with 6'-[H-Val-Ala-PAB]-α-amanitin from example 21 the title substance was received in 44% yield as colorless powder: MS (ESI$^+$) found: 802.63 calc.: 802.30 [M+2Na]$^{2+}$ ($C_{70}H_{94}N_{16}Na_2O_{21}S_2$)

Example 26

6'-((6-(4-(5-(methylsulfonyl)-1,2,4-oxadiazol-2-yl)-phenyloxy)hexylaminocarbonyl)-Ahx-Val-Ala-PAB)-α-amanitin (HDP 30.1930)

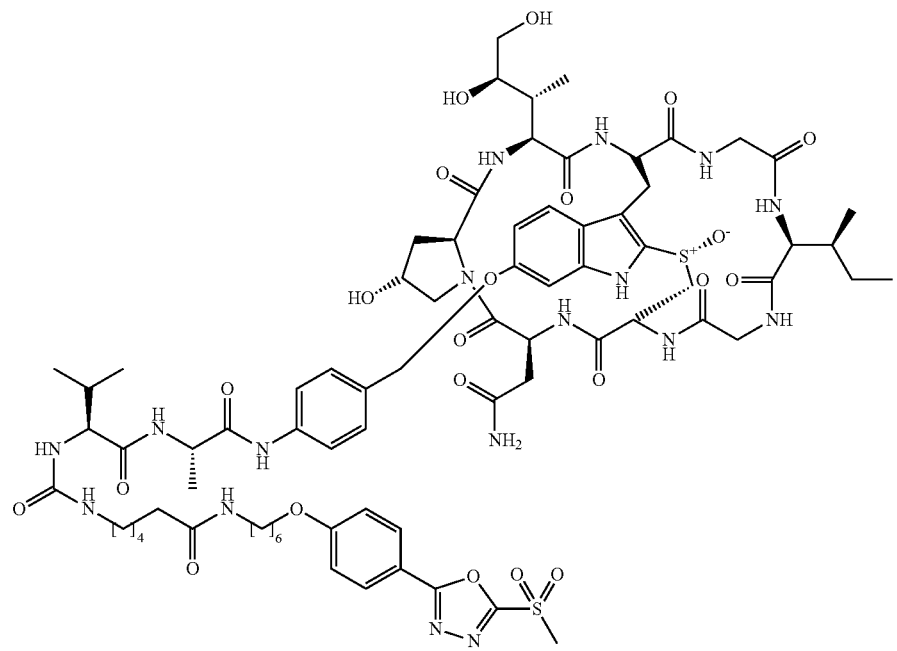

By using the method of example 19 with 6'-[H-Ahx-Val-Ala-PAB]-α-amanitin prepared by the methods of example 19 step 1-7 with replacement of citrulline to alanine the title substance was received in 37% yield as colorless powder:

MS (ESI$^+$) found: 859.02; calc.: 858.85 [M+2Na]$^{2+}$ ($C_{76}H_{105}N_{17}Na_2O_{22}S_2$)

Example 27

6'-O-[3-(5-Nitro-pyridine-2-yldisulfanyl)propyl)]-α-amanitin HDP 30.0951

Step 1: 6''-O-(3-S-Tritylsulfanyl-propyl)-α-amanitin HDP 30.0517

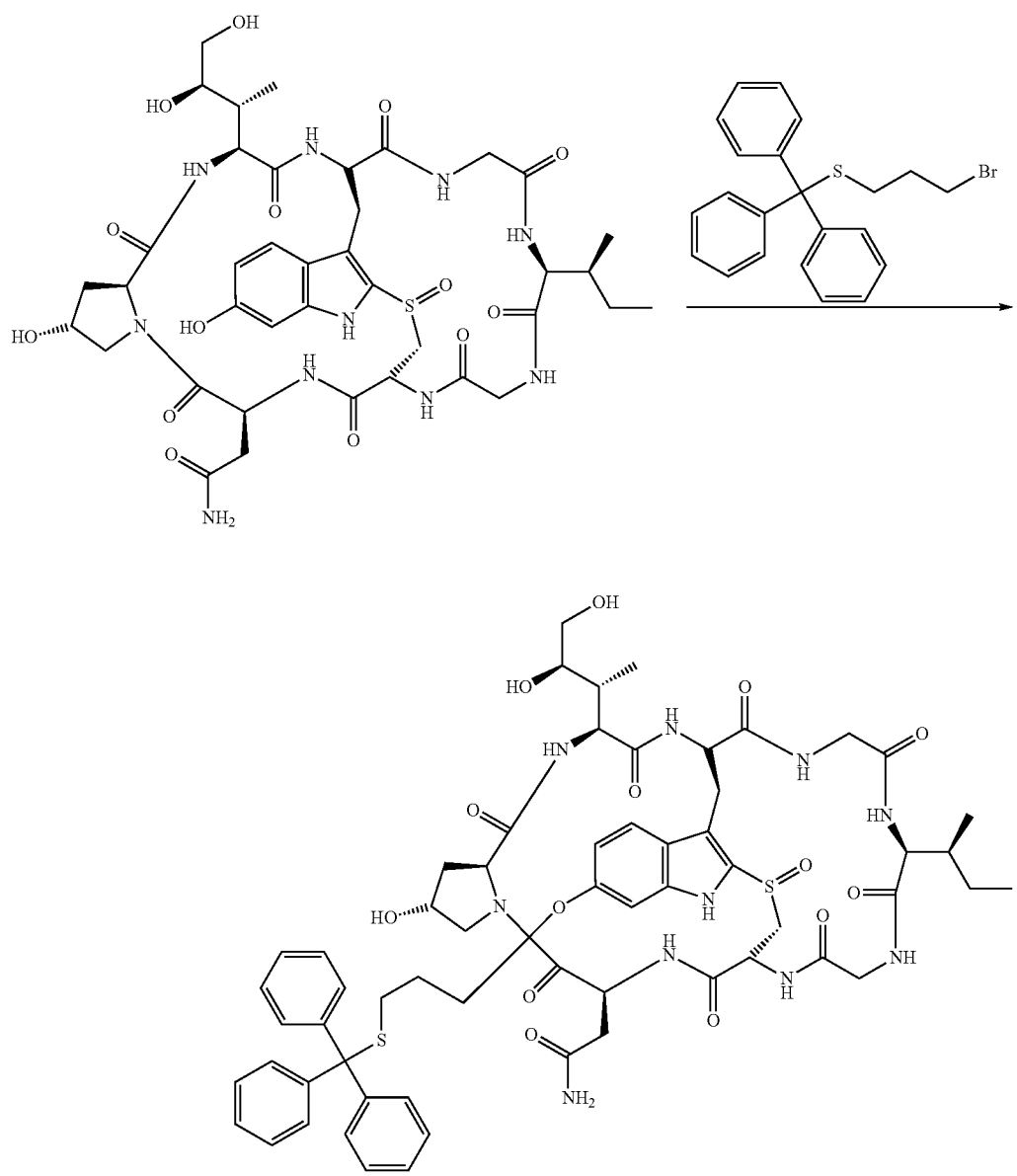

Under argon 46 mg (50 μmol) of vacuum dried α-amanitin was dissolved in 2500 μl dry dimethyl sulfoxide (DMSO). 3-(S-trityl)-mercaptopropyl-1-bromide (159 mg, 8 eq.) was added, followed by 60 μl of a 1M sodium hydroxide solution. After 1.5 h at room temperature the reaction mixture was acidified to pH=5 with 50 μl 1M acetic acid in DMSO and the solvent is evaporated. The residue was dissolved in 200 μl Methanol and added drop wise to a centrifugation tube filled with 10 ml of tert-butylmethyl ether (MTBE). The resulted precipitate was cooled to 0° C. for 10 min and isolated by centrifugation (4000×g) and washed with 10 ml MTBE subsequently. The supernatants were discarded and the pellet dissolved in 750 μl methanol and purified in 3 portions on prep. HPLC on a C18 column (250×21.2 mm, Luna RP-18, 10 μm, 100 Å). Solvent A: water, solvent B: methanol; Gradient: 0 min 5% B; 5 min 5% B 20 min 100% B; 25 min 100% B; 27 min 5% B, 35 min 5% B; Flow 30 ml/min. The fractions with a retention time of 21.1-21.8 min were collected and the solvents evaporated to 36.5 mg (59%) HDP 30.0517 as a colorless solid.

MS (ESI+) 1234.8 [M+H]$^+$, 1257.3 [M+Na]$^+$

Step 2: 6'-O-[3-(5-Nitro-pyridine-2-yldisulfanyl)propyl)]-α-amanitin HDP 30.0951

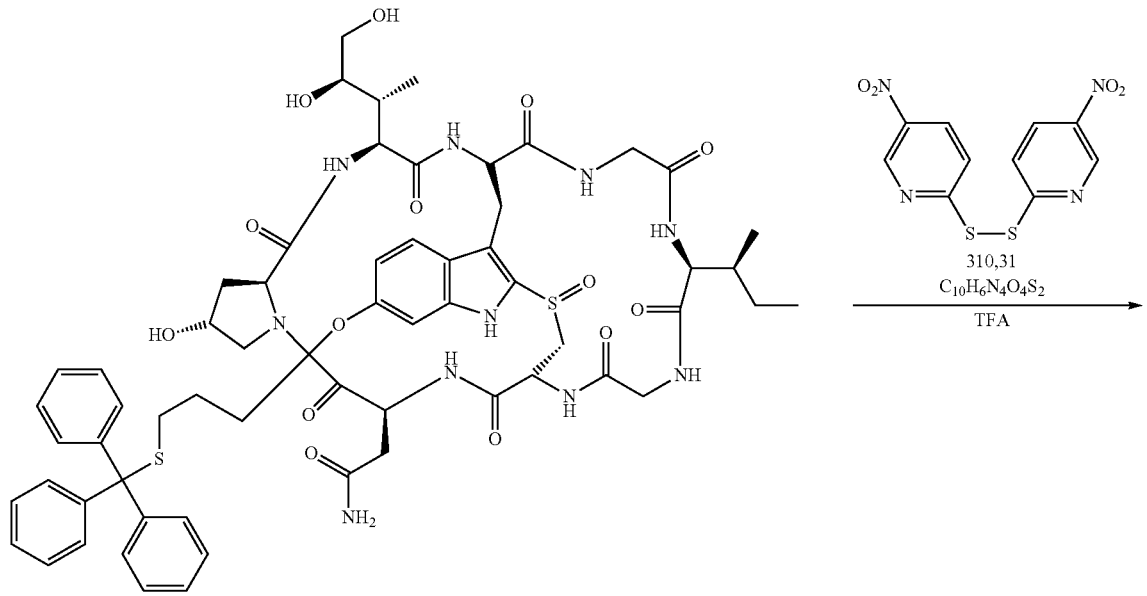

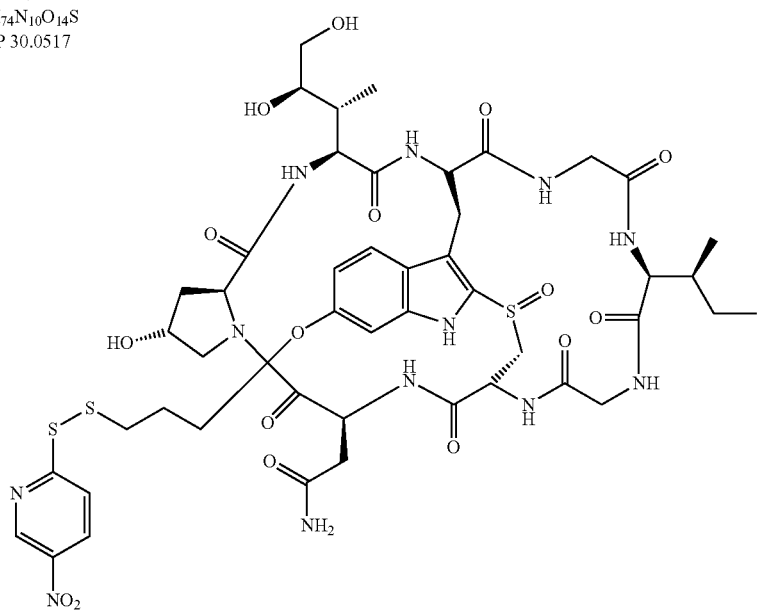

To step 1 product (5.00 mg, 4.05 μmol) 2,2'-dithiobis(5-nitropyridine), DTNP (6.28 mg, 5 eq.) dissolved in 200 μl trifluoroacetic acid was added. After 4 min the volatiles were distilled off and the residue was co-evaporated with 1000 μl Methanol. The crude product was HPLC purified analog to step 1. The fractions with a retention time of 18.46-19.28 min were collected and the solvents evaporated and the residue lyophilized from 2 ml tert-butanol to 2.99 mg (64%) HDP 30.0951 as a slight yellowish solid.

MS (ESI$^+$) 1146.97 [M+H]$^+$, 1169.17 [M+Na]$^+$

Example 28

Experimental Settings Leading to FIGS. 5A to 14

Figure 11:
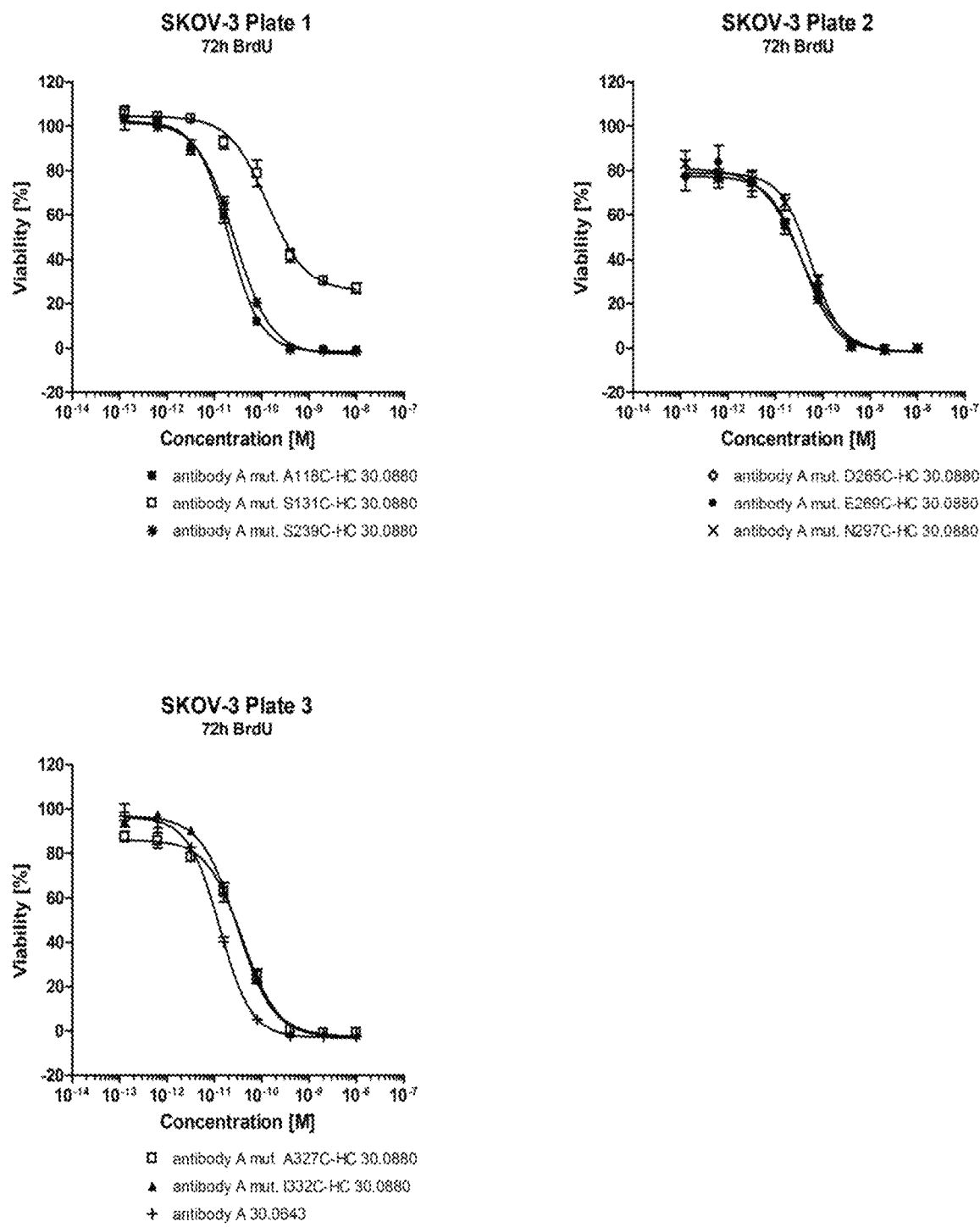
FIG. 11 shows the results of a BrdU-incorporation assay for determination of cell viability after 72 h incubation with different anti-HER2 ADCs and HER2-positive SKOV-3 cancer cells.
Figure 12:
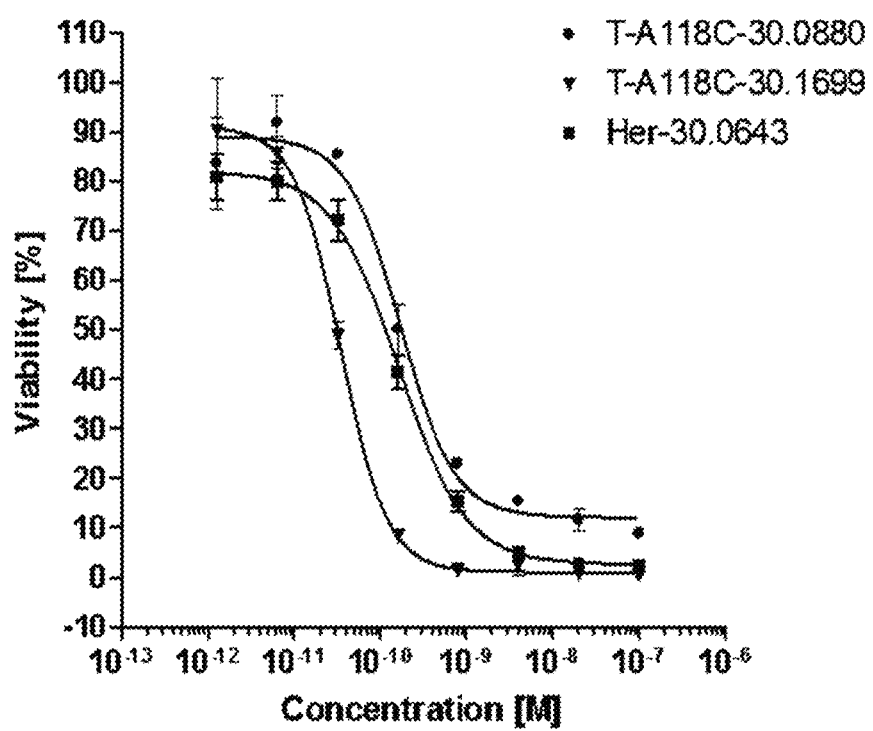
FIG. 12 shows the results of a BrdU-incorporation assay for determination of cell viability after 72 h incubation with different anti-HER2 ADCs and HER2-positive NCI-N87 cancer cells
Figure 13:
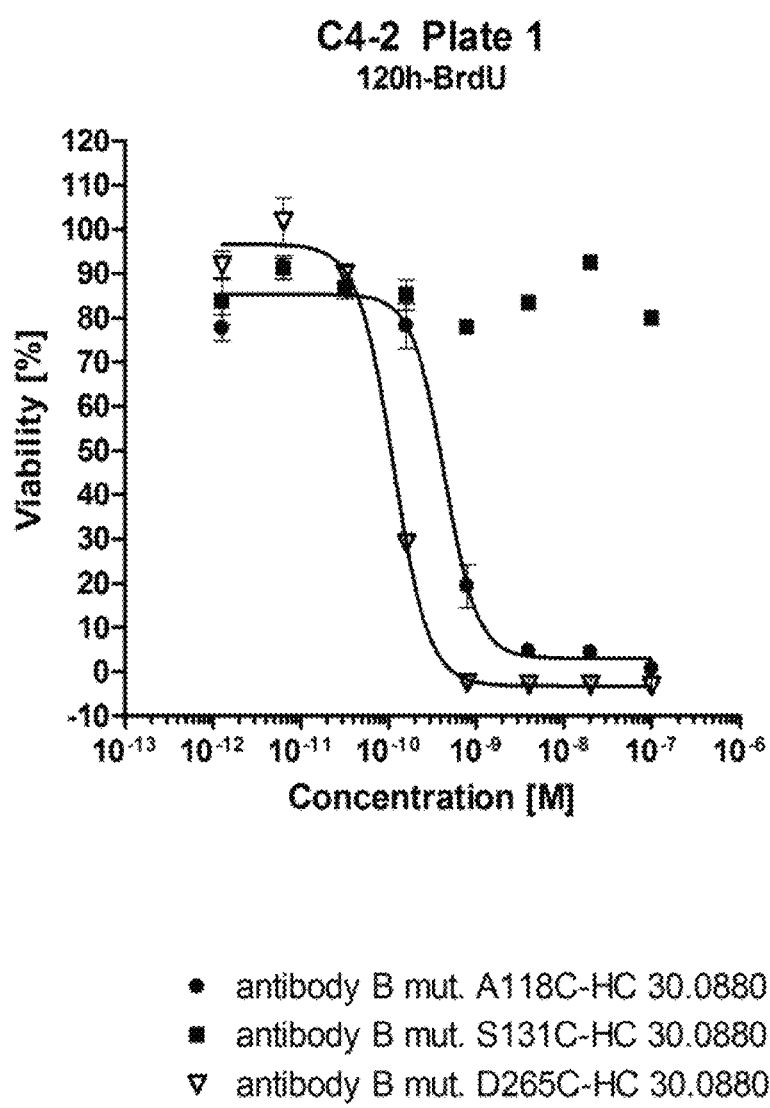
FIG. 13 shows the results of a BrdU-incorporation assay for determination of cell viability after 120 h incubation with different anti-PSMA ADCs and PSMA-positive C4-2 prostate cancer cells.
Figure 14:
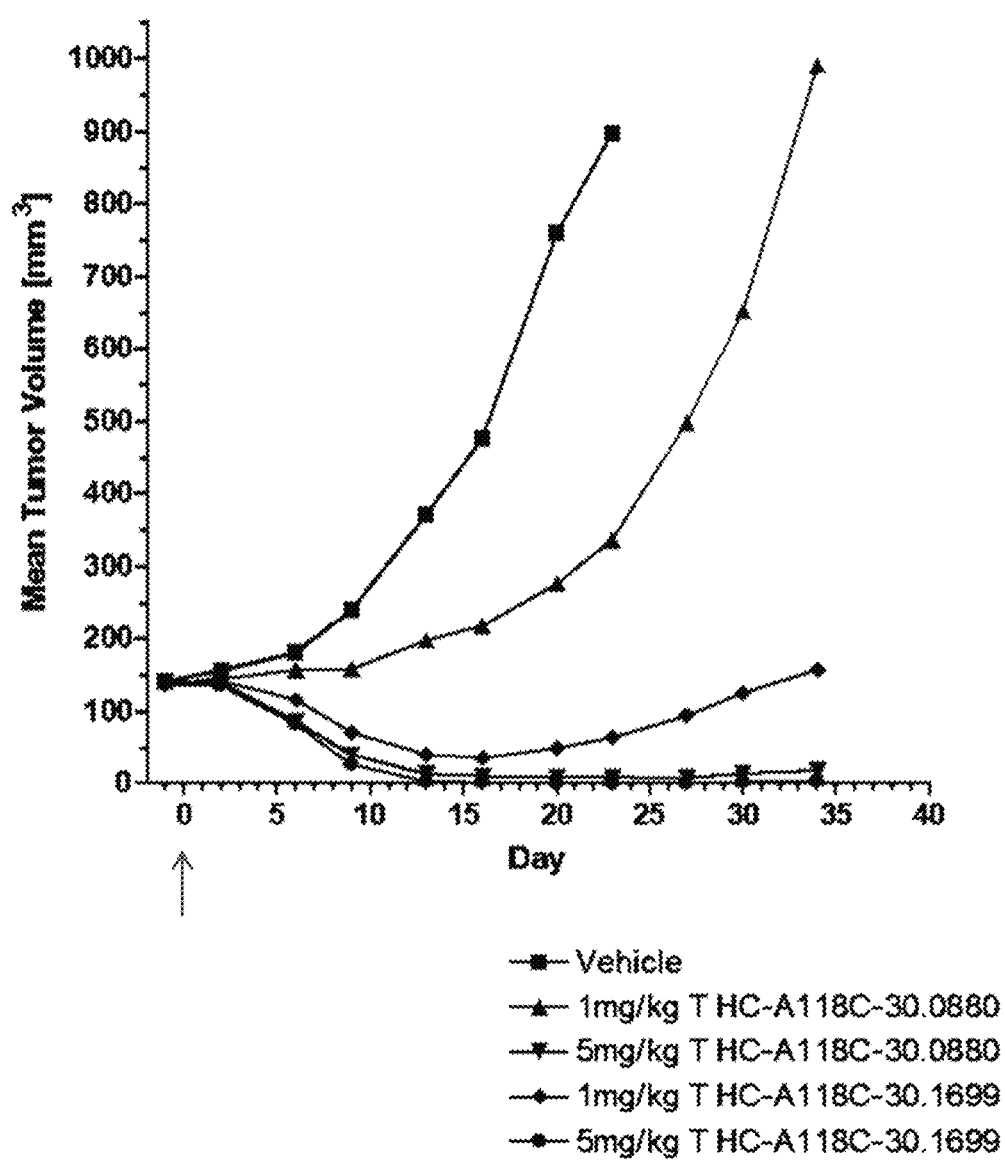
FIG. 14 shows the results of a subcutaneous HER2-positive SKOV-3 xenograft model treated with anti-HER2 based ADCs.

Cell Viability Assays Based on BrdU Incorporation (FIG. 11, 12, 13)

To assess the effects of compounds on antigen-expressing tumor cell lines, 2500 cells/well were plated in 90 μl medium. The next day 10 μl medium containing different concentrations of antibody-drug conjugates were added. A BrdU incorporation assay (Cell Proliferation ELISA, BrdU, Roche) was performed after 72 or 96 h of drug exposure. Chemoluminescence was measured using a FLUOstar Optima chemoluminometer (BMG LABtech). $EC_{50}$ values for each compound were determined by sigmoidal dose-response curve analysis using Graphpad Prism 4.0 software.

Figure 8A:
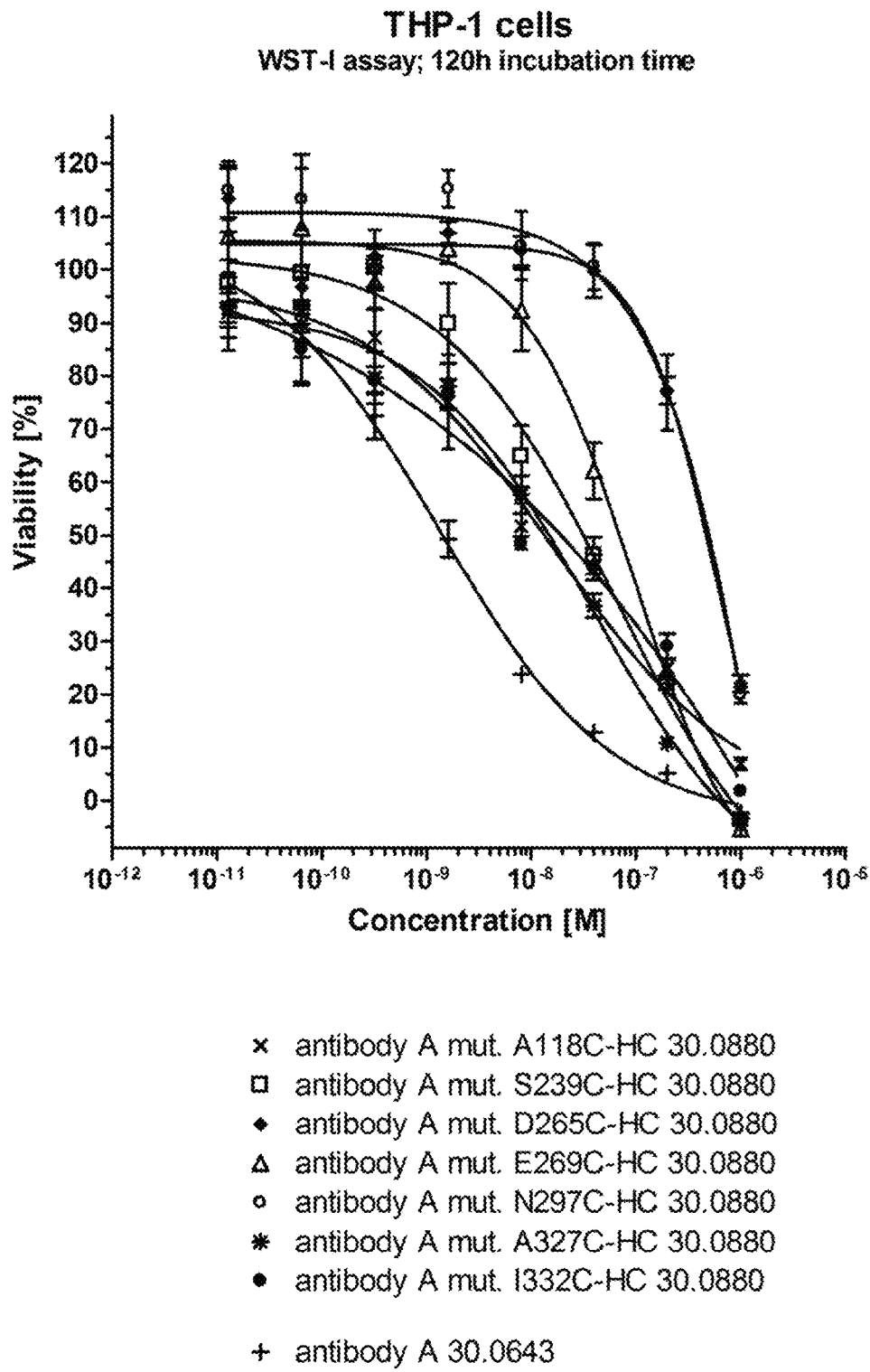
Figure 8B:
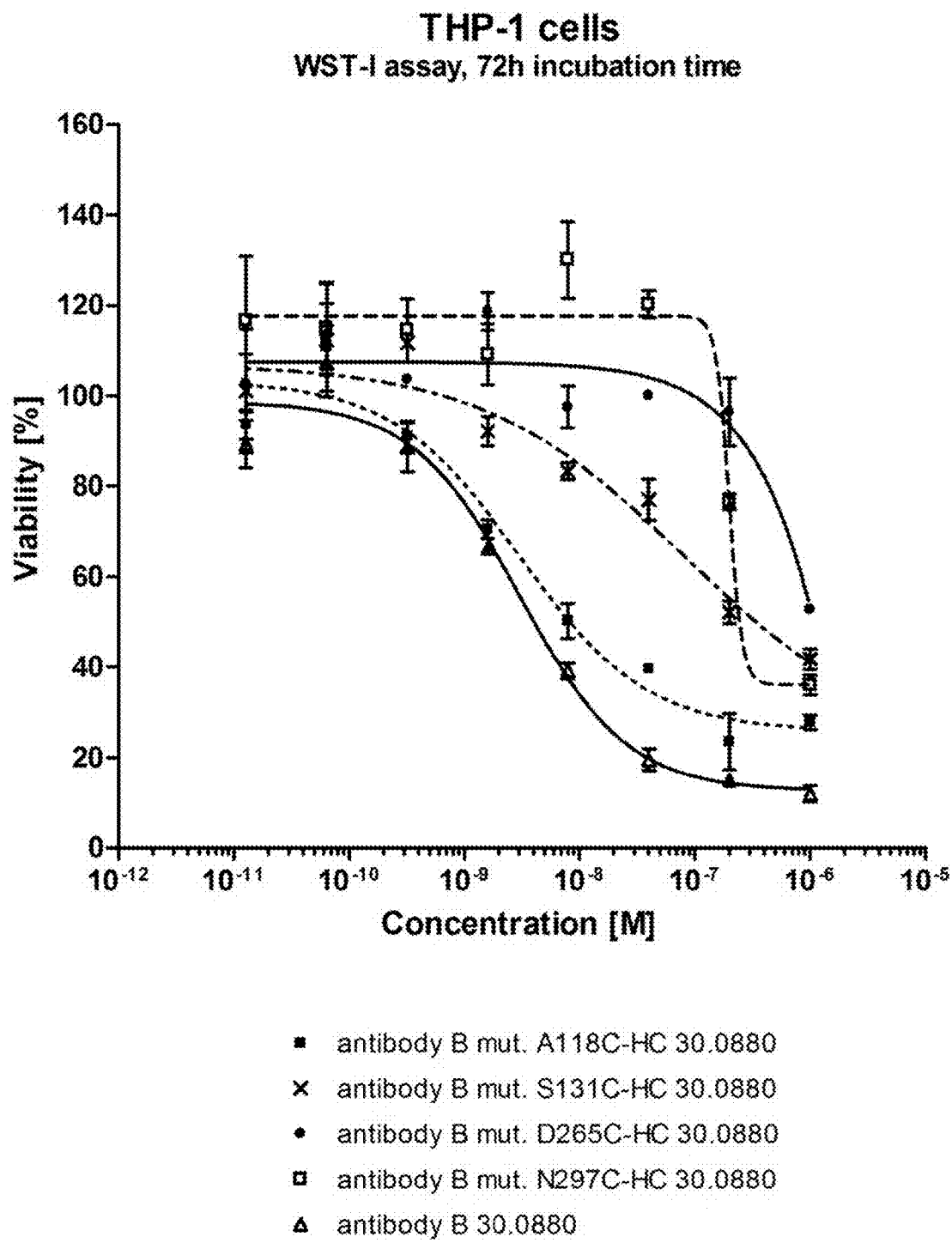

Cell Proliferation Assays Based on WST-I (FIG. 8)

To assess the effects of compounds on Fcg-receptor expressing THP-1 cells, 2500 cells/well were plated in 90 µl medium. The next day 10 µl medium containing different concentrations of antibody-drug conjugates were added. 96 h after drug application 10 µl of Cell Proliferation Agent WST-1 (Roche) was added to each well. After additional 4 h to 24 h incubation the absorbance at 440 nm/660 nm was determined using a FLUOstar Optima chemoluminometer (BMG LABtech). $EC_{50}$ values for each compound were determined by sigmoidal dose-response curve analysis using Graphpad Prism 4.0 software.

Figure 6:
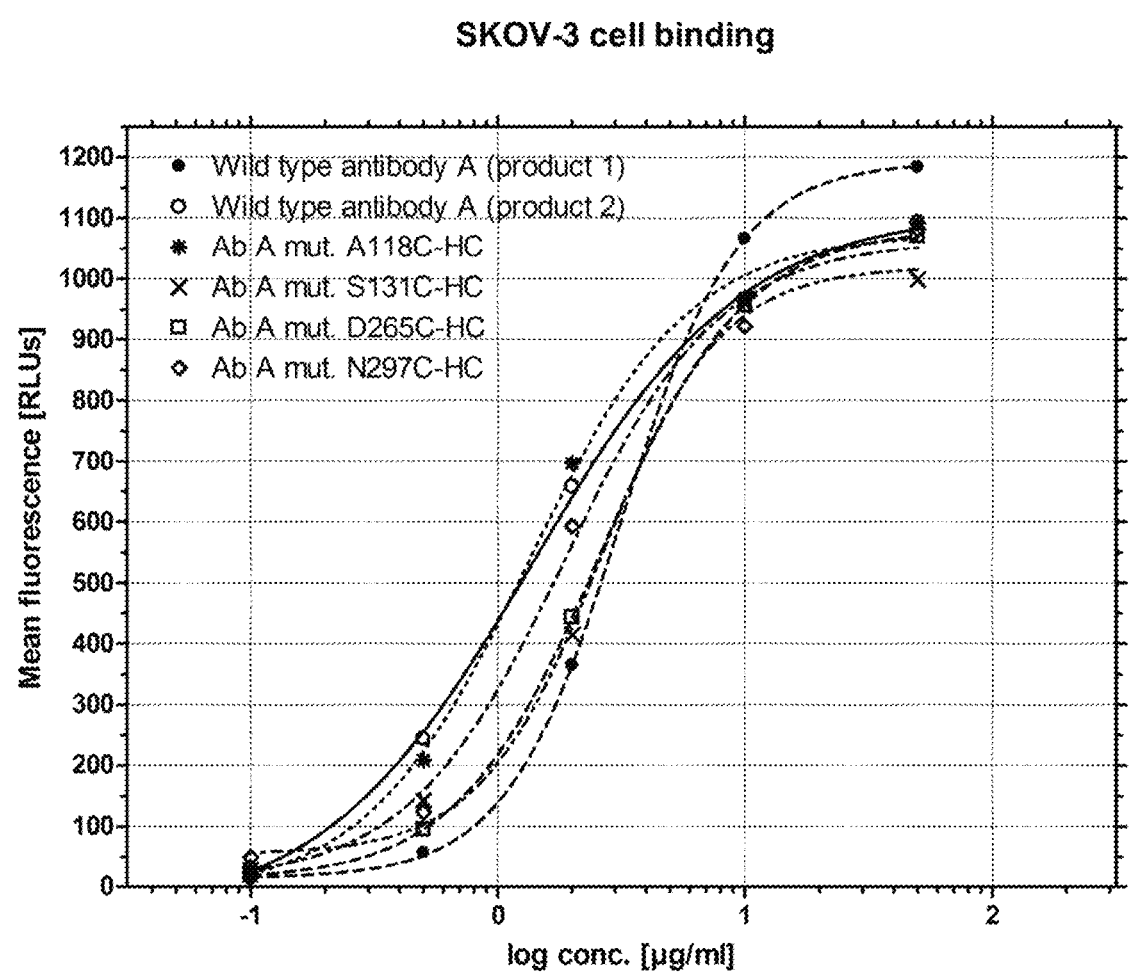

Cell Surface Binding Assay (FIG. 6)

100 µl cell suspension in PBS containing $1 \times 10^6$ antigen-expressing tumor cells were incubated for 30 min at 4° C. with or without 0.1-50 µg/ml antibody or antibody-drug conjugate. For detection, goat anti-Human IgG (H+L)-Alexa Fluor 488 F(ab')$_2$-fragment (Dianova) was used. The fixed stained cells were analyzed by FACS on a BD FACScan device. Sample mean fluorescence intensity was calculated using the BD CellQuest Pro software and plotted against the IgG concentration upon subtraction of the control sample value to obtain the binding curves.

Figure 7A:
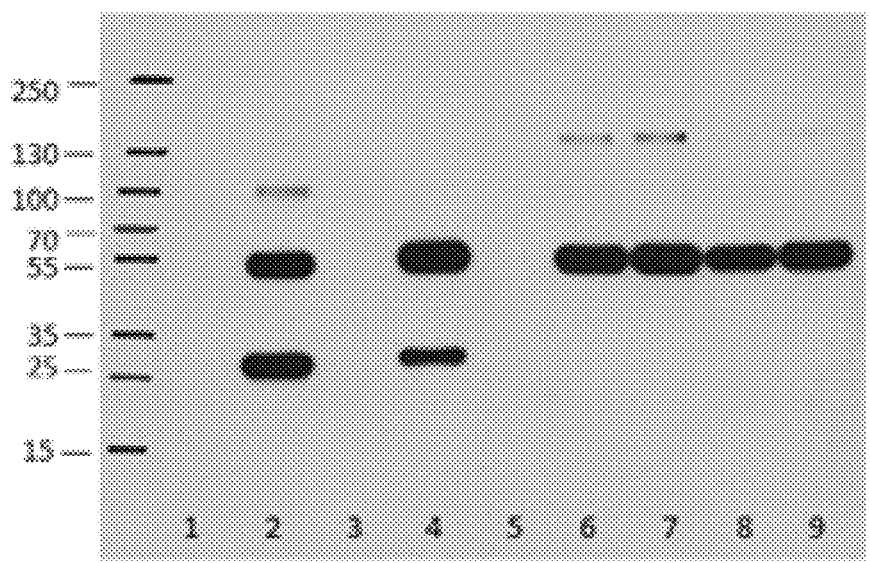
Figure 7A:
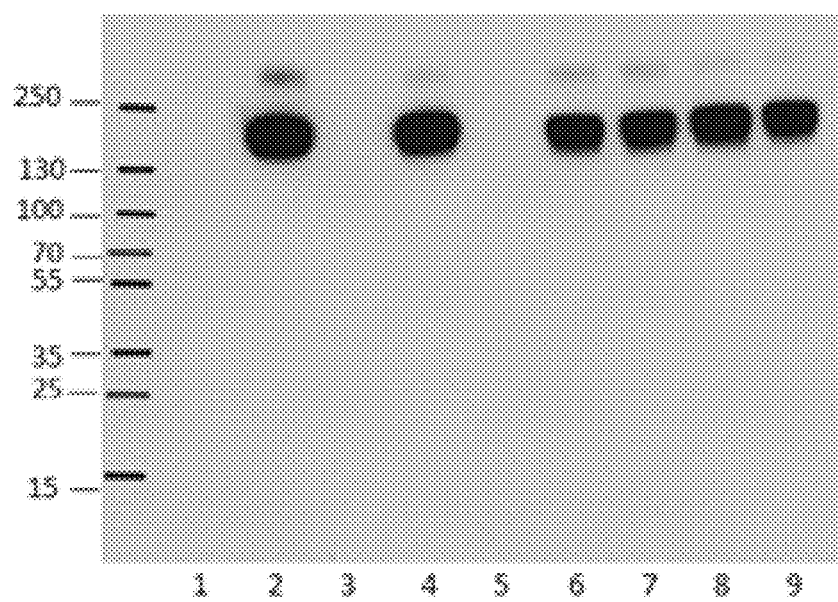
Figure 7B:
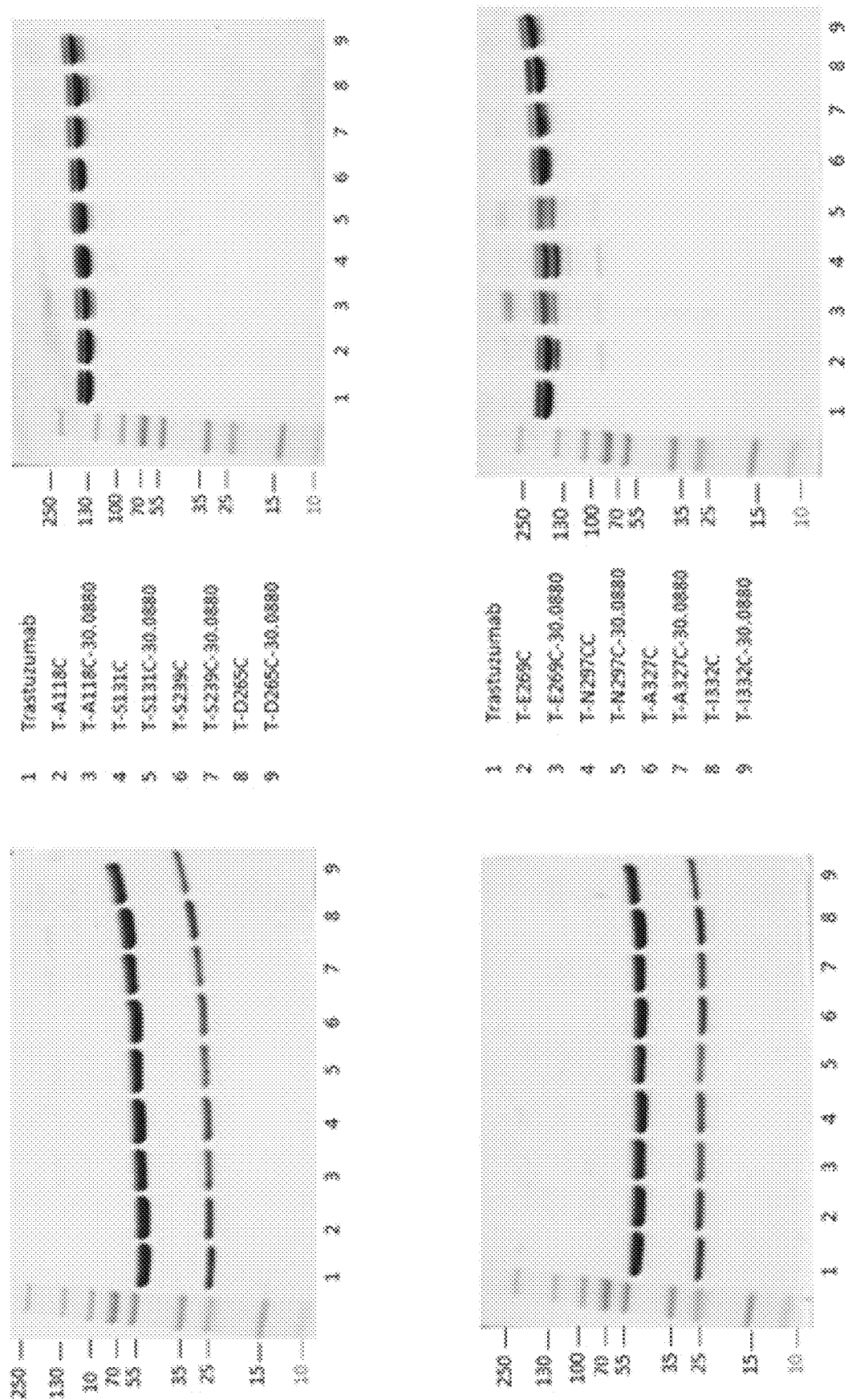
Figure 7B:
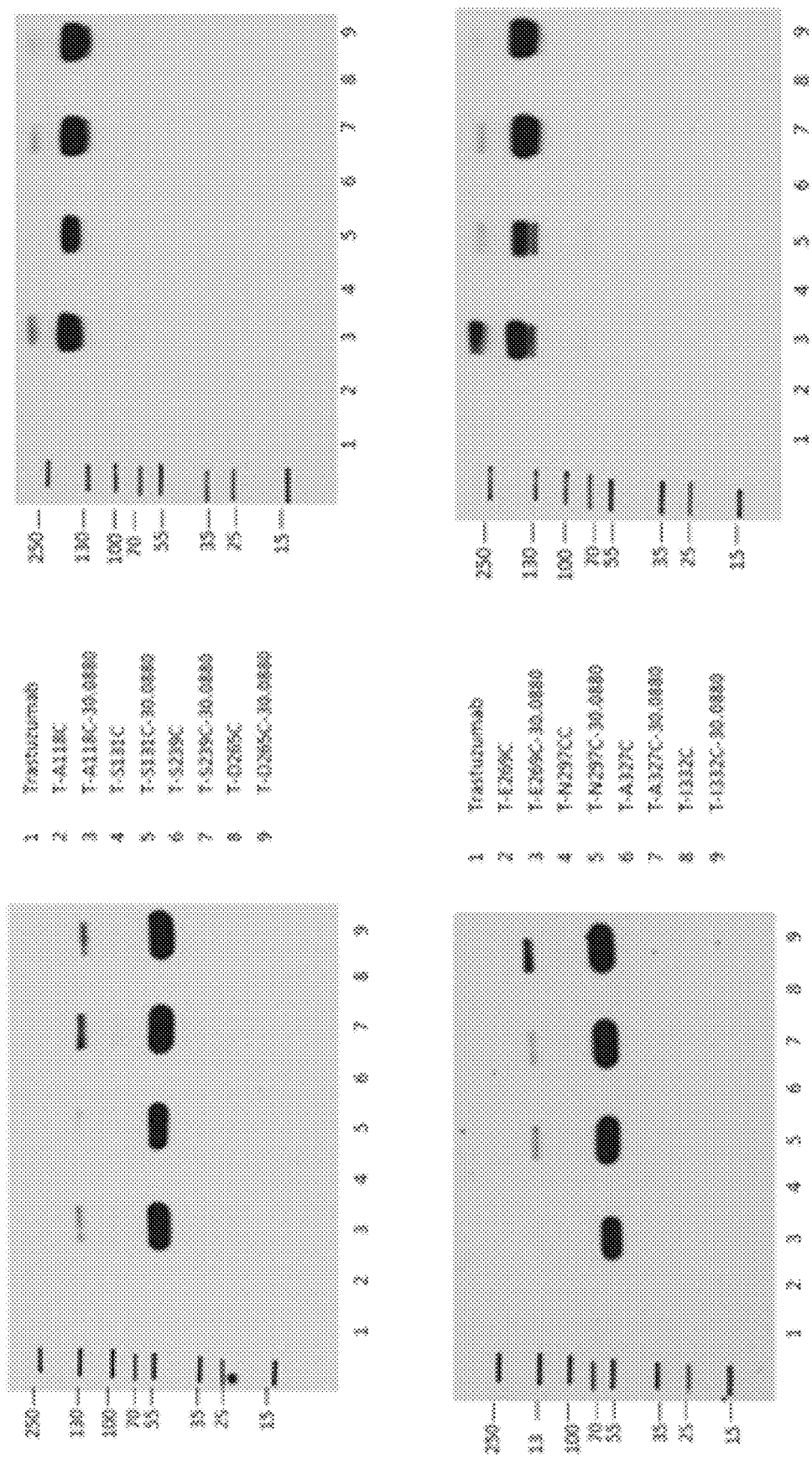

SDS-PAGE with Coomassie-Blue Staining and Western Blotting (FIGS. 7A and 7B)

Antibodies and antibody-drug conjugates were analyzed by reducing and non-reducing SDS-PAGE followed by Coomassie-blue staining or Western Blot detection of amanitin payload according to standard methods. For detection of a polyclonal rabbit serum was used, which allows detection of amanitin and amanitin-linker compounds conjugated to proteins.

Mouse Tolerability and Efficacy Experiments (FIG. 9, 14)

The maximum tolerated dose (MTD), defined as the dose that causes individual body weight loss that does not exceed 10%, was assessed for single intravenous doses of antibody-drug conjugates. For xenograft models, $5 \times 10^6$ tumor cells (early passage number) suspended in 240 µl medium were subcutaneously injected into the right flank of 7 to 8-week-old female NMRI nude mice (Janvier). Once the tumors reached a mean volume of 100 to 200 mm$^3$, animals were randomly assigned in treatment groups of eight animals per group. Single dose intravenous treatment was applied for all animals. Endotoxin concentrations <1 EU (Endotoxin Unit) per mg protein were demonstrated for all batches used for in vivo experiments by using an Endosafe-PTS system (Charles River). Application volume was 10 ml/kg body-weight and PBS was used as vehicle control. Tumor growth was measured with a caliper and tumor volume was calculated using the formula Tvol=(larger diameter×(smaller diameter)$^2$×0.5). Mice were sacrificed when moribund or at the indicated time points by $CO_2$ inhalation. All animal studies were done according to German animal welfare standards (GV-SOLAS) and had been approved by the responsible board (Regierungsprasidium Karlsruhe, Referat 35). Statistical analysis was performed using Prism software (GraphPad Software, Inc.) and 1-Way ANOVA.

The following Table 1 shows the therapeutic index of different Her2-Amanitin-ADCs:

TABLE 1

Therapeutic index of different Her2-Amanitin-ADCs

| | MTD Dose (mg/kg) | MED Dose (mg/kg) | TI MTD/MED (dose based) | MTD AUC (day*ug/ml) | MED AUC (day*ug/ml) | TI MTD/MED (AUC based) |
|---|---|---|---|---|---|---|
| Her2-30.0643 | <0.3* | 0.5 | 0.2 | 9 | 20 | 0.5 |
| Her2-A118C-30.0880 | 3 | 2 | 1.5 | 420 | 80 | 5.3 |
| Her2-D265C-30.0880 | 10 | 2 | 5 | 1710 | 80 | 21.4 |

Figure 10A:
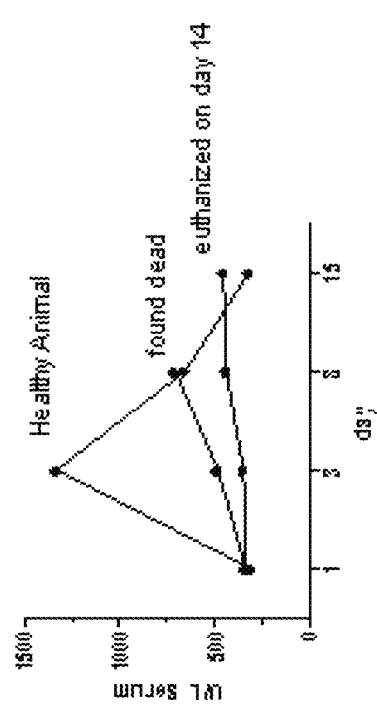
Figure 10B:
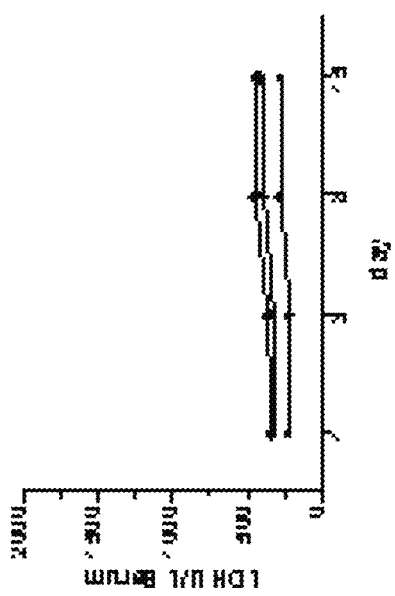
Figure 10C:
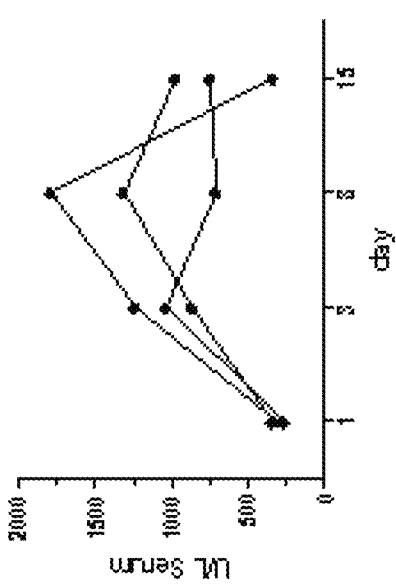
Figure 10D:
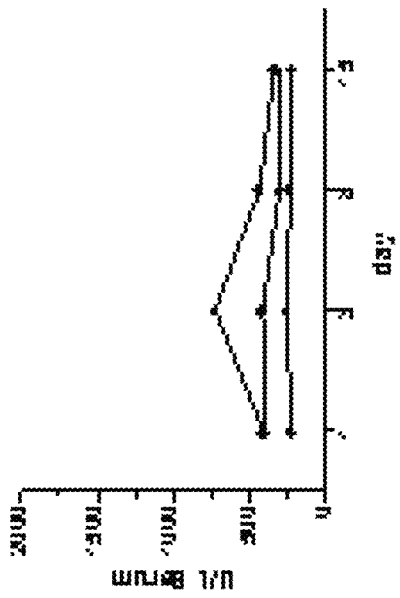

MTD—Maximal tolerated dose;
MED—Minimal tolerated dose;
AUC—Area under the curve
*assuming 0.1 for calculation Cynomolgus Monkey Tolerability Study (FIGS. 10A-10B)

Figure 10F:
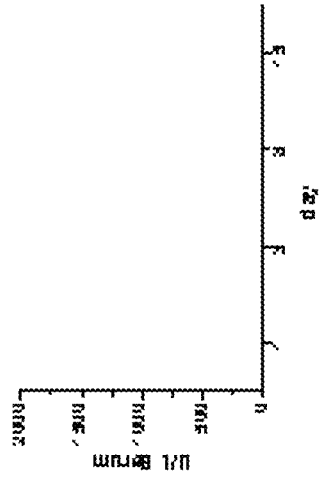
Figure 10H:
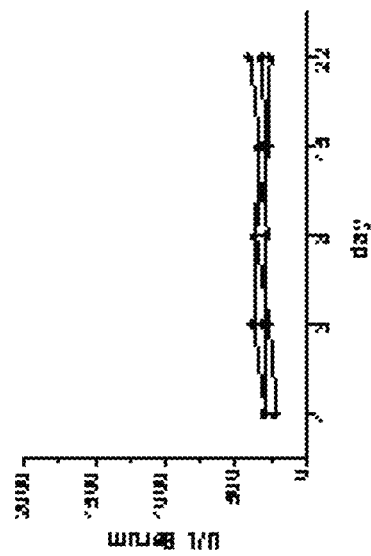
Figure 10E:
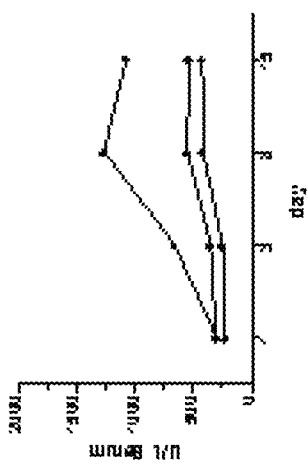
Figure 10G:
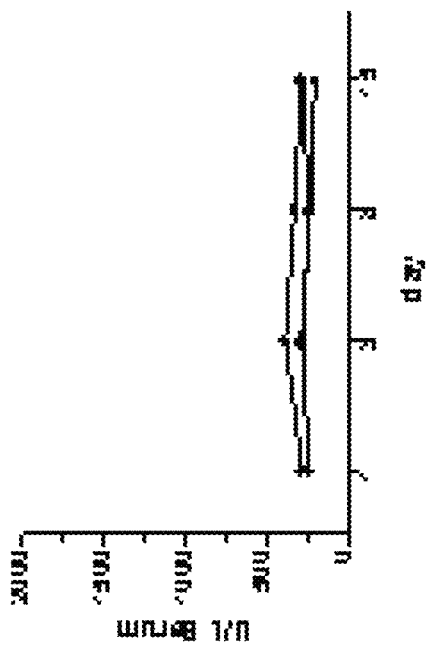
Figure 10J:
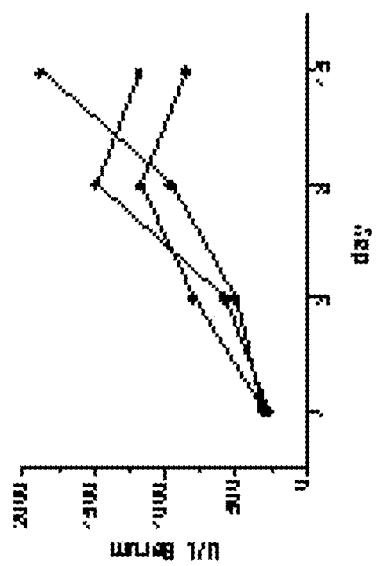
Figure 10I:
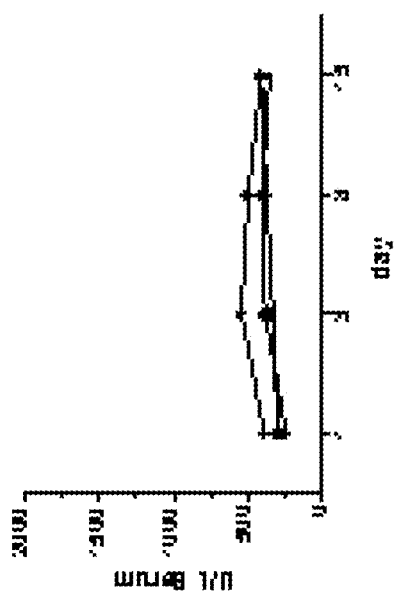

Nonhuman primate (NHP) toxicity studies were performed in female cynomolgus monkeys. All study protocols were approved by testing facility Institutional Animal Care and Use Committee. A non-GLP single dose toxicity studies was performed using intravenous (IV) injection of escalating doses in a three week interval. Comprehensive toxicology parameters were assessed in each study including physical examinations, body weights, food consumption, behavior, clinical chemistry, urinalysis and hematology, Blood samples were collected at various time points. As an example of tolerability the time course of parameter LDH in blood is shown for Her2-30.0643 (FIG. 10A); Her2-30.1465 (FIG. 10B); Her2-A118C-30.0880 (FIGS. 10C-10F); Her2-D265C-30.0880 (FIG. 10G-10J). Doses are 0.3 mg/kg (FIGS. 10A-10C and 10G); 1 mg/kg (FIGS. 10D and 10H); 3 mg/kg (FIGS. 10E and 10I); 10 mg/kg (FIGS. 10F and 10J);

Mass Spectrometry (LC-MS) (FIGS. 4A-5C)

Prior to MS analysis, antibodies and antibody drug conjugates were deglycosylated and reduced using standard protocols. Thus, after deglycosylation with PNGase F and dialysis, antibody and antibody drug conjugate solutions were precipitated by addition of acetonitrile, centrifuged and the precipitate reconstituted in a 6 M guanidinium hydrochloride solution. For light and heavy chain analysis reconstituted solutions were reduced with 20 mM dithiothreitol for 30 min at 56° C. Deglycosylated as well as reduced antibodies and antibody drug conjugates were then analyzed by nano LC-MS using a LTQ Orbitrap Elite. ion trap mass spectrometer (Thermo Fisher Scientific), Methods were optimized for intact and reduced antibodies prior analysis. Obtained mass spectra were finally de-convoluted by appropriate software (ProMass, Thermo Fisher Scientific) for data interpretation.

What is claimed is:

1. A conjugate of generic formula:

Ama-L-X—S-Ab, wherein Ama is an amatoxin, L is a linker, X is a moiety resulting from coupling of a thiol group to a thiol-reactive group, S is the sulphur atom of a cysteine amino acid residue, and Ab is an antibody sequence, or a functional antibody fragment, comprising said cysteine residue, wherein said cysteine residue is heavy chain 265Cys.

2. The conjugate of claim 1, wherein the linker is selected from a stable linker and a cleavable linker.

3. The conjugate of claim 1, wherein the thiol-reactive group is selected from bromo.acetamide, iodo acetamide, 4,6-dichloro-1,3,5-triazin-2-ylamino, 4-[5-(methylsulfonyl)-1H-tetrazole-1-yl]phenyl, 2-(methylsulfonyl)-benzo[d]thiazole-5-yl, 4-[5-(methylsulfonyl)-1,3,4-oxadiazol-2-yl]-phenyl, 2-pyridyldithio-, 2-(5-nitro-pyridiyl)dithio-, methylthiosulfonyl and maleimide.

4. The conjugate of claim 1, wherein the thiol-reactive group is maleimide.

5. A pharmaceutical composition comprising the conjugate according to claim 1.

6. A method of treating a disease associated with mammalian cells presenting a target, comprising the step of: contacting said mammalian cells with a conjugate according to claim 1, wherein said antibody, or functional antibody fragment, is specific for said target.

7. A method for synthesizing a conjugate of generic formula:

Ama-L-X—S-Ab by reacting a compound Ama-L-X', wherein X is a thiol-reactive group, with an antibody, or a functional antibody fragment, Ab-SH, wherein the group —SH is a thiol of a cysteine amino acid residue, and Ab is an antibody sequence, or sequence of a functional antibody fragment, comprising said cysteine residue, wherein said cysteine residue is heavy chain 265Cys.

8. The method of claim 7, further comprising synthesizing the compound Ama-L-X', wherein X is a maleimide group comprising the step of (a) reacting an amatoxin comprising a nucleophilic group with a compound Y-L-X" wherein Y is a leaving group, and X" is a protected maleimide group.

9. A kit comprising (i) a compound Ama-L-X', wherein X' is a thiol-reactive group, and (ii) an antibody, or a functional antibody fragment, Ab-SH, wherein the group —SH is a thiol of a cysteine amino acid residue, and Ab is an antibody sequence, or sequence of a functional antibody fragment, comprising said cysteine residue, wherein said cysteine residue is heavy chain 265Cys.

* * * * *